United States Patent
Watanabe et al.

(10) Patent No.: US 7,629,108 B2
(45) Date of Patent: *Dec. 8, 2009

(54) NITROGEN-CONTAINING ORGANIC COMPOUND, RESIST COMPOSITION AND PATTERNING PROCESS

(75) Inventors: Takeru Watanabe, Joetsu (JP); Youichi Ohsawa, Joetsu (JP); Masaki Ohashi, Joetsu (JP); Wataru Kusaki, Joetsu (JP); Tomohiro Kobayashi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 3 days.

This patent is subject to a terminal disclaimer.

(21) Appl. No.: 11/976,426

(22) Filed: Oct. 24, 2007

(65) Prior Publication Data

US 2008/0102405 A1 May 1, 2008

(30) Foreign Application Priority Data

Oct. 25, 2006 (JP) .............................. 2006-289489

(51) Int. Cl.
*G03F 7/00* (2006.01)
*G03F 7/004* (2006.01)

(52) U.S. Cl. ............................. 430/270.1; 544/1; 546/1; 548/100

(58) Field of Classification Search .............. 430/270.1, 430/326, 325, 330

See application file for complete search history.

(56) References Cited

U.S. PATENT DOCUMENTS

| 4,491,628 | A | 1/1985 | Ito et al. |
|---|---|---|---|
| 5,310,619 | A | 5/1994 | Crivello et al. |
| 5,362,607 | A | 11/1994 | Crivello et al. |
| 5,580,695 | A | 12/1996 | Murata et al. |
| 7,276,324 | B2 * | 10/2007 | Watanabe et al. ........ 430/270.1 |

FOREIGN PATENT DOCUMENTS

| JP | 2-27660 B2 | 6/1990 |
|---|---|---|
| JP | 5-232706 A | 9/1993 |
| JP | 63-27829 A | 11/1994 |

OTHER PUBLICATIONS

W. Hinsberg et al. J. Photoply. Sci. and Tech., vol. 6, No. 4, pp. 535-546 (1993).
T. Kumada et al., J. Photoplym Sci. and Tech., vol. 6, No. 4, pp. 571-574 (1993).
Hatakeyama et al., J. Photoplym. Sci. and Tech., vol. 13, No. 4, pp. 535-546 (1993).

* cited by examiner

*Primary Examiner*—Amanda C. Walke
(74) *Attorney, Agent, or Firm*—Birch, Stewart, Kolasch & Birch, LLP

(57) ABSTRACT

A resist composition comprising as a quencher a nitrogen-containing organic compound bearing a nitrogen-containing heterocycle and having a molecular weight of at least 380 exhibits a high resolution and satisfactory mask coverage dependence and is useful in microfabrication using electron beam or deep-UV.

10 Claims, No Drawings

US 7,629,108 B2

NITROGEN-CONTAINING ORGANIC COMPOUND, RESIST COMPOSITION AND PATTERNING PROCESS

CROSS-REFERENCE TO RELATED APPLICATION

This non-provisional application claims priority under 35 U.S.C. §119(a) on Patent Application No. 2006-289489 filed in Japan on Oct. 25, 2006, the entire contents of which are hereby incorporated by reference.

TECHNICAL FIELD

The present invention relates to a novel nitrogen-containing organic compound of specific structure, a chemically amplified resist composition comprising the same and suitable for microfabrication technology, and a patterning process using the resist composition.

BACKGROUND ART

Of the efforts currently being made to achieve a finer pattern rule in the drive for higher integration and operating speeds in LSI devices, deep-ultraviolet lithography is thought to hold particular promise as the next generation lithography in microfabrication technology. Deep-UV lithography is capable of fabrication to dimensions of 0.2 µm or less and, when a resist having low light absorption is used, can form patterns with sidewalls that are nearly perpendicular to the substrate. One technology that has attracted a good deal of attention recently utilizes high-intensity KrF and ArF excimer lasers as the deep-UV light source. This technology is being used in production, prompting a desire for resists having a low light absorption and a high sensitivity.

Acid-catalyzed chemically amplified resists (e.g., U.S. Pat. No. 4,491,628 and U.S. Pat. No. 5,310,619, or JP-B 2-27660 and JP-A 63-27829) developed in response to the above needs are endowed with excellent properties, including a high sensitivity, high resolution and good dry-etching resistance, which make them especially promising as resists for deep-UV lithography.

However, one problem with chemically amplified resists is that, when the standing time from exposure to post exposure bake (PEB) is long, the line pattern formed during patterning acquires a "T-top" shape characterized by widening at the top of the pattern. This drawback is called "post exposure delay" (PED). Another problem with such resists is "footing," which is a widening of the resist pattern close to the substrate that occurs on a basic substrate, particularly a silicon nitride or titanium nitride substrate. The T-top effect is believed to result from a decrease in solubility at the surface of the resist film, and the footing effect at the substrate surface appears to arise from a decline in solubility near the substrate. An additional problem is that elimination of acid labile groups, which is a dark reaction, proceeds during the interval between the exposure step and the PEB step, reducing the final dimensions of the pattern lines. These problems represent major drawbacks to the practical use of chemically amplified resists. Because of such defects, prior-art chemically amplified resists are difficult to dimensionally control in the lithographic process, and dimensional control is also lost during dry etching of the substrate (see, for example, W. Hinsberg et al., Journal of Photopolymer Science and Technology, Vol. 6, No. 4, 535-546 (1993); and T. Kumada et al., ibid., 571-574).

In chemically amplified resist materials, the problems of PED and footing on the substrate surface are believed to be caused in large part by basic compounds which are either airborne or present on the surface of the substrate. The acid at the surface of the resist film that has been generated by exposure reacts with airborne bases and is deactivated. Prolonged standing until post-exposure bake results in a corresponding increase in the amount of deactivated acid, making it more difficult for the acid-labile groups to decompose. A substantially insolubilized layer thus forms at the surface, giving the resist pattern a T-top shape.

It is well-known in the art that the addition of a nitrogen-containing compound can decrease the influence of airborne bases, and is thus effective also against PED (see, for example, JP-A 5-232706 and JP-A 7-134419). Familiar nitrogen-containing compounds having significant addition effects include amine compounds and amide compounds. Specific examples include pyridine, polyvinylpyridine, aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3-phenylenediamine, 1,4-phenylenediamine, 2-quinolinecarboxylic acid, 2-amino-4-nitrophenol, and 2-(p-chlorophenyl)-4,6-trichloromethyl-S-triazine.

These nitrogen-containing compounds are weak bases and can alleviate the T-top problem, but such compounds are unable to control the reaction when highly reactive acid-labile groups are used; that is, they cannot control acid diffusion fully. With the addition of a weak base, the dark reactions during PED in particular proceed in unexposed areas as well, causing slimming of the line dimensions and a loss of film thickness from the line surface during PED. To overcome such problems, it is desirable to add a strong base. However, a higher basicity is not necessarily better. For example, good effects cannot be obtained with the addition of the following super-strong bases:

DBU (1,8-diazabicyclo[5.4.0]-7-undecene),
DBN (1,5-diazabicyclo[4.3.0]-5-nonene) and proton sponge (1,8-bis(dimethylamino)naphthalene) or quaternary ammonium hydroxides such as tetramethylammonium hydroxide.

The addition of a nitrogen-containing compound having an excellent effect of kinetically capturing the acid generated works well to increase the contrast and thereby achieve a high resolution. The dissociation constants of the acid and base within water can be explained in terms of pKa, but the kinetic acid capturing ability within the resist film is not directly related to the pKa of the nitrogen-containing compound. This is discussed by Hatakeyama et al. in Journal of Photopolymer Science and Technology, Vol. 13, No. 4, pp. 519-524 (2000). The structure of nitrogen-containing organic compounds suited to achieve a high resolution is described in JP-A 2002-226470, JP-A 2004-347736, and JP-A 2004-347738. Note that compounds which exert an acid capturing effect in the resist as typified by nitrogen-containing organic compounds are generally referred to as "quencher."

In addition, it now becomes evident that the mask coverage dependency (i.e., differences in pattern profile and size between a bright field with a low coverage and a dark field with a high coverage) and the number of defects are dictated by the identity of a nitrogen-containing organic compound to be added to a resist composition. It would be desirable to have a nitrogen-containing organic compound which can reduce the mask coverage dependency and inhibit defect occurrence.

For achieving a further reduction of feature size, there now exists a demand to have a resist material suited for the immersion lithography. The ArF immersion lithography generally uses pure water as the immersion liquid. In the immersion lithography, water is held between a resist film as prebaked and a projection lens during exposure. The immersion lithography is an important technology that enables the ArF lithography to survive to a node of 65 nm or less if combined with a projection lens with NA of 1.0 or more, and a further development thereof is being accelerated. In the immersion lithography, if the resist material contains a water-soluble nitrogen-containing organic compound, the nitrogen-containing compound can be partially leached in the immersion water during exposure, whereby the resist pattern is degraded in rectangularity. It would be desirable to have a nitrogen-containing organic compound which is less water-soluble and achieves a high resolution.

SUMMARY OF THE INVENTION

It is therefore an object of the invention to provide a chemically amplified resist composition which exhibits a high resolution and reduces mask coverage dependency, when processed by photolithography for micropatterning, especially lithography using a light source such as a KrF laser, ArF laser, $F_2$ laser, extremely short UV, electron beam or x-ray, and is applicable to the immersion lithography. Another object of the invention is to provide a patterning process which uses the resist composition. A further object of the invention is to provide a novel nitrogen-containing organic compound suited for use in the resist composition.

According to the invention, there is provided a resist composition comprising as a quencher at least one nitrogen-containing organic compound bearing a nitrogen-containing heterocycle and having a molecular weight of at least 380, represented by the general formula (1).

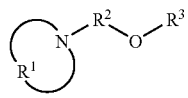
(1)

Herein $R^1$ is a straight, branched or cyclic divalent substituent group of 2 to 20 carbon atoms to form a nitrogen-containing heteroaliphatic or heteroaromatic ring with the nitrogen atom to which it is attached at both ends, which group may contain an oxygen, nitrogen, sulfur or halogen atom, $R^2$ is a straight or branched alkylene group of 2 to 10 carbon atoms which may contain a carbonyl group, and $R^3$ is an alkyl or acyl group of 22 to 50 carbon atoms which may contain a hydroxyl, carbonyl, ester, ether or cyano group.

The invention also provides a resist composition comprising as a quencher at least one of nitrogen-containing organic compounds bearing a nitrogen-containing heterocycle and having a molecular weight of at least 430, represented by the general formulae (2) to (10).

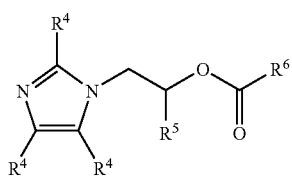
(2)

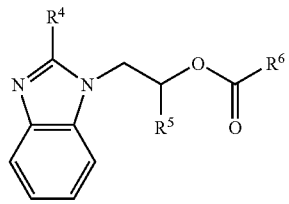
(3)

(4)

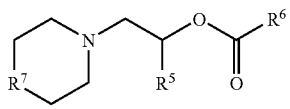
(5)

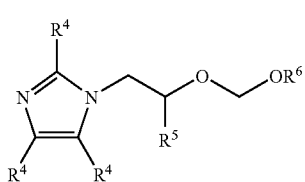
(6)

(7)

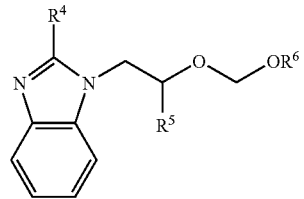
(8)

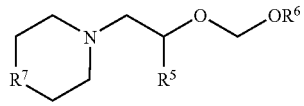
(9)

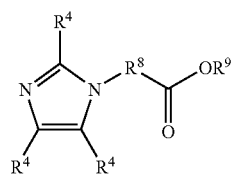
(10)

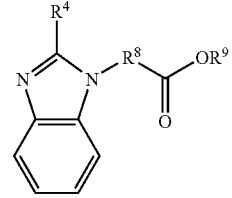

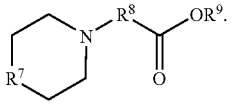

Herein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^6$ is an alkyl group of 21 to 49 carbon atoms which may contain a hydroxyl, carbonyl, ester, ether, cyano or acetal group, $R^7$ is a single bond, methylene group, oxygen atom or sulfur atom, $R^8$ is a straight or branched $C_1$-$C_9$ alkylene group, and $R^9$ is an alkyl group of 22 to 50 carbon atoms which may contain a hydroxyl, carbonyl, ester, ether or cyano group.

The invention further provides a resist composition comprising as a quencher at least one of nitrogen-containing organic compounds bearing a nitrogen-containing heterocycle and a steroid structure and having a molecular weight of at least 430, represented by the general formulae (2') to (10').

(2')
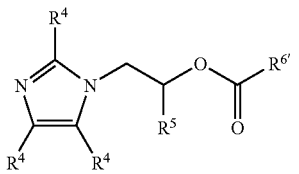

(3')
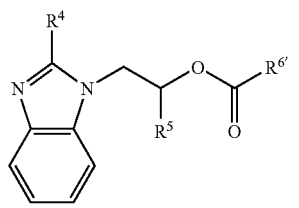

(4')
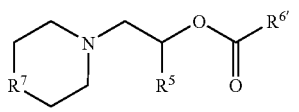

(5')
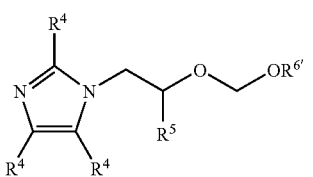

(6')
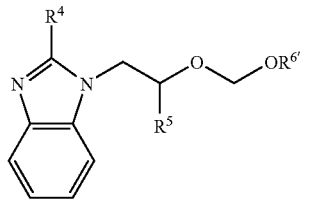

(7')
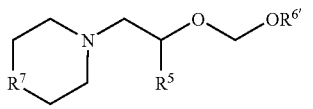

(8')
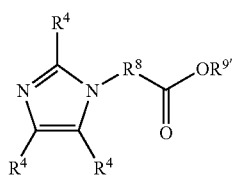

(9')
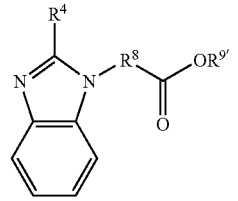

-continued (10')
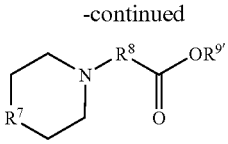

Herein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^{6'}$ is an alkyl group of 21 to 49 carbon atoms having a steroid structure which may contain a hydroxyl, carbonyl, ester, ether, cyano or acetal group, $R^7$ is a single bond, methylene group, oxygen atom or sulfur atom, $R^8$ is a straight or branched $C_1$-$C_9$ alkylene group, and $R^{9'}$ is an alkyl group of 22 to 50 carbon atoms having a steroid structure which may contain a hydroxyl, carbonyl, ester, ether or cyano group.

One embodiment of the invention is a positive resist composition comprising (A) a nitrogen-containing organic compound of any one of the formulae (1) to (10), (2') to (10'), (B) an organic solvent, (C) a base resin having an acid labile group-protected acidic functional group which is alkali-insoluble or substantially alkali-insoluble, but becomes alkali-soluble when the acid labile group is deprotected, (D) an acid generator, and optionally, (E) a dissolution regulator.

Another embodiment of the invention is a negative resist composition comprising (A) the nitrogen-containing organic compound of any one of the formulae (1) to (10), (2') to (10'), (B) an organic solvent, (C') a base resin which is alkali-soluble, but becomes substantially alkali-insoluble when crosslinked with a crosslinker, (D) an acid generator, and (F) a crosslinker for inducing crosslinkage under the action of an acid.

The chemically amplified resist compositions described above have an improved resolution and reduced mask coverage dependence and are best suited in photolithography microfabrication.

In another aspect, the invention provides a patterning process comprising the steps of (i) applying the resist composition defined above onto a substrate to form a coating, (ii) heat treating the coating, then exposing it through a photomask to high-energy radiation having a wavelength of up to 300 nm or an electron beam, and (iii) heat treating the exposed coating, then developing it with a developer.

By the patterning process using the chemically amplified resist composition of the invention, a resist pattern with an improved resolution and reduced mask coverage dependence can be formed. The process is best suited in photolithography microfabrication.

In a further aspect, the invention provides a nitrogen-containing organic compound bearing a nitrogen-containing heterocycle, represented by one of the general formulae (2) to (10); or a nitrogen-containing organic compound bearing a nitrogen-containing heterocycle and a steroid structure, represented by one of the general formulae (2') to (10').

The nitrogen-containing organic compounds of formulae (2) to (10) and (2') to (10') can be conveniently prepared in high yields by the method described later. When they are added to resist components in appropriate amounts, the resulting resist compositions exhibit an improved resolution and reduced mask coverage dependence. For a certain application, a proper choice of $R^4$ to $R^9$, $R^{6'}$ and $R^{9'}$ enables to optimize resist characteristics including a pattern profile.

BENEFITS OF THE INVENTION

The resist compositions prepared by compounding the nitrogen-containing organic compounds exhibit a high resolution and improved mask coverage dependence and are useful in lithographic micropatterning using electron beam and deep UV. The nitrogen-containing organic compounds exert best effects when compounded in positive or negative resists adapted for KrF laser, ArF laser, $F_2$ laser, EUV, EB or x-ray lithography, making the resists ideal as a micropatterning material in VLSI fabrication. The compositions are effective not only in conventional lithography, but also in immersion lithography.

DESCRIPTION OF THE PREFERRED EMBODIMENTS

The terms "a" and "an" herein do not denote a limitation of quantity, but rather denote the presence of at least one of the referenced item.

As used herein, the notation ($C_n$-$C_m$) means a group containing from n to m carbon atoms per group.

As used herein, the abbreviation Me stands for methyl, Ph stands for phenyl, and Ac stands for acetyl.

Nitrogen-containing Compound

The inventors sought for a compound which when compounded in chemically amplified resist compositions, is effective for achieving a high resolution and improved mask coverage dependence. The inventors have discovered that a nitrogen-containing organic compound bearing a nitrogen-containing heterocycle and having a molecular weight of at least 380 represented by the general formula (1) can be combined in proper amounts with a base resin and other components to formulate a chemically amplified photoresist composition which exhibits a high resolution and improved mask coverage dependence. Specifically nitrogen-containing organic compounds bearing a nitrogen-containing heterocycle and having a molecular weight of at least 430, represented by the general formulae (2) to (10), and more specifically nitrogen-containing organic compounds bearing a nitrogen-containing heterocycle and a steroid structure and having a molecular weight of at least 430, represented by the general formulae (2') to (10') are effective. The resist composition can be advantageously used in the immersion lithography because the leaching of amine compounds in water is minimized during water immersion.

The nitrogen-containing organic compounds to be compounded in chemically amplified resist compositions are nitrogen-containing organic compounds bearing a nitrogen-containing heterocycle and having a molecular weight of at least 380, represented by the general formula (1).

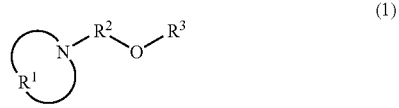
(1)

Herein $R^1$ is a straight, branched or cyclic divalent substituent group of 2 to 20 carbon atoms to form a nitrogen-containing heteroaliphatic ring or nitrogen-containing heteroaromatic ring with the nitrogen atom to which it is attached at both ends, which group may contain an oxygen, nitrogen, sulfur or halogen atom, $R^2$ is a straight or branched alkylene group of 2 to 10 carbon atoms which may contain a carbonyl group, and $R^3$ is an alkyl or acyl group of 22 to 50 carbon atoms which may contain a hydroxyl, carbonyl, ester, ether or cyano group.

In formula (1), $R^1$ stands for a straight, branched or cyclic divalent substituent group of 2 to 20 carbon atoms to form a nitrogen-containing heteroaliphatic ring or nitrogen-containing heteroaromatic ring with the nitrogen atom to which it is attached at both ends, which group may contain an oxygen, nitrogen, sulfur or halogen atom. Examples of the nitrogen-containing heteroaliphatic ring that $R^1$ forms with the nitrogen atom to which it is attached at both ends include, but are not limited to, aziridine, azetidine, pyrrolidine, piperidine, 2-imidazolidine, 2-pyrroline, pyrazolidine, piperazine, 3-pyrazoline, morpholine, thiomorpholine, and alkyl- and aryl-derivatives of the foregoing. Examples of the nitrogen-containing heteroaromatic ring that $R^1$ forms with the nitrogen atom to which it is attached at both ends include, but are not limited to, pyrrole, imidazole, pyrazole, triazole, tetrazole, benzimidazole, 1H-indazole, purine, perimidine, phenoxazine, phenothiazine, and alkyl- and aryl-derivatives of the foregoing.

In formula (1), $R^2$ stands for a straight or branched alkylene group of 2 to 10 carbon atoms which may contain a carbonyl group. Examples include, but are not limited to, ethylene, trimethylene, tetramethylene, pentamethylene, hexamethylene, heptamethylene, octamethylene, nonamethylene, decamethylene, propylene, ethylethylene, and oxo substituted forms of the foregoing.

In formula (1), $R^3$ stands for an alkyl or acyl group of 22 to 50 carbon atoms which may contain a hydroxyl, carbonyl, ester, ether or cyano group, and more specifically a group of the formula: —CO—$R^6$, —$CH_2$—$OR^6$ or $R^9$, or —CO—$R^{6'}$, —$CH_2$—$OR^{6'}$ or $R^{9'}$ wherein $R^6$, $R^9$, $R^{6'}$ and $R^{9'}$ are defined later.

Illustrative examples of the nitrogen-containing organic compounds having formula (1) include, but are not limited to, those illustrated just below as well as the examples of the nitrogen-containing organic compounds having formulae (2) to (10) and (2') to (10'), which will be illustrated later.

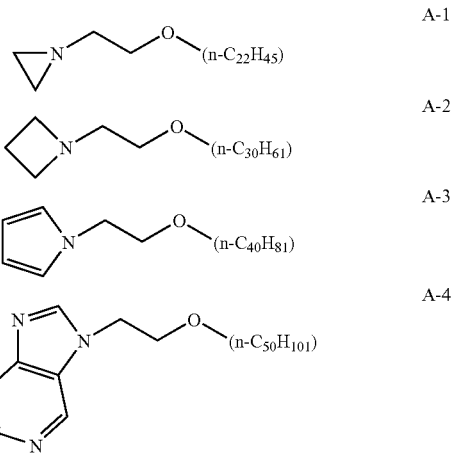

-continued

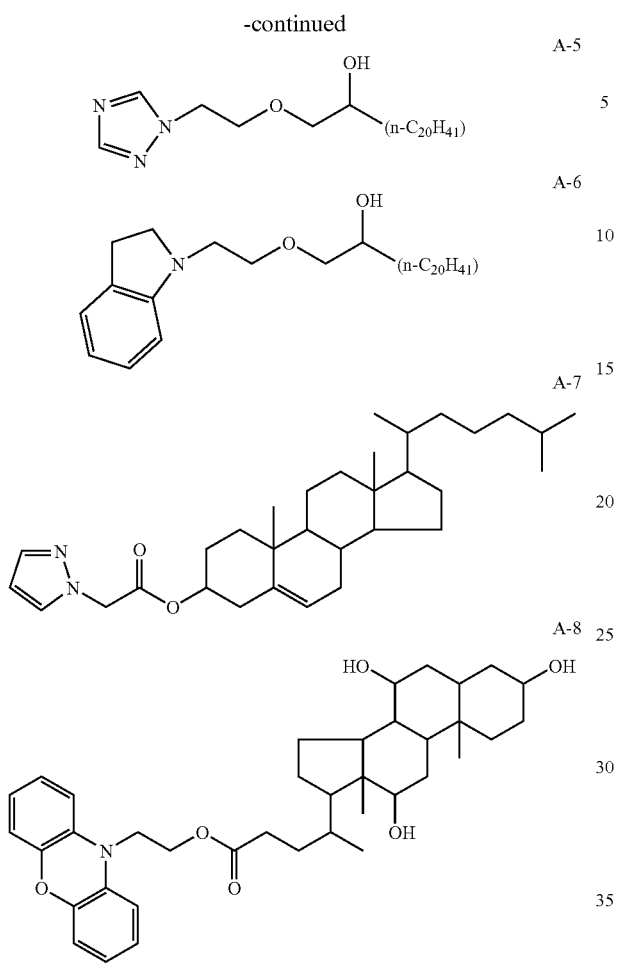

The preferred nitrogen-containing organic compounds to be compounded in chemically amplified resist compositions are nitrogen-containing organic compounds bearing a nitrogen-containing heterocycle and having a molecular weight of at least 430, represented by the general formulae (2) to (10).

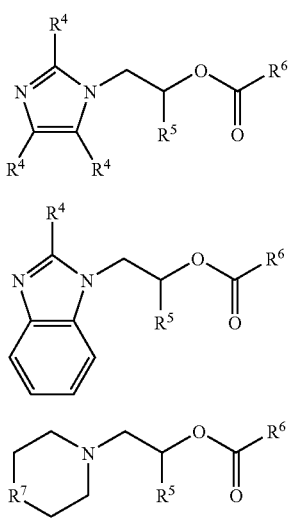

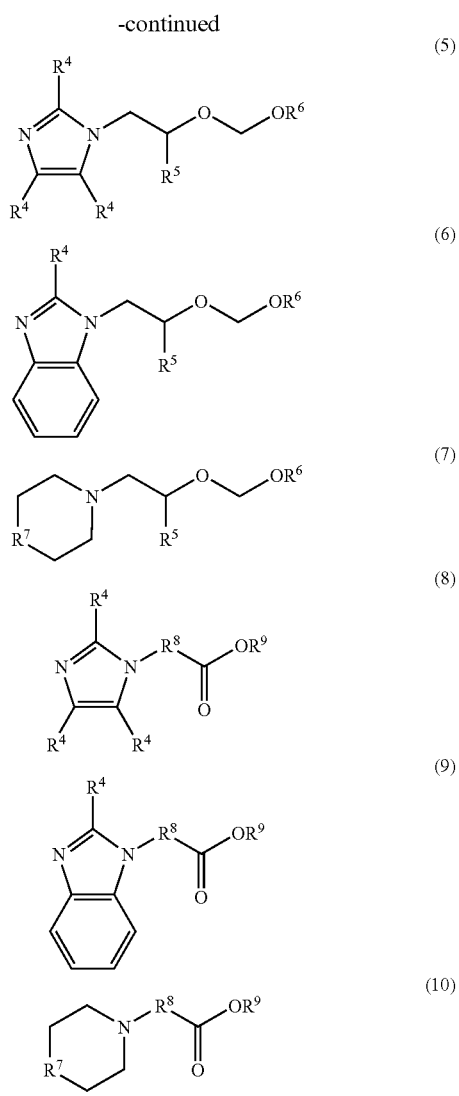

Herein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^6$ is an alkyl group of 21 to 49 carbon atoms which may contain a hydroxyl, carbonyl, ester, ether, cyano or acetal group, $R^7$ is a single bond, methylene group, oxygen atom or sulfur atom, $R^8$ is a straight or branched $C_1$-$C_9$ alkylene group, and $R^9$ is an alkyl group of 22 to 50 carbon atoms which may contain a hydroxyl, carbonyl, ester, ether or cyano group.

In formulae (2), (3), (5), (6), (8) and (9), $R^4$ each independently stands for a hydrogen atom, a straight, branched or cyclic $C_1$-$C_{10}$ alkyl group, a $C_6$-$C_{15}$ aryl group or a $C_7$-$C_{15}$ aralkyl group. Examples include hydrogen, methyl, ethyl, propyl, isopropyl, butyl, cyclohexyl, decyl, adamantyl, phenyl, naphthyl, and benzyl, with the hydrogen, methyl, ethyl and phenyl being preferred.

In formulae (2) to (7), $R^5$ stands for hydrogen or methyl.

In formulae (2) to (7), $R^6$ stands for an alkyl group of 21 to 49 carbon atoms which may contain a hydroxyl, carbonyl, ester, ether, cyano or acetal group, examples of which include those illustrated just below as well as the examples of $R^{6'}$ which will be illustrated later.

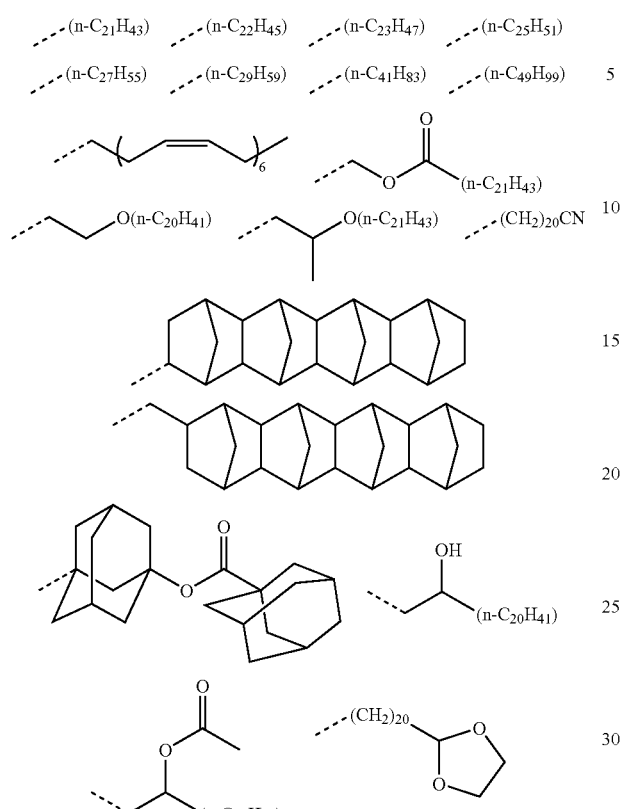

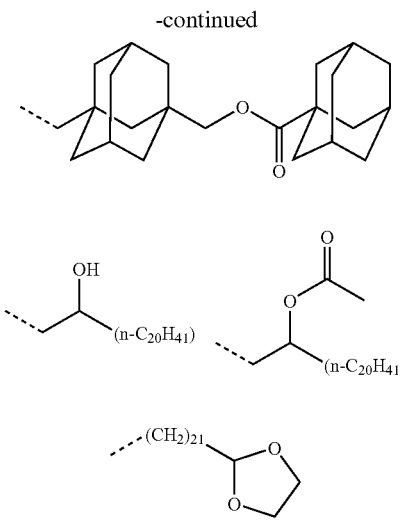

Note that the broken line denotes a bonding position.

In formulae (4), (7) and (10), $R^7$ stands for a single bond, methylene group, oxygen atom or sulfur atom, with the oxygen atom being preferred.

In formulae (8), (9) and (10), $R^8$ stands for a straight or branched $C_1$-$C_9$ alkylene group. $R^9$ stands for an alkyl group of 22 to 50 carbon atoms which may contain a hydroxyl, carbonyl, ester, ether or cyano group, examples of which include those illustrated just below as well as the examples of $R^{9'}$ which will be illustrated later.

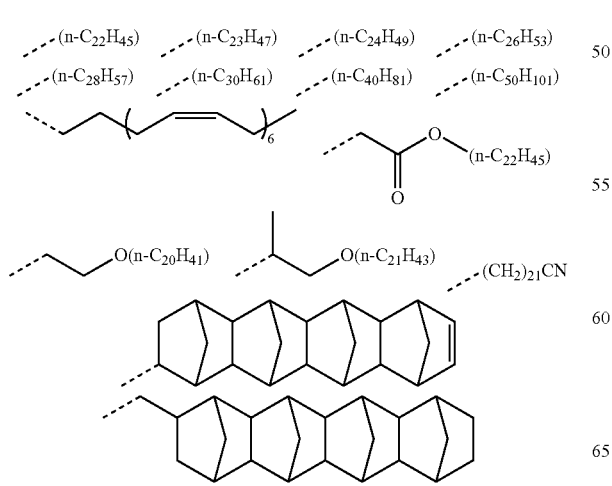

Illustrative examples of the nitrogen-containing organic compounds having formulae (2) to (10) include, but are not limited to, those illustrated just below as well as the examples of the nitrogen-containing organic compounds having formulae (2') to (10'), which will be illustrated later.

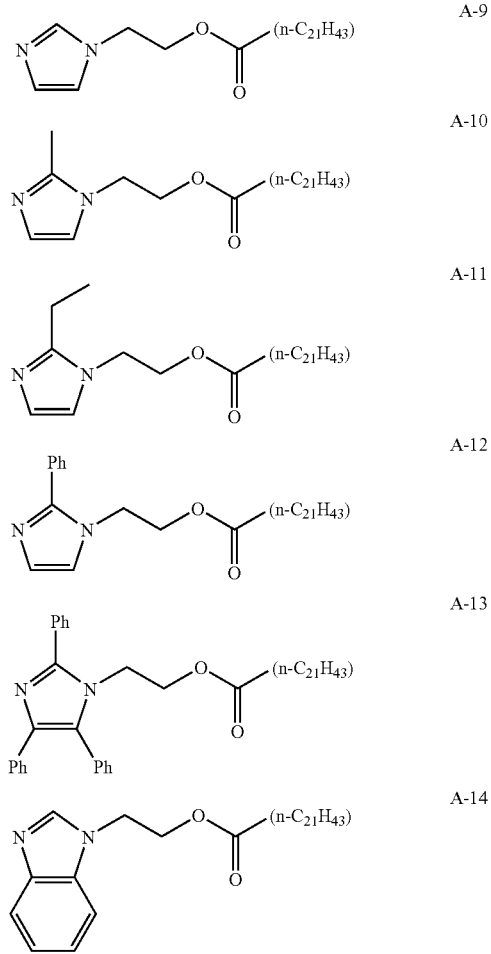

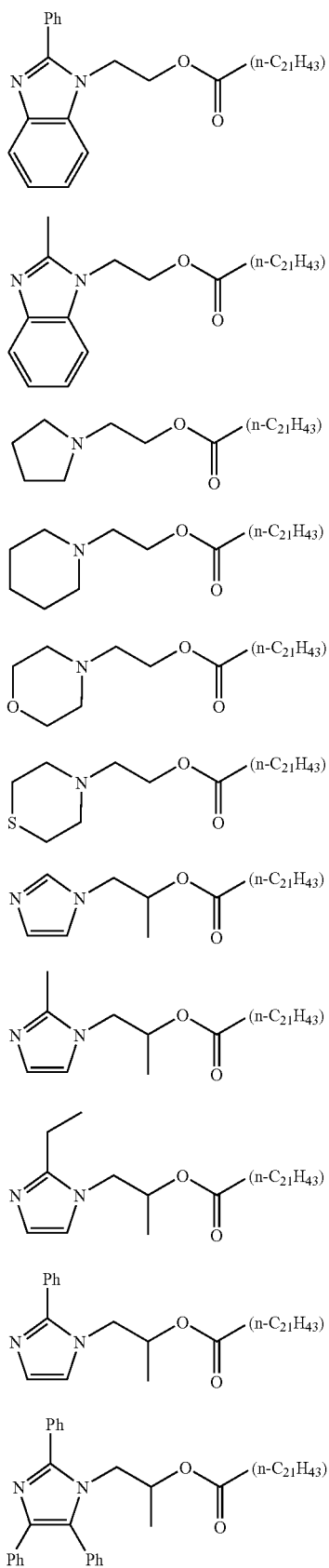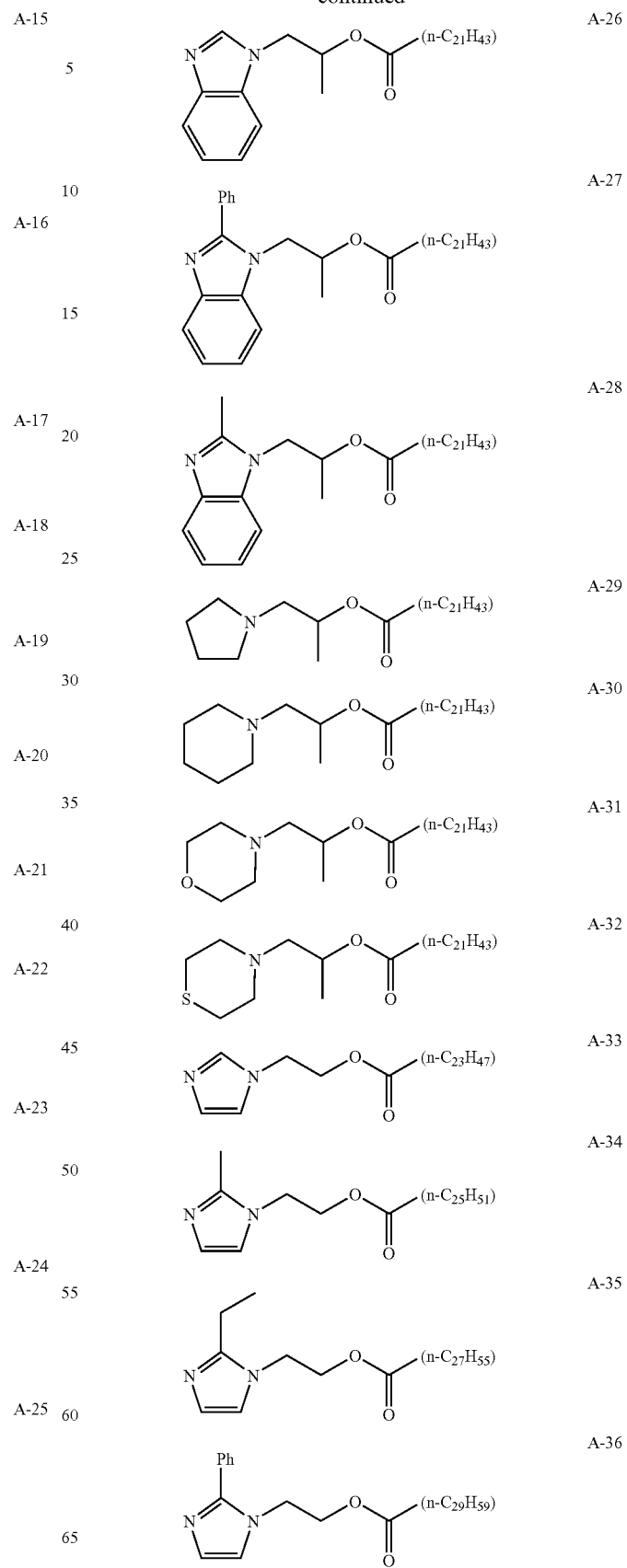

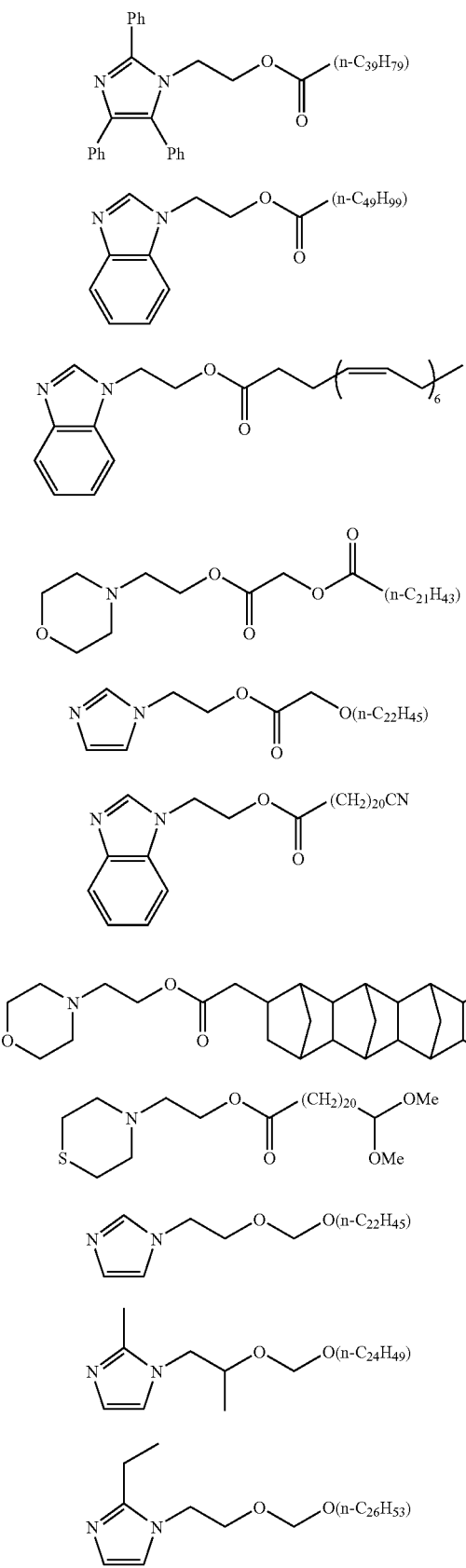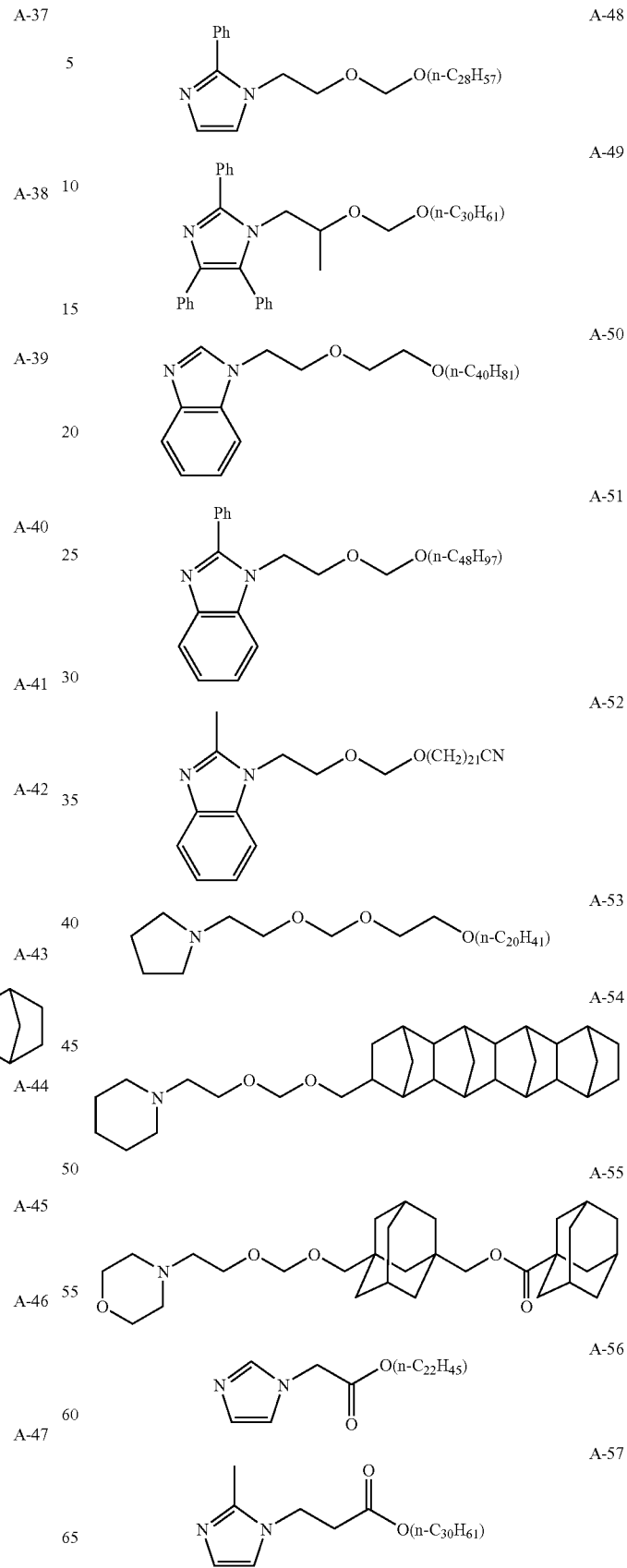

-continued

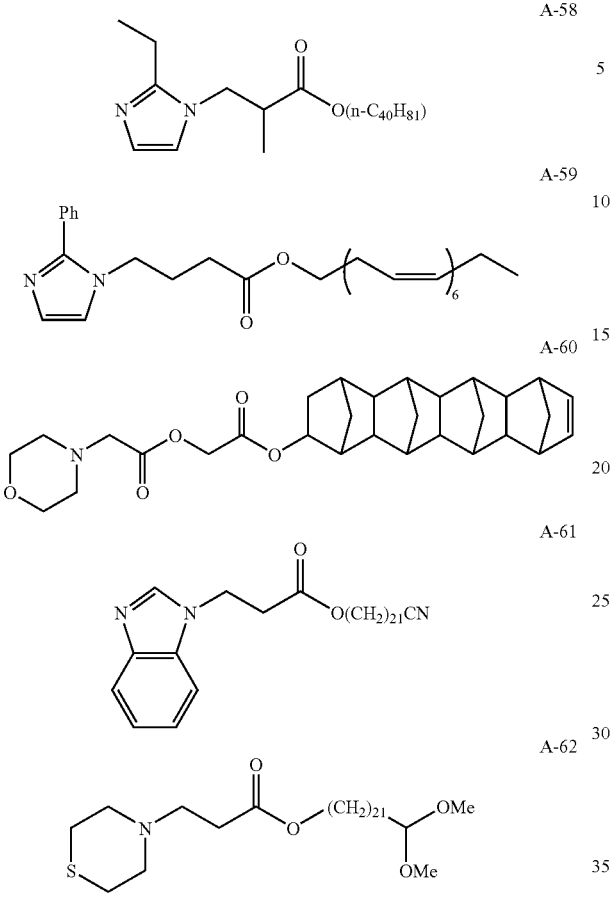

In a more preferred embodiment, the nitrogen-containing organic compounds to be compounded in chemically amplified resist compositions are nitrogen-containing organic compounds bearing a nitrogen-containing heterocycle and having a molecular weight of at least 430, represented by the general formulae (2') to (10').

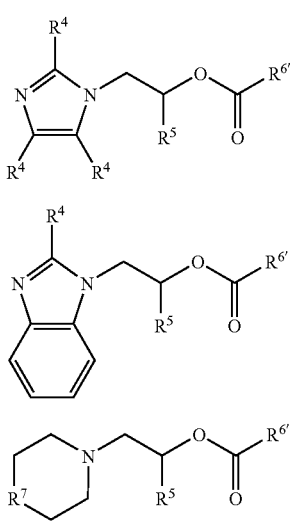

Herein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^{6'}$ is an alkyl group of 21 to 49 carbon atoms having a steroid structure which may contain a hydroxyl, carbonyl, ester, ether, cyano or acetal group, $R^7$ is a single bond, methylene group, oxygen atom or sulfur atom, $R^8$ is a straight or branched $C_1$-$C_9$ alkylene group, and $R^{9'}$ is an alkyl group of 22 to 50 carbon atoms having a steroid structure which may contain a hydroxyl, carbonyl, ester, ether or cyano group.

In formulae (2') to (10'), $R^4$, $R^5$, $R^7$, and $R^8$ are as illustrated above.

In formulae (2') to (7'), $R^{6'}$ stands for an alkyl group of 21 to 49 carbon atoms having a steroid structure which may contain a hydroxyl, carbonyl, ester, ether, cyano or acetal group, examples of which include the structures shown below, but are not limited thereto.

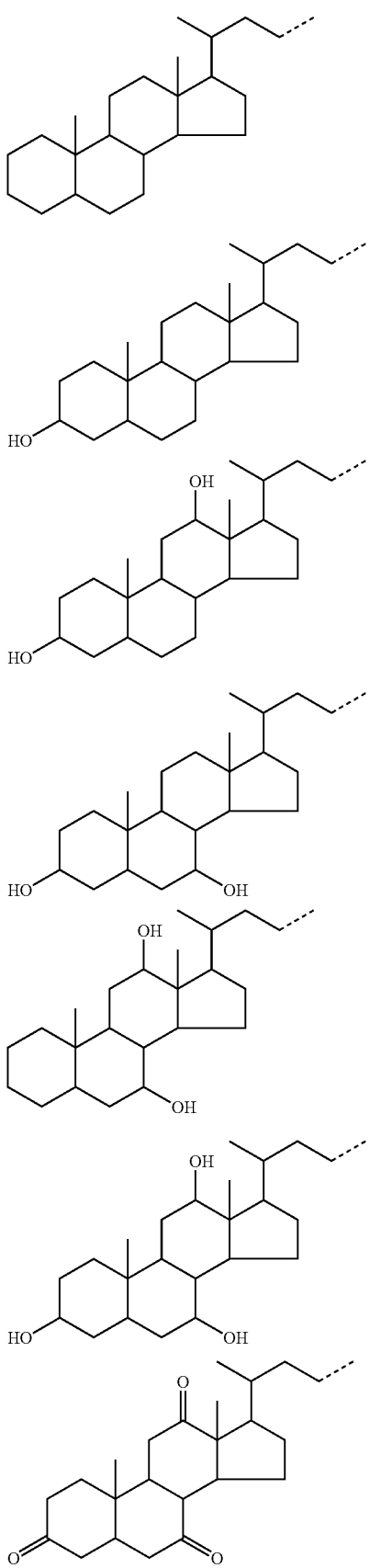
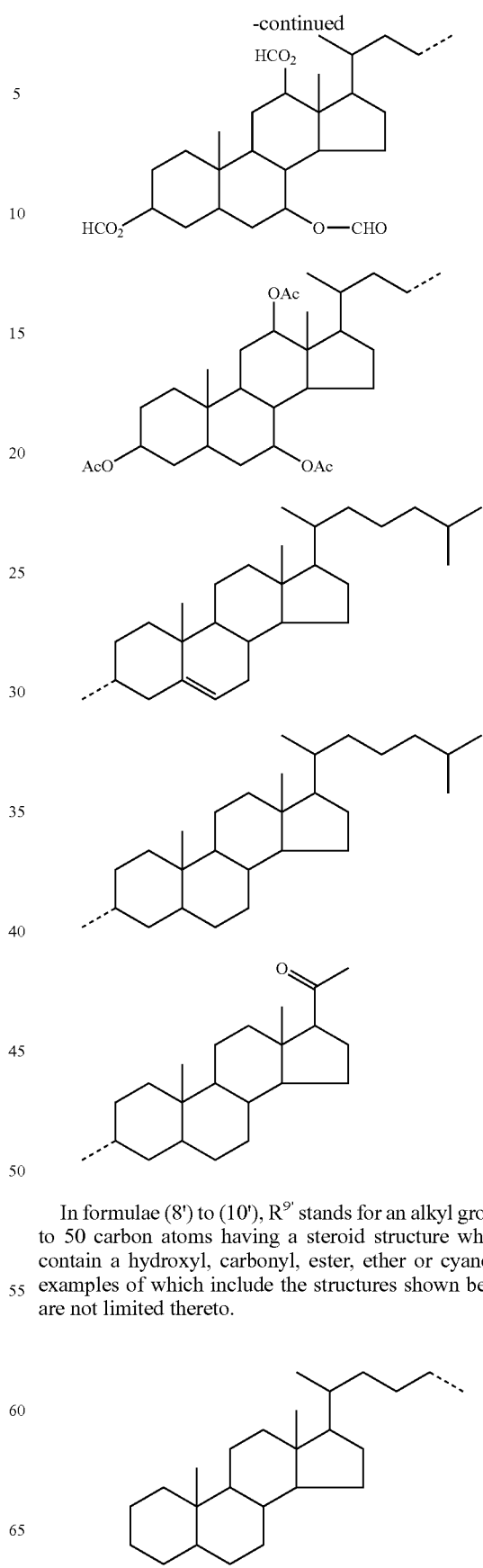
In formulae (8') to (10'), $R^{9'}$ stands for an alkyl group of 22 to 50 carbon atoms having a steroid structure which may contain a hydroxyl, carbonyl, ester, ether or cyano group, examples of which include the structures shown below, but are not limited thereto.
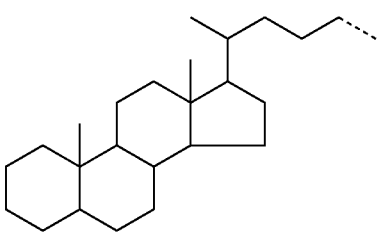

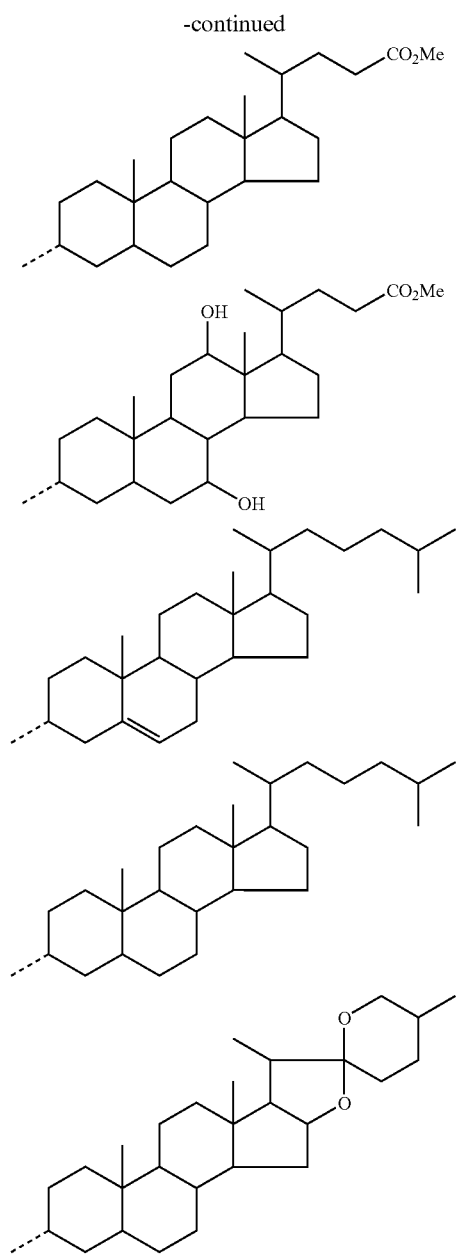
Illustrative examples of the nitrogen-containing organic compounds having formulae (2') to (10') are given below, but are not limited thereto.
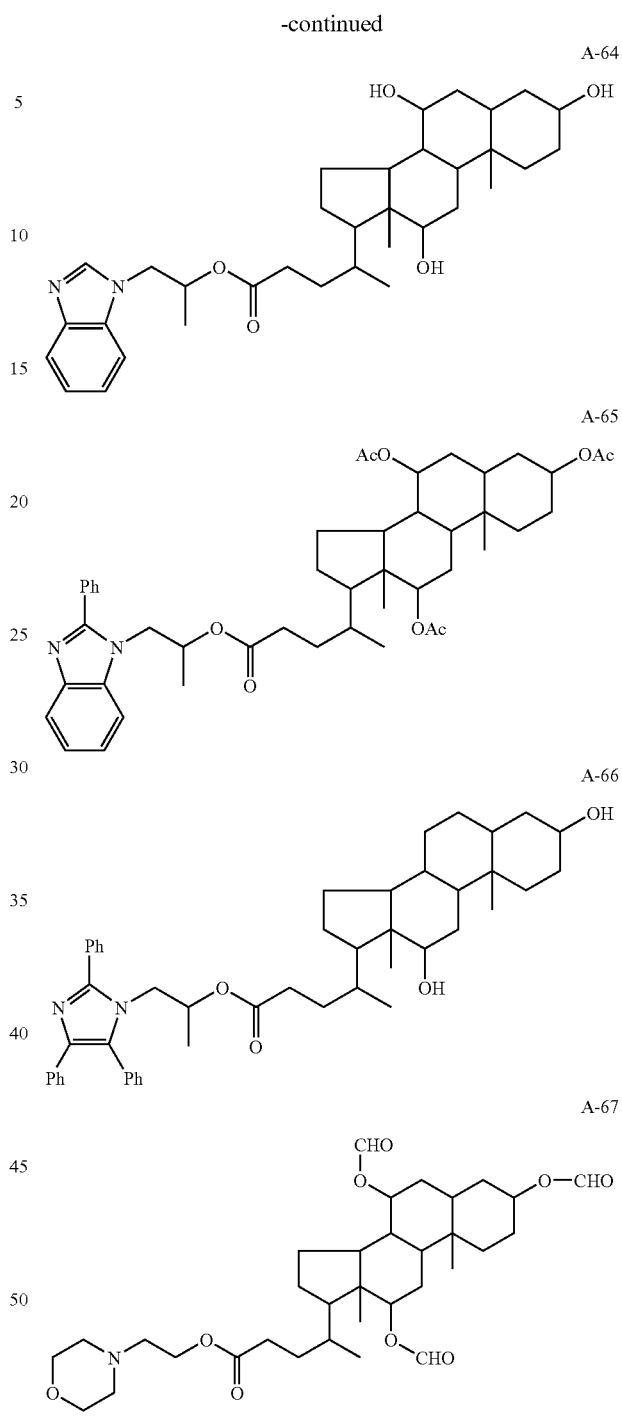
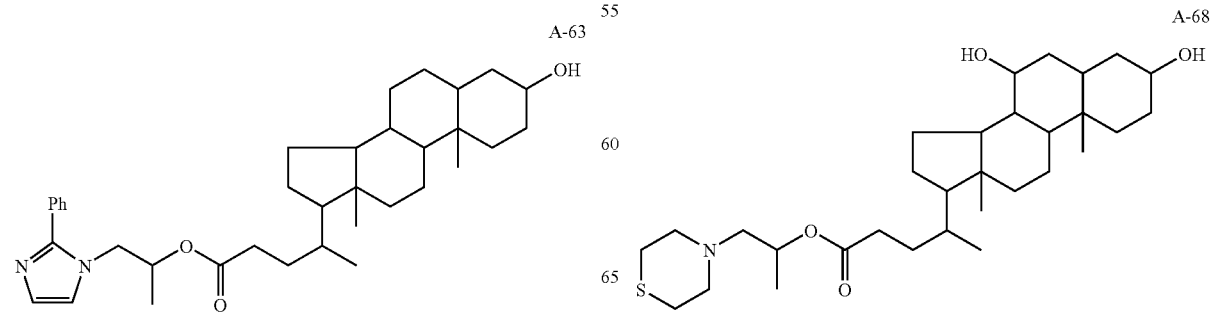

-continued

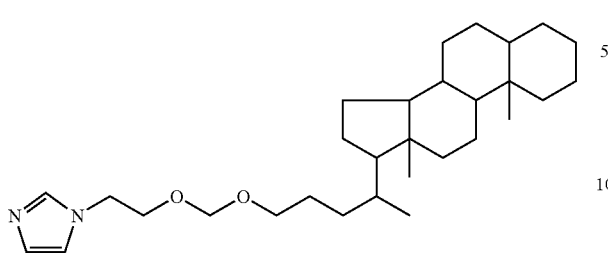

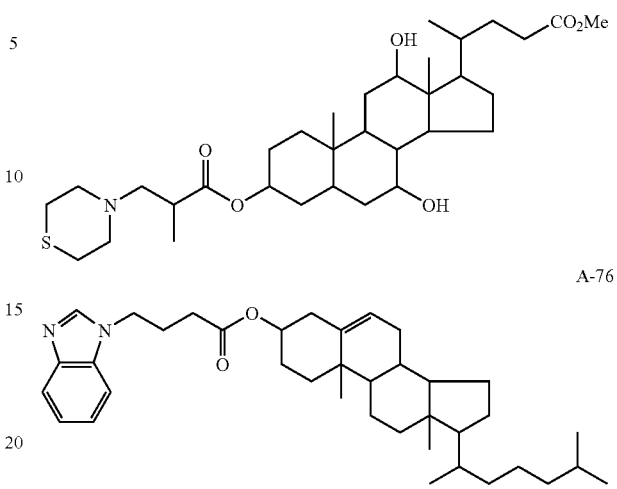

According to the invention, the nitrogen-containing organic compounds bear a nitrogen-containing heterocycle and have a molecular weight of at least 380. It is forecasted that the nitrogen-containing heterocyclic structure and a functional group positioned adjacent thereto such as ether, ester or acetal have a high affinity to acids to enable fast capturing of the acid generated by the photoacid generator, whereas the side-chain moiety with numerous carbon atoms represented by $R^3$ in formula (1) significantly affects the distribution and diffusion in the resist film of the nitrogen-containing organic compound as well as the volatilization and water-solubility thereof. As a result, a photoresist composition having added thereto the nitrogen-containing organic compound is endowed with a high resolution and reduced mask coverage dependence and is applicable to the immersion lithography. For a certain application, an optimal structure compound may be selected from among many possible nitrogen-containing organic compounds bearing a nitrogen-containing heterocycle and having a molecular weight of at least 380 according to the invention. That is, a nitrogen-containing organic compound may be selected having a basicity, a water solubility, an acid capturing rate and a diffusion rate within the resist in such a combination as to comply with a particular combination of the resist polymer with the photoacid generator and a particular lithography. This eventually enables to optimize resist material characteristics such as pattern profile.

The nitrogen-containing organic compounds of formulae (1) to (10) and (2') to (10') may be prepared by an optimum method that is selected in accordance with the structure of the compound. Typical methods include N-alkylation reaction of nitrogen-containing heterocyclic compounds having hydrogen on nitrogen and O-acylation or O-alkylation reaction of nitrogen-containing heterocyclic compounds having hydroxyalkyl substituent on nitrogen, but are not limited to these. These typical methods are described below in detail.

The first method is to produce nitrogen-containing organic compounds through N-alkylation reaction of nitrogen-containing heterocyclic compounds having hydrogen on nitrogen. This method is applicable to the synthesis of all the compounds having formulae (1) to (10) and (2') to (10'). The reaction is shown by the following scheme.

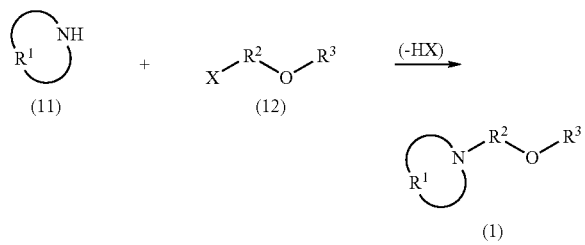

(1)

Herein $R^1$ is a straight, branched or cyclic divalent substituent group of 2 to 20 carbon atoms to form a nitrogen-containing heteroaliphatic or heteroaromatic ring with the nitrogen atom to which it is attached at both ends, which group may contain an oxygen, nitrogen, sulfur or halogen atom. $R^2$ is a straight or branched alkylene group of 2 to 10 carbon atoms which may contain a carbonyl group. $R^3$ is an alkyl or acyl group of 22 to 50 carbon atoms which may contain a hydroxyl, carbonyl, ester, ether or cyano group. X is a leaving group such as a halogen atom, p-toluenesulfonyloxy, methanesulfonyloxy, trifluoromethanesulfonyloxy or hydroxyl group.

An amount of compound (12) serving as an alkylating agent in the relevant reaction is desirably 0.1 to 10 moles, and more desirably 0.3 to 2 moles per mole of nitrogen-containing heterocyclic compound (II). The reaction may be carried out in a solvent or in the absence of a solvent. Suitable solvents include alcohols such as methanol, ethanol, isopropyl alcohol, t-butyl alcohol and ethylene glycol; hydrocarbons such as hexane, heptane, benzene, toluene and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacetamide, dimethyl sulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; and water. The solvent may be selected from the foregoing in accordance with the reaction conditions and used either singly or as mixtures thereof. The reaction temperature may be selected from a range of 0° C. to the reflux temperature of the solvent, in accordance with the reaction rate. A base may be added to the reaction system if necessary. Suitable bases include amines such as pyridine, triethylamine, diisopropylethylamine, 4-dimethylaminopyridine and imidazole; metal alkoxides such as sodium methoxide, sodium ethoxide and potassium t-butoxide; carbonates such as sodium carbonate, potassium carbonate and cesium carbonate; hydroxides such as sodium hydroxide, potassium hydroxide and tetramethylammonium hydroxide; metal hydrides such as sodium hydride and potassium hydride; organometallic compounds such as butyllithium and ethyl magnesium bromide; and metal amides such as lithium diisopropylamide. The base may be selected from the foregoing in accordance with the reaction conditions and used alone or in admixture. Alternatively the nitrogen-containing heterocyclic compound used as the reactant may serve as the base. It is desirable to use the base in an amount of from 0.1 to 10 moles, and especially from 0.5 to 5 moles per mole of the nitrogen-containing heterocyclic compound (II).

An iodide such as sodium iodide, lithium iodide or tetrabutylammonium iodide, or a bromide such as sodium bromide, lithium bromide or tetrabutylammonium bromide, may be added as a catalyst to increase the reaction rate. The amount of the catalyst, if added, is desirably from 0.001 to 2 moles, and especially from 0.005 to 0.5 mole, per mole of the nitrogen-containing heterocyclic compound (11). To maximize the final yield, it is desirable to monitor the progress of the reaction using gas chromatography (GC) or thin-layer chromatography (TLC) until the reaction is complete. Generally, the reaction time is about 0.5 to 100 hours. The target compound (1) is recovered by a conventional aqueous work-up from the reaction mixture. If necessary, compound (1) can be purified by an ordinary method such as distillation, chromatography or recrystallization. Alternatively, the reaction mixture may be purified directly or merely after filtering off the salt that has formed in the reaction, without undertaking the aqueous work-up.

Alternatively, some target compounds (1) of a certain structure can be obtained by addition reaction of nitrogen-containing heterocyclic compounds to cyclic ethers such as oxirane and oxetane, α,β-unsaturated carbonyl compounds such as acrylic acid esters and vinyl ketone, or cyclic carbonates.

The second method is by O-acylation or O-alkylation reaction of nitrogen-containing heterocyclic compounds having a hydroxyalkyl substituent group on N. This method is effective especially for the preparation of nitrogen-containing organic compounds having formulae (2) to (7) and (2') to (7'). The reaction is shown by the following scheme.

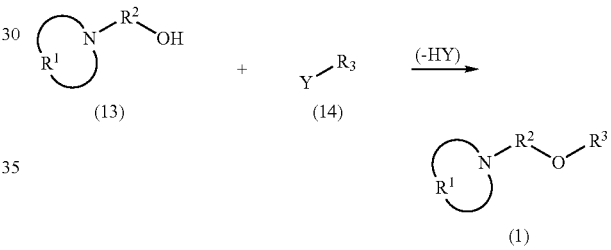

(1)

Herein $R^1$ is a straight, branched or cyclic divalent substituent group of 2 to 20 carbon atoms to form a nitrogen-containing heteroaliphatic or heteroaromatic ring with the nitrogen atom to which it is attached at both ends, which group may contain an oxygen, nitrogen, sulfur or halogen atom. $R^2$ is a straight or branched alkylene group of 2 to 10 carbon atoms which may contain a carbonyl group. $R^3$ is an alkyl or acyl group of 22 to 50 carbon atoms which may contain a hydroxyl, carbonyl, ester, ether or cyano group. Y is a leaving group such as a halogen atom, alkyl- or aryl-sulfonyloxy, hydroxyl, acyloxy, phenoxy or alkoxy group.

In the above reaction, compound (14) serving as an alkylating or acylating agent acts on a N-(hydroxyalkyl) nitrogen-containing heterocyclic compound (13), which may be prepared by the aforementioned method or the like, yielding the target compound (1). Compound (14) is an alkylating agent when $R^3$ is an alkyl group and an acylating agent when $R^3$ is an acyl group. An appropriate amount of compound (14) used is from 0.1 to 5.0 moles, especially from 0.3 to 2.0 moles per mole of the N-(hydroxyalkyl) nitrogen-containing heterocyclic compound (13). The reaction may be carried out in a solvent or in the absence of a solvent. Suitable solvents include hydrocarbons such as hexane, heptane, benzene, toluene and xylene; ethers such as diethyl ether, dibutyl ether, tetrahydrofuran, 1,4-dioxane and diglyme; chlorinated solvents such as methylene chloride, chloroform and 1,2-dichloroethylene; aprotic polar solvents such as N,N-dimethylformamide, N,N-dimethylacetamide, dimethyl sulfoxide and N-methylpyrrolidone; carboxylic acids such as formic acid and acetic acid; esters such as ethyl acetate and butyl acetate; ketones such as acetone and 2-butanone; nitriles such as acetonitrile; amines such as pyridine and triethylamine; alcohols such as methanol, ethanol, 2-propanol and t-butyl alcohol; and water. The solvent may be selected from the foregoing in accordance with the reaction conditions and used either singly or as mixtures thereof.

In order to promote the reaction, a basic compound may be added. Examples include, but are not limited to, salts of alkali or alkaline earth metals such as sodium hydroxide, potassium hydroxide, potassium carbonate, sodium carbonate, sodium hydrogen carbonate, sodium hydride, calcium hydride, potassium t-butoxide, and lithium t-butoxide; organometal compounds such as n-butyllithium, lithium diisopropylamide, lithium hexamethyldisilazide, and bromomagnesium diisopropylamide; and organic amines such as pyridine, triethylamine, diisopropylethylamine, N,N-dimethylaniline, and 4-dimethylaminopyridine. The basic compound may be used alone or in admixture. An appropriate amount of the basic compound used is from 0.8 to 10 moles, especially from 0.9 to 3.0 moles per mole of compound (14). The reaction temperature may be selected from a range of −70° C. to the reflux temperature of the solvent, preferably 0° C. to 50° C. In the event $R^3$=acyl and Y=alkoxy, compound (14) is a carboxylic acid ester, and the instant reaction is a transesterification reaction. In this event, the above-mentioned basic compound is used as a catalyst in an amount of 0.001 to 5.0 moles, especially 0.005 to 0.5 mole per mole of compound (14), and reaction is preferably carried out while distilling off the alcohol (Y—H) formed during the reaction. To maximize the final yield, it is desirable to monitor the progress of the reaction using gas chromatography (GC) or thin-layer chromatography (TLC) until the reaction is complete. Generally, the reaction time is about 0.2 to 20 hours. The target compound (1) is recovered by a conventional aqueous work-up from the reaction mixture. If necessary, compound (1) can be purified by an ordinary method such as distillation, chromatography or recrystallization. Alternatively, the reaction mixture may be purified directly or merely after filtering off the salt that has formed in the reaction, without undertaking the aqueous work-up.

Resist Composition

In a resist composition of the invention, the nitrogen-containing organic compound described above is formulated. In one preferred embodiment, the resist composition is a chemically amplified positive resist composition comprising:

(A) a nitrogen-containing organic compound having one of formulae (1) to (10) and (2') to (10'), (B) an organic solvent, (C) a base resin having an acid labile group-protected acidic functional group, which is alkali-insoluble or substantially alkali-insoluble, but becomes alkali-soluble when the acid labile group is deprotected, (D) a photoacid generator, and optionally, (E) a dissolution regulator.

In the resist composition, an appropriate amount of component (A) compounded is 0.01 to 10 parts by weight, desirably 0.05 to 5 parts by weight per 100 parts by weight of the base resin (C). Outside the range, less amounts of the nitrogen-containing compound may fail to achieve the desired effect whereas larger amounts may lower the sensitivity of the resist. Component (A) may be used alone or in admixture of two or more. Besides the nitrogen-containing organic compound defined herein, one or more of nitrogen-containing organic compounds commonly used as the quencher in prior art resist compositions may be used alone or in admixture.

Organic Solvent B

The organic solvent used herein may be any organic solvent in which the amine compound (A), base resin, photoacid generator, and other components are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the photoacid generator is most soluble therein.

An appropriate amount of the organic solvent used is about 200 to 1,000 parts, especially about 400 to 800 parts by weight per 100 parts by weight of the base resin.

Base Polymer C

The base polymers or resins used as component (C) in the inventive compositions include polyhydroxystyrene (PHS), and copolymers of hydroxystyrene with styrene, (meth)acrylic acid esters or other polymerizable olefinic compounds, for KrF excimer laser resist use; (meth)acrylic acid ester polymers, alternating copolymers of cycloolefin with maleic anhydride, copolymers further containing vinyl ethers or (meth)acrylic acid esters, polynorbornene, and ring-opening metathesis polymerized cycloolefins, for ArF excimer laser resist use; and fluorinated forms of the foregoing polymers (for both KrF and ArF laser uses) and polymers resulting from ring-closure polymerization using fluorinated dienes for $F_2$ laser resist use. Silicon-substituted forms of the foregoing polymers and polysilsesquioxane polymers are useful for the bilayer resists. The base resin is not limited to the polymers of these systems. The base polymers may be used alone or in admixture of two or more. In the case of positive resist compositions, it is a common practice to substitute acid labile groups for hydroxyl groups on phenol, carboxyl groups or fluorinated alkyl alcohols for reducing the rate of dissolution in unexposed regions.

The acid labile groups to be introduced into the base polymers may be selected from a variety of such groups, preferably from acetal groups of 2 to 30 carbon atoms and tertiary alkyl groups of 4 to 30 carbon atoms having the formulae (C1) and (C2), respectively.

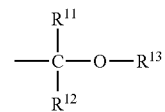

(C1)

-continued

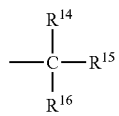
(C2)

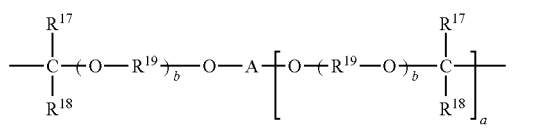
(C3a)

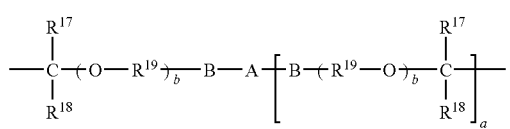
(C3b)

In formulae (C1) and (C2), $R^{11}$ and $R^{12}$ each are hydrogen or a straight, branched or cyclic alkyl group of 1 to 20 carbon atoms, preferably 1 to 12 carbon atoms, which may contain a hetero atom such as oxygen, sulfur, nitrogen or fluorine, $R^{13}$, $R^{14}$, $R^{15}$ and $R^{16}$ each are a straight, branched or cyclic alkyl group of 1 to 20 carbon atoms, preferably 1 to 12 carbon atoms, an aryl group or an aralkyl group, which may contain a hetero atom such as oxygen, sulfur, nitrogen or fluorine. A pair of $R^{11}$ and $R^{12}$, a pair of $R^{11}$ and $R^{13}$, a pair of $R^{12}$ and $R^{13}$, a pair of $R^{14}$ and $R^{15}$, a pair of $R^{14}$ and $R^{16}$, or a pair of $R^{15}$ and $R^{16}$, taken together, may form a ring of 3 to 20 carbon atoms, preferably 3 to 12 carbon atoms, with the carbon or oxygen atom to which they are attached.

Illustrative examples of the acetal group of formula (C1) include, but are not limited to, methoxymethyl, ethoxymethyl, propoxymethyl, butoxymethyl, isopropoxymethyl, t-butoxymethyl, neopentyloxymethyl, (1-methylcyclohexyl) methoxymethyl, 2-adamantyloxymethyl, (1-adamantyl) methoxymethyl, fenchyloxymethyl, (2-methyl-2-norbornyl) methoxymethyl, 1-methoxyethyl, 1-methoxypropyl, 1-methoxybutyl, 1-ethoxyethyl, 1-ethoxypropyl, 1-ethoxybutyl, 1-propoxyethyl, 1-propoxypropyl, 1-propoxybutyl, 1-cyclopentyloxyethyl, 1-cyclohexyloxyethyl, 2-methoxyisopropyl, 2-ethoxyisopropyl, 1-phenoxyethyl, 1-benzyloxyethyl, 1-phenoxypropyl, 1-benzyloxypropyl, 1-adamantyloxyethyl, 1-adamantyloxypropyl, 2-tetrahydrofuryl, 2-tetrahydro-2H-pyranyl, 1-(2-cyclohexanecarbonyloxyethoxy)ethyl, 1-(2-cyclohexanecarbonyloxyethoxy)propyl, 1-[2-(1-adamantylcarbonyloxy)ethoxy]ethyl, and 1-[2-(1-adamantylcarbonyloxy)ethoxy]propyl.

Illustrative examples of the tertiary alkyl group of formula (C2) include, but are not limited to, t-butyl, t-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$] dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

In the base resin, some hydrogen atoms of hydroxyl groups may be substituted with acid labile groups of the following general formula (C3a) or (C3b) for crosslinkage between molecules or within a molecule.

Herein, $R^{17}$ and $R^{18}$ each are hydrogen or a straight, branched or cyclic alkyl group of 1 to 8 carbon atoms, or $R^{17}$ and $R^{18}$, taken together, may form a ring with the carbon atom to which they are attached, with the proviso that each of $R^{17}$ and $R^{18}$ is a straight or branched alkylene group of 1 to 8 carbon atoms when they form a ring. $R^{19}$ is a straight, branched or cyclic alkylene group of 1 to 10 carbon atoms. Letter "a" is an integer of 1 to 7, and "b" is 0 or an integer of 1 to 10. "A" is a (a+1)-valent aliphatic or alicyclic saturated hydrocarbon group, aromatic hydrocarbon group or heterocyclic group of 1 to 50 carbon atoms, which may have an intervening hetero atom and in which the hydrogen atom attached to a carbon atom may be partially replaced by a hydroxyl group, carboxyl group, carbonyl group or fluorine atom. B is —CO—O—, —NHCO—O— or —NHCONH—.

Illustrative examples of the crosslinking acetal linkages represented by formulae (C3a) and (C3b) are given below as (C3)-1 through (C3)-8, but not limited thereto.

(C3)-1

—CH(CH$_3$)—O—CH$_2$CH$_2$—O—CH(CH$_3$)—

(C3)-2

—CH(CH$_3$)—O—⟨cyclohexyl⟩—O—CH(CH$_3$)—

(C3)-3

—CH(CH$_3$)—O—CH$_2$CH$_2$CH$_2$CH$_2$—O—CH(CH$_3$)—

(C3)-4

—CH(CH$_3$)—O—CH$_2$CHOCH$_2$CH$_2$OCH$_2$CH$_2$—O—CH(CH$_3$)—

(C3)-5

—CH(CH$_3$)—O—CH$_2$CH$_2$O—⟨phenyl⟩—OCH$_2$CH$_2$—O—CH(CH$_3$)—

(C3)-6

—CH(CH$_3$)—O—CH$_2$CH$_2$O—⟨furyl⟩—OCH$_2$CH$_2$—O—CH(CH$_3$)—

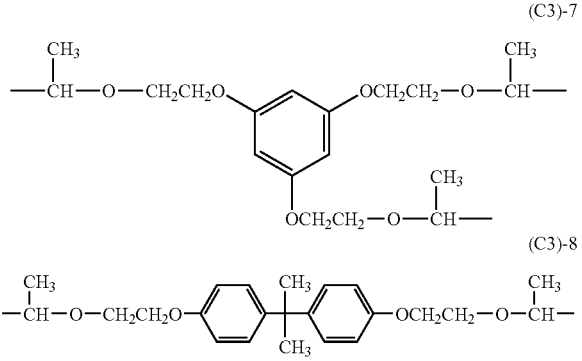

Preferably the base polymer has a weight average molecular weight (Mw) of 2,000 to 100,000 as determined by gel permeation chromatography (GPC) using polystyrene standards. With Mw below 2,000, film formation and resolution may become poor. With Mw beyond 100,000, resolution may become poor or foreign matter may generate during pattern formation.

Acid Generator D

In the resist composition, an photoacid generator is typically added as acid generator (D). It may be any compound capable of generating an acid upon exposure to high-energy radiation such as UV, deep UV, electron beam, EUV, x-ray, excimer laser beam, gamma-ray or synchrotron radiation. Suitable photoacid generators include sulfonium salts, iodonium salts, sulfonyldiazomethane, N-sulfonyloxydicarboxylmide, O-arylsulfonyloxime and O-alkylsulfonyloxime photoacid generators. Exemplary photoacid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 4-methylphenyldiphenylsulfonium, 4-tert-butylphenylsulfonium, bis(4-methylphenyl)phenylsulfonium, bis(4-tert-butylphenyl)phenylsulfonium, tris(4-methylphenyl)sulfonium, tris(4-tert-butylphenyl)sulfonium, tris(phenylmethyl)sulfonium, 2-naphthyldiphenylsulfonium, dimethyl(2-naphthyl)sulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxopropylthiacyclopentanium, 2-oxobutylthiacyclopentanium, 2-oxo-3,3-dimethylbutylthiacyclopentanium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations include diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8- yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Exemplary bis(substituted alkylsulfonyl)imides include bis(trifluoromethylsulfonyl)imide, bis(pentafluoroethylsulfonyl)imide, bis(heptafluoropropylsulfonyl)imide, and perfluoro(1,3-propylenebissulfonyl)imide. A typical tris(substituted alkylsulfonyl)methide is tris(trifluoromethylsulfonyl)methide. Iodonium salts based on combination of the foregoing examples are included.

Exemplary sulfonyldiazomethane compounds include bissulfonyldiazomethane compounds and sulfonylcarbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(4-acetyloxyphenylsulfonyl)diazomethane, bis(4-(methanesulfonyloxy)phenylsulfonyl)diazomethane, bis(4-(p-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)-diazomethane, bis(2-naphthylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxydicarboxylmide photoacid generators include combinations of imide skeletons with sulfonates. Exemplary imide skeletons are succinimide, naphthalenedicarboximide, phthalimide, cyclohexyldicarboximide, 5-norbornene-2,3-dicarboximide, and 7-oxabicyclo[2.2.1]-5-heptene-2,3-dicarboximide. Exemplary sulfonates include trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tbsyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucin, catechol, resorcinol, and hydroquinone, in which all the hydroxyl groups are substituted by trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, heptafluoropropanesulfonate, nonafluorobutanesulfonate, tridecafluorohexanesulfonate, perfluoro(4-ethylcyclohexane)sulfonate, heptadecafluorooctanesulfonate, 2,2,2-trifluoroethanesulfonate, pentafluorobenzenesulfonate, 4-(trifluoromethyl)benzenesulfonate, 4-fluorobenzenesulfonate, mesitylenesulfonate, 2,4,6-triisopropylbenzenesulfonate, toluenesulfonate, benzenesulfonate, 4-(p-toluenesulfonyloxy)benzenesulfonate, 6-(p-toluenesulfonyloxy)naphthalene-2-sulfonate, 4-(p-toluenesulfonyloxy)naphthalene-1-sulfonate, 5-(p-toluenesulfonyloxy)naphthalene-1-sulfonate, 8-(p-toluenesulfonyloxy)naphthalene-1-sulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Suitable O-arylsulfonyloxime compounds and O-alkylsulfonyloxime compounds (oxime sulfonates) include photoacid generators in the form of glyoxime derivatives, oxime sulfonates with a long conjugated system separated by thiophene or cyclohexadiene, oxime sulfonates having an electron withdrawing group such as trifluoromethyl incorporated for increased stability, oxime sulfonates using phenylacetonitrile or substituted acetonitrile derivatives, and bisoxime sulfonates.

Photoacid generators in the form of glyoxime derivatives include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedionedioxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(4-fluorobenzenesulfonyl)-α-dimethylglyoxime, bis-O-(4-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(4-fluorobenzenesulfonyl)-nioxime, bis-O-(4-trifluoromethylbenzenesulfonyl)-nioxime, and bis-O-(xylenesulfonyl)-nioxime. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Photoacid generators in the form of oxime sulfonates with a long conjugated system separated by thiophene or cyclohexadiene include (5-(p-toluenesulfonyl)oxyimino-5H-thiophen-2-ylidene)phenyl-acetonitrile, (5-(10-camphorsulfonyl)oxyimino-5H-thiophen-2-ylidene)phenyl-acetonitrile, (5-n-octanesulfonyloxyimino-5H-thiophen-2-ylidene)phenyl-acetonitrile, (5-(p-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methyl-phenyl)acetonitrile, (5-(4-(p-toluenesulfonyloxy)benzenesulfonyl)oxyimino-5H-thiophen-2-ylidene)phenylacetonitrile, and (5-(2,5-bis(p-toluenesulfonyloxy)benzenesulfonyl)oxyimino-5H-thiophen-2-ylidene)phenylacetonitrile. Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1, 1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl) difluoromethanesulfonate, and 4-oxo-1-adamantyloxycarbonyldifluoromethanesulfonate.

Suitable acid generators in the form of oxime sulfonates having an electron withdrawing group such as trifluoromethyl incorporated for increased stability include 2,2,2-trifluoro-1-phenyl-ethanone O-(methylsulfonyl)oxime, 2,2,2-trifluoro-1-phenyl-ethanone O-(10-camphorsulfonyl)oxime, 2,2,2-trifluoro-1-phenylethanone O-(4-methoxybenzenesulfonyl)oxime, 2,2,2-trifluoro-1-phenylethanone O-(1-naphthylsulfonyl)oxime, 2,2,2-trifluoro-1-phenylethanone O-(2-naphthylsulfonyl)oxime, 2,2,2-trifluoro-1-phenylethanone O-(2,4,6-trimethylphenyl-sulfonyl)oxime, 2,2,2-trifluoro-1-(4-methylphenyl)ethanone O-(10-camphor-sulfonyl)oxime, 2,2,2-trifluoro-1-(4-methylphenyl)ethanone O-(methyl-sulfonyl)oxime, 2,2,2-trifluoro-1-(2-methylphenyl)ethanone O-(10-camphor-sulfonyl)oxime, 2,2,2-trifluoro-1-(2,4-dimethylphenyl)ethanone O-(10-camphor-sulfonyl)oxime, 2,2,2-trifluoro-1-(2,4-dimethylphenyl)ethanone O-(1-naphthyl-sulfonyl)oxime, 2,2,2-trifluoro-1-(2,4-dimethylphenyl)-ethanone O-(2-naphthylsulfonyl)oxime, 2,2,2-trifluoro-1-(2,4,6-trimethylphenyl)ethanone O-(10-camphorsulfonyl)oxime, 2,2,2-trifluoro-1-(2,4,6-trimethylphenyl)ethanone O-(1-naphthylsulfonyl)oxime, 2,2,2-trifluoro-1-(2,4,6-trimethylphenyl)ethanone O-(2-naphthylsulfonyl)oxime, 2,2,2-trifluoro-1-(4-methoxyphenyl)ethanone O-(methyl-sulfonyl)oxime, 2,2,2-trifluoro-1-(4-methylthiophenyl)-ethanone O-(methyl-sulfonyl)oxime, 2,2,2-trifluoro-1-(3,4-dimethoxyphenyl)ethanone O-(methyl-sulfonyl)oxime, 2,2,2-trifluoro-1-(4-methoxyphenyl)ethanone O-(4-methyl-phenylsulfonyl)oxime, 2,2,2-trifluoro-1-(4-methoxyphenyl)ethanone O-(4-methoxyphenylsulfonyl)oxime, 2,2,2-trifluoro-1-(4-methoxyphenyl)ethanone O-(4-dodecyl-phenylsulfonyl)oxime, 2,2,2-trifluoro-1-(4-methoxyphenyl)ethanone O-(octyl-sulfonyl)oxime, 2,2,2-trifluoro-1-(4-thiomethylphenyl)ethanone O-(4-methoxy-phenylsulfonyl)oxime, 2,2,2-trifluoro-1-(4-thiomethylphenyl)ethanone O-(4-dodecyl-phenylsulfonyl)oxime, 2,2,2-trifluoro-1-(4-thiomethylphenyl)ethanone O-(octyl-sulfonyl)oxime, 2,2,2-trifluoro-1-(4-thiomethylphenyl)ethanone O-(2-naphthyl-sulfonyl)oxime, 2,2,2-trifluoro-1-(2-methylphenyl)ethanone O-(methyl-sulfonyl) oxime, 2,2,2-trifluoro-1-(4-methylphenyl)ethanone O-(phenyl-sulfonyl)oxime, 2,2,2-trifluoro-1-(4-chlorophenyl)ethanone O-(phenyl-sulfonyl)oxime, 2,2,3,3,4,4,4-heptafluoro-1-phenylbutanone O-(10-camphor-sulfonyl)oxime, 2,2,2-trifluoro-1-(1-naphthyl)ethanone O-(methylsulfonyl)-oxime, 2,2,2-trifluoro-1-(2-naphthyl)ethanone O-(methyl-sulfonyl)-oxime, 2,2,2-trifluoro-1-(4-benzylphenyl)ethanone O-(methyl-sulfonyl)oxime, 2,2,2-trifluoro-1-(4-(phenyl-1,4-dioxa-but-1-yl)phenyl)-ethanone O-(methylsulfonyl)oxime, 2,2,2-trifluoro-1-(1-naphthyl) ethanone O-(propylsulfonyl)-oxime, 2,2,2-trifluoro-1-(2-naphthyl)ethanone O-(propylsulfonyl)-oxime, 2,2,2-trifluoro-1-(4-benzylphenyl)ethanone O-(propyl-sulfonyl) oxime, 2,2,2-trifluoro-1-(4-methylsulfonylphenyl)ethanone O-(propyl-sulfonyl)oxime, 2,2,2-trifluoro-1-(4-methylsulfonyloxyphenyl)ethanone O-(propylsulfonyl)oxime, 2,2,2-trifluoro-1-(4-methylcarbonyloxyphenyl)ethanone O-(propyl-sulfonyl)oxime, 2,2,2-trifluoro-1-(6H,7H-5,8-dioxonaphth-2-yl)ethanone O-(propylsulfonyl)oxime, 2,2,2-trifluoro-1-(4-methoxycarbonylmethoxyphenyl)ethanone O-(propylsulfonyl)oxime, 2,2,2-trifluoro-1-(4-methoxycarbonyl)-(4-amino-1-oxa-pent-1-yl)phenyl)ethanone O-(propylsulfonyl)oxime, 2,2,2-trifluoro-1-(3,5-dimethyl-4-ethoxyphenyl)ethanone O-(propylsulfonyl)oxime, 2,2,2-trifluoro-1-(4-benzyloxyphenyl)ethanone O-(propyl-sulfonyl)oxime, 2,2,2-trifluoro-1-(2-thiophenyl)ethanone O-(propylsulfonate)-oxime, and 2,2,2-trifluoro-1-(1-dioxathiophen-2-yl) ethanone O-(propyl-sulfonate)oxime; 2,2,2-trifluoro-1-(4-(3-(4-(2,2,2-trifluoro-1-(trifluoro-methanesulfonyloxyimino)ethyl)phenoxy)propoxy)phenyl) ethanone O-(trifluoromethanesulfonyl)oxime, 2,2,2-trifluoro-1-(4-(3-(4-(2,2,2-trifluoro-1-(1-propane-sulfonyloxyimino)ethyl)phenoxy)propoxy)phenyl)ethanone O-(propylsulfonyl oxime, 2,2,2-trifluoro-1-(4-(3-(4-(2,2,2-trifluoro-1-(1-butane-sulfonyloxyimino)ethyl)phenoxy)propoxy)phenyl)ethanone O-(butylsulfonyl)oxime, 2,2,2-trifluoro-1-(4-(3-(4-(2,2,2-trifluoro-1-(4-(4-methyl-phenylsulfonyloxy)phenylsulfonyloxyimino)ethyl) phenoxy)-propoxy)phenyl)ethanone O-(4-(4-methylphenylsulfonyloxy)-phenylsulfonyl)oxime, and 2,2,2-trifluoro-1-(4-(3-(4-(2,2,2-trifluoro-1-(2,5-bis(4-methylphenylsulfonyloxy)benzenesulfonyloxy) phenylsulfonyloxy-imino)ethyl)phenoxy)propoxy)phenyl) ethanone O-(2,5-bis(4-methylphenylsulfonyloxy) benzenesulfonyloxy)phenylsulfonyl)-oxime.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxy-carbonyl) difluoromethanesulfonate, and 4-oxo-1-adamantyloxycarbonyldifluoromethanesulfonate.

Also included are oxime sulfonates having the formula (Ox-1):

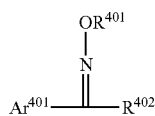
(Ox-1)

wherein R⁴⁰¹ is a substituted or unsubstituted $C_1$-$C_{10}$ haloalkylsulfonyl or halobenzenesulfonyl group, $R^{402}$ is a $C_1$-$C_{11}$ haloalkyl group, and $Ar^{401}$ is substituted or unsubstituted aromatic or hetero-aromatic group.

Examples include 2-[2,2,3,3,4,4,5,5-octafluoro-1-(nonafluorobutylsulfonyloxy-imino)pentyl]fluorene, 2-[2,2,3,3,4,4-pentafluoro-1-(nonafluorobutylsulfonyloxy-imino)butyl]fluorene, 2-[2,2,3,3,4,4,5,5,6,6-decafluoro-1-(nonafluorobutylsulfonyl-oxyimino)hexyl]fluorene, 2-[2,2,3,3,4,4,5,5-octafluoro-1-(nonafluorobutylsulfonyloxy-imino)pentyl]-4-biphenyl, 2-[2,2,3,3,4,4-pentafluoro-1-(nonafluorobutylsulfonyloxy-imino)butyl]-4-biphenyl, and 2-[2,2,3,3,4,4,5,5,6,6-decafluoro-1-(nonafluorobutylsulfonyl-oxyimino)hexyl]-4-biphenyl. Also included are modified forms of the foregoing compounds having substituted on their skeleton 2-benzoyloxy-1,1,3,3,3-pentafluoropropane-sulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Suitable oxime sulfonate generators using substituted acetonitrile derivatives include α-(p-toluenesulfonyloxy-imino)-phenylacetonitrile, α-(p-chlorobenzenesulfonyloxy-imino)-phenylacetonitrile, α-(4-nitrobenzenesulfonyloxy-imino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylaceto-nitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]aceto-nitrile, γ-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile.

Also included are modified forms of the foregoing compounds having substituted on their skeleton 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-(1-adamantanecarbonyloxy)-1,1,3,3,3-pentafluoropropane-sulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, 1,1-difluoro-2-tosyloxyethanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)

Suitable bisoxime sulfonates include bis(α-(p-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(trifluoromethanesulfonyloxy)imino)-p-phenylenediaceto-nitrile, bis(α-(4-methoxybenzenesulfonyloxy)imino)-p-phenylenediaceto-nitrile, bis(α-(p-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediaceto-nitrile, bis(α-(10-camphorsulfonyloxy)imino)-m-phenylenediaceto-nitrile, bis(α-(trifluoromethanesulfonyloxy)imino)-m-phenylenediaceto-nitrile, bis(α-(4-methoxybenzenesulfonyloxy)imino)-m-phenylenediaceto-nitrile, etc.

difluoromethanesulfonate, and 4-oxo-1-adamantyloxycarbonyldifluoromethanesulfonate.

When the photoacid generator (D) is added to the KrF excimer laser resist composition, preference is given to sulfonium salts, bissulfonyldiazomethanes, N-sulfonyloxyimides and oxime-O-sulfonates. Illustrative preferred photoacid generators include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(p-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(p-toluenesulfonyl-oxy)benzenesulfonate, 4-tert-butylphenyldiphenylsulfonium camphorsulfonate, tris(4-methylphenyl)sulfonium camphorsulfonate, tris(4-tert-butylphenyl)sulfonium camphorsulfonate, bis(tert-butylsulfonyl)diazomethane, bis(cyclohexylsulfonyl)diazomethane, bis(2,4-dimethylphenylsulfonyl)diazomethane, bis(4-n-hexyloxyphenylsulfonyl)diazomethane, bis(2-methyl-4-n-hexyloxyphenylsulfonyl)diazomethane, bis(2,5-dimethyl-4-n-hexyloxyphenylsulfonyl)diazomethane, bis(3,5-dimethyl-4-n-hexyloxyphenylsulfonyl)diazomethane, bis(2-methyl-5-isopropyl-4-n-hexyloxy)phenylsulfonyldiazo-methane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, (5-(10-camphorsulfonyl)oxyimino-5H-thiophen-2-ylidene)(2-methylphenyl)acetonitrile, and (5-(p-toluenesulfonyl)oxyimino-5H-thiophen-2-ylidene)(2-methylphenyl)acetonitrile.

When the photoacid generator (D) is added to the ArF laser resist composition, preference is given to sulfonium salts and oxime-O-sulfonates. Illustrative preferred photoacid generators include triphenylsulfonium trifluoromethanesulfonate, triphenylsulfonium pentafluoroethanesulfonate, triphenylsulfonium heptafluoropropanesulfonate, triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutane-sulfonate, 4-tert-butylphenyldiphenylsulfonium nonafluorobutanesulfonate, 4-tert-butylphenyldiphenylsulfonium perfluoro(4-ethylcyclo-hexane)sulfonate, 4-tert-butylphenyldiphenylsulfonium heptafluorooctane-sulfonate, triphenylsulfonium 1,1-difluoro-2-naphthylethanesulfonate, triphenylsulfonium 1,1,2,2-tetrafluoro-2-(norbornan-2-yl)ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)-propanesulfonate, triphenylsulfonium 2-(cyclohexanecarbonyloxy)-1,1,3,3,3-pentafluoropropanesulfonate, triphenylsulfonium 2-(2-naphthoyloxy)-1,1,3,3,3-pentafluoro-propanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropane-sulfonate, triphenylsulfonium adamantanemethoxycarbonyldifluoromethane-sulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyloxy)-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyl-oxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoro-methanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyl-oxy-1,1,3,3,3-pentafluoropropanesulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyl-oxyimino)pentyl)fluorene, 2-(2,2,3,3,4,4-pentafluoro-1-(nonafluorobutylsulfonyloxyimino)butyl)fluorene, 2-(2,2,3,3,4,4,5,5,6,6-decafluoro-1-(nonafluorobutylsulfonyl-oxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecarbonyloxy)-1,1,3,3,3-pentafluoropropanesulfonyloxyimino)butyl)fluorene, and 2-(2,2,3,3,4,4,5,5,6,6-decafluoro-1-(nonafluorobutyl-sulfonyloxyimino)hexyl)fluorene.

When the photoacid generator (D) is added to the ArF immersion lithography resist composition, preference is given to sulfonium salts and oxime-O-sulfonates. Illustrative preferred photoacid generators include triphenylsulfonium nonafluorobutanesulfonate, triphenylsulfonium tridecafluorohexanesulfonate, triphenylsulfonium heptadecafluorooctanesulfonate, triphenylsulfonium perfluoro(4-ethylcyclohexane)sulfonate, 4-methylphenyldiphenylsulfonium nonafluorobutanesulfonate, 2-oxo-2-phenylethylthiacyclopentanium nonafluorobutane-sulfonate, 4-tert-butylphenyldiphenylsulfonium nonafluorobutanesulfonate, 4-tert-butylphenyldiphenylsulfonium perfluoro(4-ethylcyclo-hexane)sulfonate, 4-tert-butylphenyldiphenylsulfonium heptafluorooctane-sulfonate, triphenylsulfonium 1,1-difluoro-2-naphthylethanesulfonate, triphenylsulfonium 1,1,2,2-tetrafluoro-2-(norbornan-2-yl)-ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)-propanesulfonate, triphenylsulfonium 2-(cyclohexanecarbonyloxy)-1,1,3,3,3-pentafluoropropanesulfonate, triphenylsulfonium 2-(2-naphthoyloxy)-1,1,3,3,3-pentafluoro-propanesulfonate, triphenylsulfonium 2-(1-adamantanecarbonyloxy)-1,1,3,3,3-pentafluoropropanesulfonate, triphenylsulfonium 2-hydroxy-1,1,3,3,3-pentafluoropropane-sulfonate, triphenylsulfonium adamantanemethoxycarbonyldifluoromethane-sulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-(cyclohexanecarbonyl-oxy)-1,1,3,3,3-pentafluoropropanesulfonate, 4-tertbutylphenyldiphenylsulfonium 2-(2-naphthoyloxy)-1,1,3,3,3-pentafluoropropanesulfonate, 4-tert-butylphenyldiphenylsulfonium 2-(1-adamantanecarbonyloxy)-1,1,3,3,3-pentafluoropropanesulfonate, 4-tert-butylphenyldiphenylsulfonium 2-hydroxy-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyl-adamantane)methoxycarbonyldifluoromethanesulfonate, 4-tert-butylphenyldiphenylsulfonium methoxycarbonyldifluoro-methanesulfonate, 2-oxo-2-phenylethylthiacyclopentanium 2-benzoyloxy-1,1,3,3,3-pentafluoropropane-sulfonate, 2-oxo-2-phenylethylthiacyclopentanium 2-cyclohexanecarbonyl-oxy-1,1,3,3,3-pentafluoropropane-sulfonate, triphenylsulfonium perfluoro(1,3-propylenebissulfonyl)imide, triphenylsulfonium bis(pentafluoroethylsulfonyl)imide, 2-(2,2,3,3,4,4,5,5-octafluoro-1-(nonafluorobutylsulfonyloxy-imino)pentyl)fluorene, 2-(2,2,3,3,4,4-pentafluoro-1-(nonafluorobutylsulfonyloxy-imino)butyl)fluorene, 2-(2,2,3,3,4,4,5,5,6,6-decafluoro-1-(nonafluorobutylsulfonyl-oxyimino)hexyl)fluorene, 2-(2,2,3,3,4,4,5,5-octafluoro-1-(2-(cyclohexanecarbonyloxy)-1,1,3,3,3-pentafluoropropanesulfonyloxyimino)pentyl)fluorene, 2-(2,2,3,3,4,4-pentafluoro-1-(2-(cyclohexanecarbonyloxy)-1,1,3,3,3-pentafluoropropanesulfonyloxyimino)butyl)fluorene, and 2-(2,2,3,3,4,4,5,5,6,6-decafluoro-1-(nonafluorobutyl-sulfonyloxyimino)hexyl)fluorene.

In the chemically amplified resist composition, the photoacid generator (D) may be added in any desired amount as long as the objects of the invention are not compromised. An appropriate amount of the photoacid generator (D) is 0.1 to 10 parts, and more preferably 0.1 to 5 parts by weight per 100 parts by weight of the base resin in the composition. Too high a proportion of the photoacid generator (D) may give rise to problems of degraded resolution and foreign matter upon development and resist film peeling. The photoacid generators (D) may be used alone or in admixture of two or more. The transmittance of the resist film can be controlled by using an photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

In the resist composition of the invention, there may be added a compound which is decomposed with an acid to generate another acid, that is, acid amplifier compound. For these compounds, reference should be made to J. Photopolym. Sci. and Tech., 8, 43-44, 45-46 (1995), and ibid., 9, 29-30 (1996).

Examples of the acid amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition of the invention, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Dissolution Regulator E

The dissolution regulator which can be added to the resist composition is a compound having on the molecule at least two phenolic hydroxyl groups, in which an average of from 0 to 100 mol % of all the hydrogen atoms on the phenolic hydroxyl groups are replaced by acid labile groups or a compound having on the molecule at least one carboxyl group, in which an average of 50 to 100 mol % of all the hydrogen atoms on the carboxyl groups are replaced by acid labile groups, both the compounds having a molecular weight (weight average molecular weight in the case of D8 and D9) within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having at least one carboxyl group include those of formulas (D1) to (D14) below.

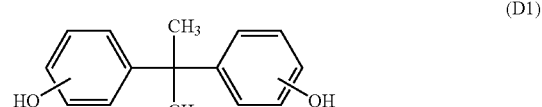

(D1)

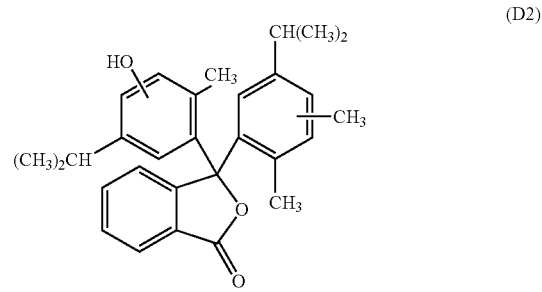

(D2)

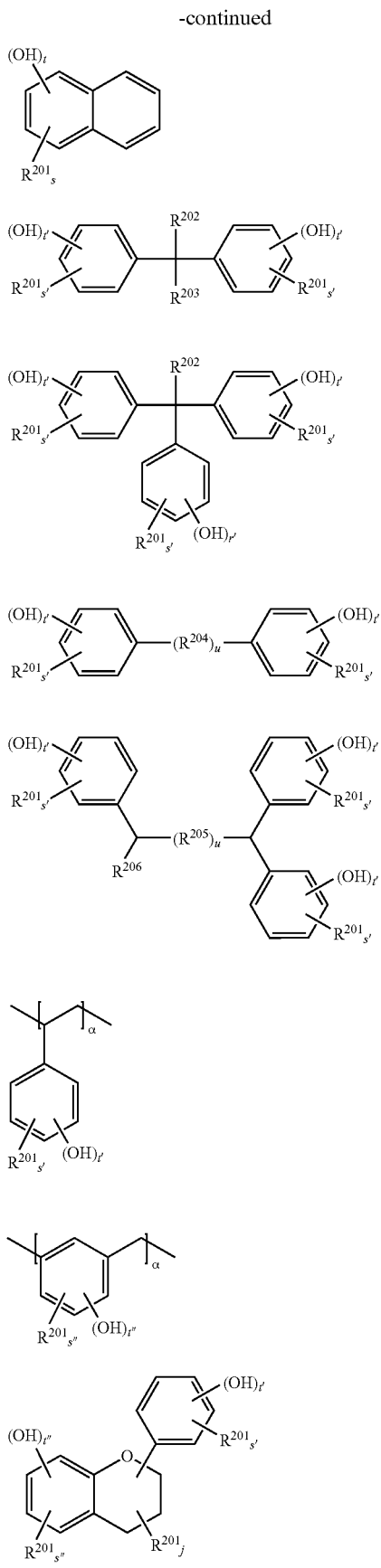
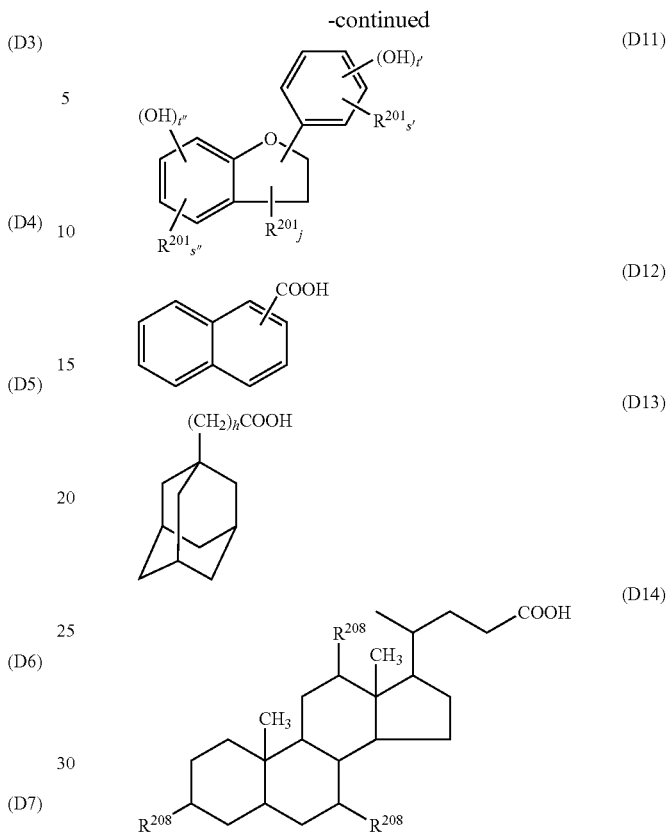

In these formulas, $R^{201}$ and $R^{202}$ are each hydrogen or a straight or branched $C_1$-$C_8$ alkyl or alkenyl group. $R^{203}$ is hydrogen, a straight or branched $C_1$-$C_8$ alkyl or alkenyl group, or —$(R^{207})_h$—COOH. $R^{204}$ is —$(CH_2)_i$— wherein i=2 to 10, $C_6$-$C_{10}$ arylene, carbonyl, sulfonyl, an oxygen atom, or a sulfur atom. $R^{205}$ is a $C_1$-$C_{10}$ alkylene, a $C_6$-$C_{10}$ arylene, carbonyl, sulfonyl, an oxygen atom, or a sulfur atom. $R^{206}$ is hydrogen, a straight or branched $C_1$-$C_8$ alkyl or alkenyl group, or a phenyl or naphthyl group having hydroxyl substituted thereon. $R^{207}$ is a straight or branched $C_1$-$C_{10}$ alkylene group. $R^{208}$ is hydrogen or hydroxyl. The letter j is an integer from 0 to 5; u and h are each 0 or 1; s, t, s', t', s", and t" are each numbers which satisfy s+t=8, s'+t'=5, and s"+t"=4, and are such that each phenyl skeleton has at least one hydroxyl group; and α is a number such that the compounds of formula (D8) or (D9) have a weight average molecular weight of from 100 to 1,000.

The dissolution regulator may be formulated in an amount of 0 to 50 parts, preferably 5 to 50 parts, and more preferably 10 to 30 parts by weight, per 100 parts by weight of the base resin, and may be used singly or as a mixture of two or more thereof. Less amounts of the dissolution regulator may fail to achieve improvement in resolution whereas too much amounts may cause a slimming of the patterned film and reduce the resolution.

In another embodiment, the resist composition of the invention is negative. The chemically amplified negative resist composition of the invention is typically defined as comprising:

(A) a nitrogen-containing organic compound having one of formulae (1) to (10) and (2') to (10'), (B) an organic solvent,
(C') a base resin which is alkali-soluble, but becomes substantially alkali-insoluble when crosslinked with a crosslinker,
(D) an acid generator, and
(F) a crosslinker for inducing crosslinkage under the action of an acid.

Components (A), (B) and (D) are the same as in the positive embodiment. Component (C') should be a base resin which is alkali-soluble, but becomes substantially alkali-insoluble when crosslinked with the crosslinker (F). Preferred are those resins among the resins exemplified as component (C) in the positive resist compositions which have a high proportion of unprotected alkali-soluble groups so that they are alkali soluble.

The acid crosslinkers useful as component (F) include compounds having at least two hydroxymethyl, alkoxymethyl, epoxy or vinyl ether groups in a molecule. Substituted glycoluril derivatives, urea derivatives, and hexa(methoxymethyl)melamine compounds are suitable. Examples include N,N,N',N'-tetramethoxymethylurea, hexamethoxymethylmelamine, tetraalkoxymethyl-substituted glycoluril compounds such as tetrahydroxymethyl-substituted glycoluril and tetramethoxymethylglycoluril, and condensates of phenolic compounds such as substituted or unsubstituted bis(hydroxymethylphenol) compounds and bisphenol A with epichlorohydrin. Especially preferred acid crosslinkers include 1,3,5,7-tetraalkoxymethylglycolurils such as 1,3,5,7-tetramethoxymethylglycoluril, as well as 1,3,5,7-tetrahydroxymethylglycoluril, 2,6-dihydroxymethyl-p-cresol, 2,6-dihydroxymethylphenol, 2,2',6,6'-tetrahydroxymethylbisphenol A, 1,4-bis[2-(2-hydroxypropyl)]benzene, N,N,N',N'-tetramethoxymethylurea, and hexamethoxymethylmelamine.

An appropriate amount of the crosslinker is, but not limited thereto, about 1 to 25 parts, and especially about 5 to 20 parts by weight per 100 parts by weight of the base resin in the resist composition. The crosslinkers may be used alone or in admixture of any.

In the resist composition of the invention, there may be added a surfactant which is commonly used for improving the coating characteristics. It may be added in conventional amounts so long as this does not compromise the objects of the invention. Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

Also, if desired, other components including acidic compounds, dyes, thermal crosslinkers, and stabilizers may be added to the resist composition of the invention.

Using the resist composition of the invention, patterns may be formed by any known lithographic technique. Typically, the composition is applied onto a substrate (e.g., Si, $SiO_2$, SiN, SiON, TiN, WSi, BPSG, SOG, organic antireflective coating, Cr, CrO, CrON, MoSi, etc.) for IC microfabrication by a suitable coating technique such as spin coating, roll coating, flow coating, dip coating, spray coating or doctor coating. The coating is prebaked on a hot plate at a temperature of 60 to 150° C. for about 0.1 to 10 minutes, preferably 80 to 140° C. for 0.5 to 5 minutes. The resulting resist film is generally 0.05 to 2.0 μm thick. A patterning mask having the desired pattern is placed over the resist film, and the resist film is then exposed to radiation, preferably having an exposure wavelength of up to 300 nm, such as UV, deep-UV, extremely short UV, excimer laser light, electron beam, x-ray, γ-ray and synchrotron radiation. The exposure dose is preferably in the range of about 1 to 200 $mJ/cm^2$, more preferably about 10 to 100 $mJ/cm^2$. Light exposure may be done by a conventional exposure process or in some cases, by an immersion lithography process of providing a liquid fill, typically water, between the projection lens and the resist. In the case of immersion lithography, if necessary, a topcoat may be applied onto the resist film before exposure, which is generally know as "top coat process." The resist film is then post-exposure baked (PEB) on a hot plate at 60 to 150° C. for 0.1 to 5 minutes, and preferably at 80 to 140° C. for 0.5 to 3 minutes. Finally, development may be carried out using as the developer an aqueous alkali solution, such as 0.1 to 5 wt %, and preferably 2 to 3 wt %, tetramethylammonium hydroxide (TMAH), this being done by a conventional method such as dip, puddle, or spray technique for a period of 0.1 to 3 minutes, and preferably 0.5 to 2 minutes. These steps result in the formation of the desired pattern on the substrate. If necessary, the pattern as developed can be adjusted in size by heat treatment which is known as "thermal flow" or by chemical shrink treatment. Of the various types of high-energy radiation that may be used, the resist composition of the invention is best suited to micro-pattern formation with, in particular, deep-UV rays having a wavelength of 260 to 120 nm or excimer laser beams, extremely short UV, x-rays or electron beams.

EXAMPLE

Examples of the invention are given below by way of illustration and not by way of limitation. The abbreviation IR denotes infrared absorption spectroscopy, $^1$H-NMR denotes proton nuclear magnetic resonance spectroscopy, and SEM is a scanning electron microscope. PGMEA is propylene glycol monomethyl ether acetate.

Synthesis Examples

Nitrogen-containing organic compounds within the scope of the invention were synthesized by the method described below.

Synthesis Example 1

Synthesis of [2-(1H-imidazol-1-yl)-1-methylethyl] behenate (Quencher 1)

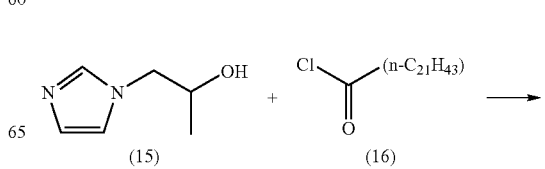

-continued

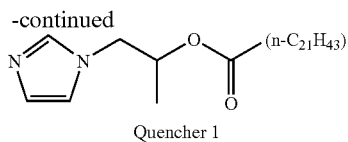

Quencher 1

With ice cooling and stirring, 35.9 g of behenic chloride (16) was added to a mixture of 12.6 g of 1-(1H-imidazol-1-yl)-2-propanol (15) and 50 g of dimethylformamide. Then the mixture was stirred at room temperature for 2 hours. Toluene was added to the solution, followed by neutralization. Subsequent standard aqueous work-up and purification by column chromatography gave 41.3 g of [2-(1H-imidazol-1-yl)-1-methylethyl] behenate (Quencher 1). Yield 92%.

Synthesis Example 2

Synthesis of (2-morpholinoethyl) behenate (Quencher 2)

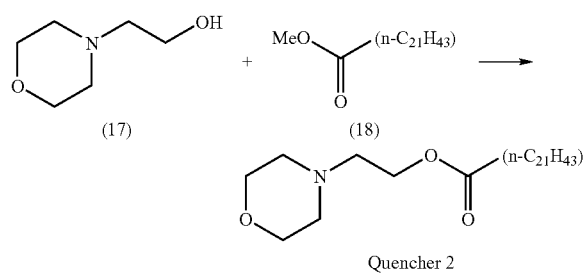

Quencher 2

A mixture of 35.5 g of methyl behenate (18), 19.7 g of 2-morpholinoethanol (17), 270 mg of sodium methoxide and 150 g of toluene was heated under reflux for 6 hours while distilling off the methanol resulting from the reaction. The reaction solution was cooled. By standard aqueous work-up and distilling off toluene, 41.3 g of (2-morpholinoethyl) behenate (Quencher 2) was obtained (yield 91%).

The target compound thus obtained was analyzed by IR and $^1$H-NMR spectroscopy.

IR (KBr): ν=2917, 2850, 1739, 1467, 1172, 1116 cm$^{-1}$
$^1$H-NMR (600 MHz in CDCl$_3$): δ=0.85 (3H, t, J=7.1 Hz), 1.20-1.3 (36H, m), 1.59 (2H, tt, J=7.6, 7.3 Hz), 2.28 (2H, t, J=7.6 Hz), 2.50 (4H, m), 2.61 (2H, br.t, J=5.9 Hz), 3.69 (4H, br.t, J=4.5 Hz), 4.19 (2H, br.t, J=5.9 Hz)

Synthesis Example 3

Synthesis of [2-(1H-benzimidazol-1-yl)ethyl] dehydrocholate (Quencher 3)

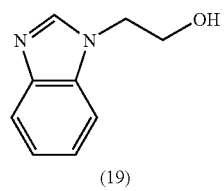

-continued

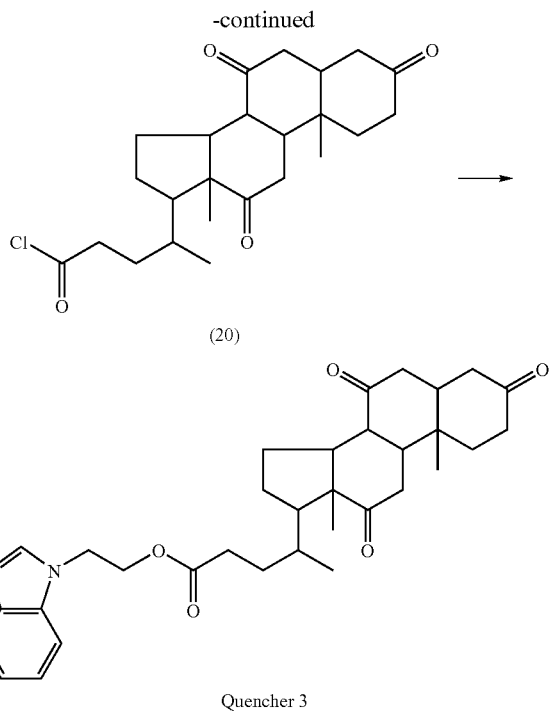

Quencher 3

With ice cooling and stirring, 42.1 g of dehydrocholic chloride (20) was added to a mixture of 16.2 g of 2-(1H-benzimidazol-1-yl)ethanol (19) and 100 g of dimethylformamide. Then the mixture was stirred at room temperature for 2 hours. Ethyl acetate was added to the solution. Subsequent standard aqueous work-up and purification by column chromatography gave 46.5 g of [2-(1H-benzimidazol-1-yl)ethyl] dehydrocholate (Quencher 3). Yield 85%.

Synthesis Example 4

Synthesis of Cholic Triformate (2-morpholinoethyl) ester (Quencher 4)

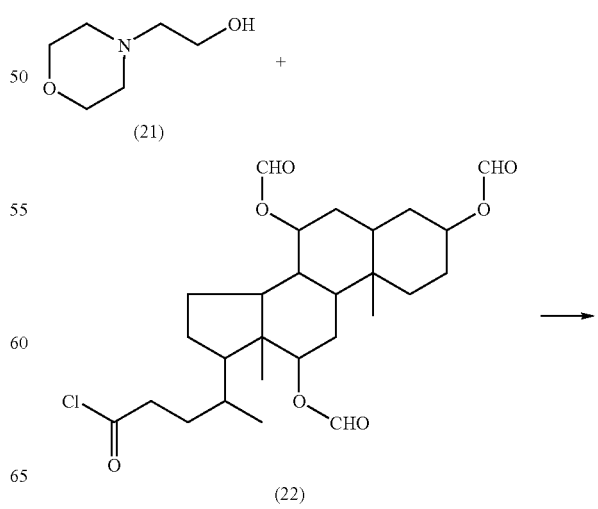

-continued

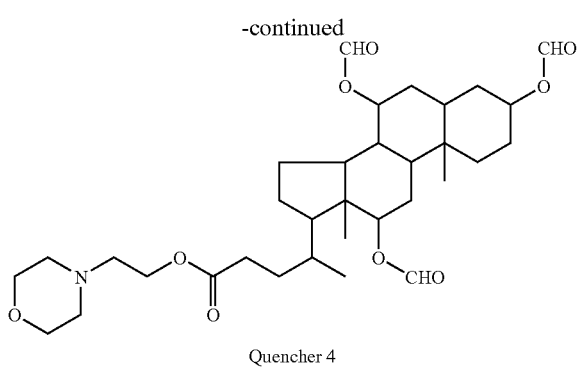

Quencher 4

A mixture of 49.3 g of cholic triformate (22), 12.7 g of oxalic chloride, and 500 g of toluene was stirred at 50° C. for 3 hours and ice cooled. 28.9 g of 2-morpholinoethanol (21) was added dropwise to the mixture, which was further stirred at room temperature for 3 hours. Subsequent standard aqueous work-up and purification by silica gel column chromatography gave 43.0 g of cholic triformate (2-morpholinoethyl) ester (Quencher 4). Yield 71%.

The target compound thus obtained was analyzed by IR and $^1$H-NMR spectroscopy.

IR (KBr): ν=2954, 2869, 2811, 1718, 1467, 1452, 1380, 1299, 1180, 1116 cm$^{-1}$ $^1$H-NMR (600 MHz in CDCl$_3$): δ=0.74 (3H, s), 0.83 (3H, d, J=6.9 Hz), 0.93 (3H, s), 1.05-1.15 (2H, m), 1.20-1.50 (5H, m), 1.50-1.60 (2H, m), 1.60-1.80 (9H, m), 1.80-1.95 (2H, m), 2.01 (1H, m), 2.05-2.15 (2H, m), 2.20 (1H, ddd, J=15.8, 9.3, 6.5 Hz), 2.48 (4H, m), 2.60 (2H, t, J=5.9 Hz), 3.69 (4H, br.t, J=4.7 Hz), 4.18 (2H, t, J=5.9 Hz), 4.70 (1H, m), 5.06 (1H, m), 5.23 (1H, m), 8.01 (1H, s), 8.09 (1H, s), 8.15 (1H, s)

Synthesis Example 5

Synthesis of 1-[2-(cholestanyloxymethoxy)ethyl]imidazole (Quencher 5)

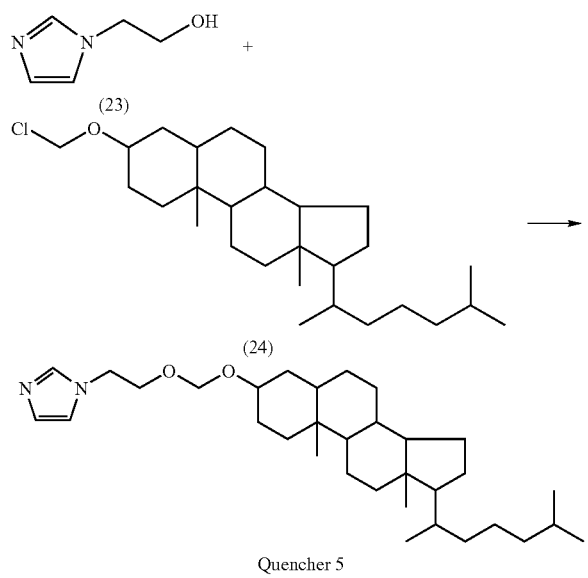

Quencher 5

Under ice cooling, 43.7 g of chloromethyl cholestanyl ether (24) was added to a mixture of 11.2 g of 2-(1H-imidazol-1-yl)ethanol (23), 11.2 g of t-butoxypotassium, and 100 g of tetrahydrofuran. Then the mixture was stirred at room temperature for 10 hours. Subsequent standard aqueous work-up and purification by silica gel column chromatography gave 38.5 g of 1-[2-(cholestanyloxymethoxy)ethyl]imidazole (Quencher 5). Yield 75%.

Synthesis Example 6

Synthesis of Cholesteryl 2-(2-phenyl-1H-benzimidazol-1-yl)acetate ester (Quencher 6)

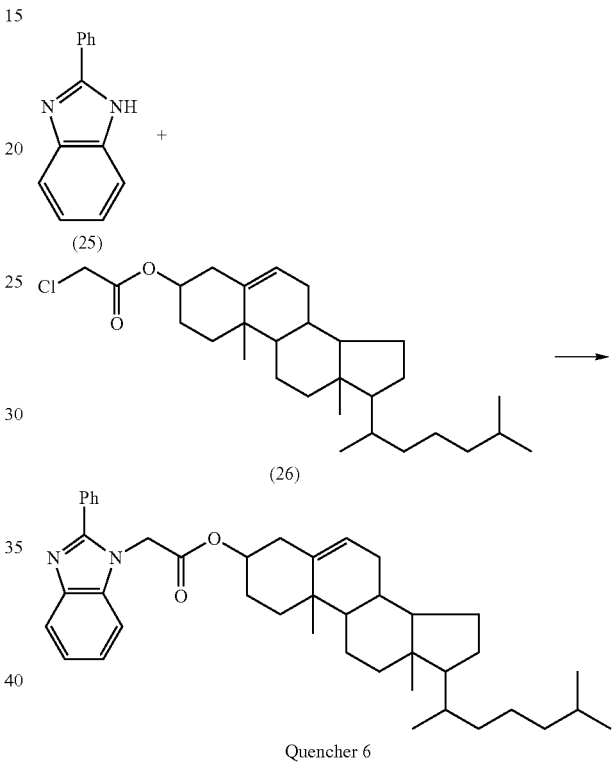

Quencher 6

A mixture of 19.4 g of 2-phenylbenzimidazole (25), 46.3 g of cholesteryl chloroacetate (26), and 200 g of dimethylformamide was heated and stirred at 100° C. for 10 hours. The reaction mixture was cooled and neutralized. Subsequent standard aqueous work-up and purification by silica gel column chromatography gave 51.1 g of cholesteryl 2-(2-phenyl-1H-benzimidazol-1-yl)acetate ester (Quencher 6). Yield 82%.

Synthesis Example 7

Synthesis of Sarsasapogenin [3-(thiomorpholino)propionate] (Quencher 7)

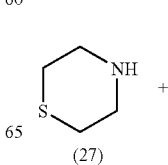

(27)

-continued

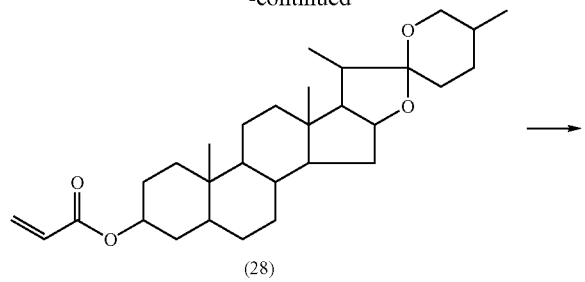

(28)

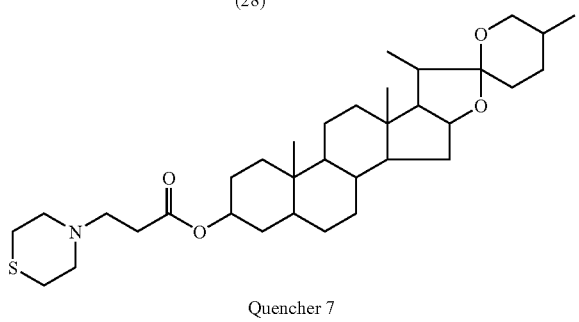

Quencher 7

10.3 g of thiomorpholine (27) was added dropwise to a mixture of 47.1 g of sarsasapogenin acrylate (28) and 200 g. of tetrahydrofuran. The mixture was stirred at room temperature for 3 hours, after which tetrahydrofuran was distilled off. Subsequent purification by silica gel column chromatography gave 56.2 g of sarsasapogenin [3-(thiomorpholino)propionate] (Quencher 7). Yield 98%.

Examples and Comparative Examples

Resist compositions were prepared using nitrogen-containing organic compounds of the invention. By carrying out the patterning process of the invention, the resist compositions were evaluated for resolution, mask coverage dependence and foreign matter on pattern.

The base polymer (Polymers 1 and 2), photoacid generator (PAG1 and 2), and quencher (Quenchers 8-10) used in Examples and Comparative Examples are identified below by their structural formula. Weight and number average molecular weights, Mw and Mn, are determined by gel permeation chromatography (GPC) using polystyrene standards.

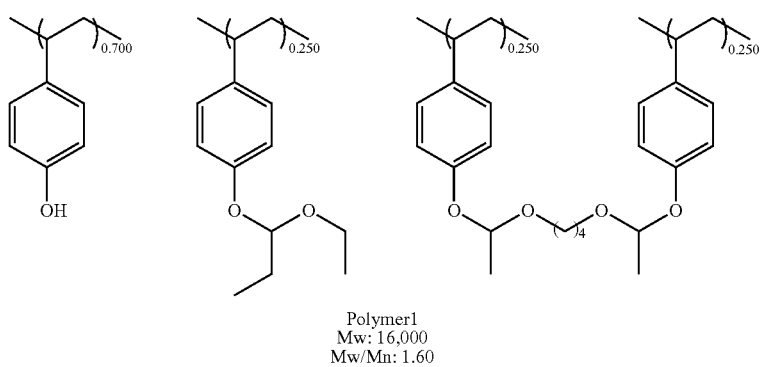

Polymer1
Mw: 16,000
Mw/Mn: 1.60

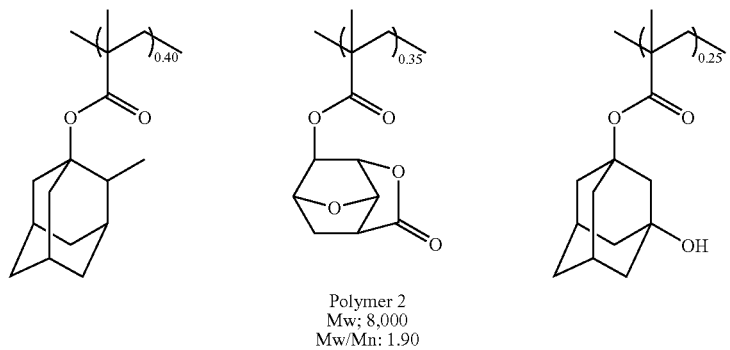

Polymer 2
Mw; 8,000
Mw/Mn: 1.90

PAG 1

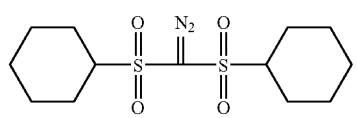

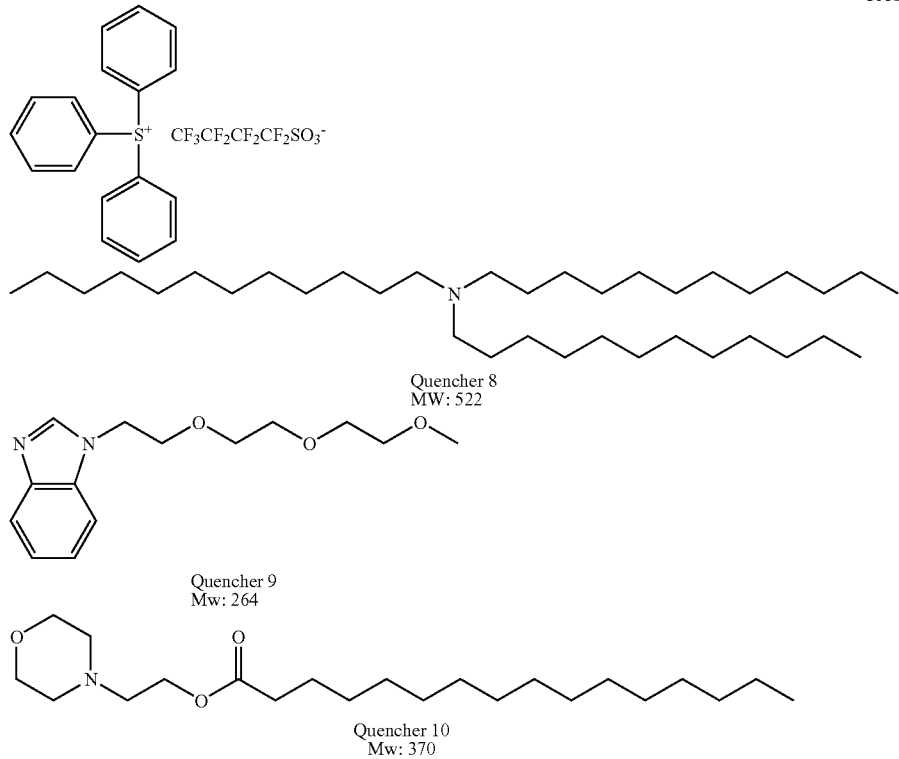

PAG 2

Quencher 8
MW: 522

Quencher 9
Mw: 264

Quencher 10
Mw: 370

Example 1

A resist composition was prepared by using the nitrogen-containing organic compound (Quencher 1) obtained in Synthesis Example 1, combining it with other components in accordance with the following recipe, and filtering the resulting solution through a Teflon® filter having a pore size of 0.2 μn.

| Components | | Parts by weight |
|---|---|---|
| (A) Base polymer: | Polymer 1 | 100 |
| (B) Acid generator: | PAG1 | 2.0 |
| (C) Solvent: | PGMEA | 280 |
| | ethyl lactate | 120 |
| (D) Quencher: | Quencher 1 | 0.13 |

The resulting resist solution was spin-coated onto a silicon wafer having an antireflective film (DUV-30 by Nissan Chemical Industries, Ltd., 55 nm) coated thereon, then baked at 115° C. for 90 seconds, forming a resist film of 550 nm thick. The resist film was exposed using a KrF excimer laser stepper NSR-S203B (by Nikon Corporation; NA=0.68; σ=0.75; ⅔ annular illumination), then heat treated at 110° C. for 90 seconds, cooled to 23° C., and puddle developed with a 2.38 wt % aqueous solution of tetramethylammonium hydroxide at 23° C. for 60 seconds, forming a 1:1 line-and-space pattern. The wafer as developed was observed under a top-down SEM. At the optimum exposure dose which provided a 1:1 resolution of a 0.18 μm line-and-space pattern, a 0.15 μm line-and-space pattern was kept separated and resolved without peeling.

Examples 2-7 and Comparative Examples 1-3

Resist compositions were prepared as in Example 1 using the nitrogen-containing organic compounds (Quenchers 2 to 7) obtained in Synthesis Examples 2 to 7 and comparative nitrogen-containing organic compounds (Quenchers 8-10). Note that the amount of amines used in these Examples and Comparative Examples is equimolar to 0.13 pbw of Quencher 1. Using the resist compositions, patterns were formed similarly.

Tests (1) Resolution

The wafer as developed was observed under a top-down SEM. The optimum exposure is an exposure dose that provided a resolution to a 180-nm 1:1 grouped line-and-space pattern in a bright field (region with a low mask coverage). At the optimum exposure, whether or not a 150-nm 1:1 grouped line-and-space pattern was kept separated and resolved without peeling was determined as an index of resolution.

(2) Mask Coverage Dependence

The wafer as developed was observed under a top-down SEM. The optimum exposure is an exposure dose that provided a resolution to a 180-nm 1:1 grouped line-and-space pattern in a bright field (region with a low mask coverage). The pattern profile of a 180-nm 1:1 grouped line-and-space pattern at the optimum exposure and in a dark field (region with a high mask coverage) was observed under a sectional SEM as an index of mask coverage dependence. The mask coverage dependence is good when the profile is rectangular and poor when the profile is T-top.

(3) Foreign Matter on Pattern

The wafer as developed was observed under a top-down SEM and the presence of foreign matter on the pattern was visually inspected.

The resist compositions of Examples 1 to 7 and Comparative Examples 1 to 3 were tested for resolution, mask coverage dependence, and foreign matter on pattern.

Based on the test results, Table 1 tabulates the 150-nm resolution, mask coverage dependence (dark field pattern profile), and foreign matter on pattern for a 1:1 line-and-space pattern.

TABLE 1

| | Quencher | 150-nm resolution | Pattern profile | Foreign matter |
|---|---|---|---|---|
| Example 1 | quencher 1 | resolved | faint T-top | nil |
| Example 2 | quencher 2 | resolved | faint T-top | nil |
| Example 3 | quencher 3 | resolved | rectangular | nil |
| Example 4 | quencher 4 | resolved | rectangular | nil |
| Example 5 | quencher 5 | resolved | rectangular | nil |
| Example 6 | quencher 6 | resolved | rectangular | nil |
| Example 7 | quencher 7 | resolved | rectangular | nil |
| Comparative Example 1 | quencher 8 | not resolved | faint T-top | many |
| Comparative Example 2 | quencher 9 | resolved | extreme T-top | nil |
| Comparative Example 3 | quencher 10 | resolved | extreme T-top | nil |

Example 8

A resist composition was prepared by using the nitrogen-containing organic compound (Quencher 1) obtained in Synthesis Example 1, combining it with other components in accordance with the following recipe, and filtering the resulting solution through a Teflone® filter having a pore size of 0.2 µm.

| Components | | Parts by weight |
|---|---|---|
| (A) Base polymer: | Polymer 2 | 80 |
| (B) Acid generator: | PAG2 | 2.0 |
| (C) Solvent: | PGMEA | 640 |
| (D) Quencher: | Quencher 1 | 0.33 |

The resulting resist solution was spin-coated onto a silicon wafer having an antireflective film (ARC29A by Nissan Chemical Industries, Ltd., 78 nm) coated thereon, then baked at 120° C. for 60 seconds, forming a resist film of 300 nm thick. The resist film was exposed using an ArF excimer laser stepper NSR-S305B (by Nikon Corporation; NA=0.68; σ=0.85; ⅔ annular illumination), then heat treated at 120° C. for 60 seconds, cooled to 23° C., and puddle developed with a 2.38 wt % aqueous solution of tetramethylammonium hydroxide at 23° C. for 60 seconds, forming a 1:1 line-and-space pattern. The wafer as developed was observed under a top-down SEM. At the optimum exposure dose which provided a 1:1 resolution of a 0.12 µm line-and-space pattern, a 0.10 µm line-and-space pattern was kept separated and resolved without peeling.

Examples 9-14 and Comparative Examples 4-6

Resist compositions were prepared as in Example 8 using the nitrogen-containing organic compounds (Quenchers 2 to 7) obtained in Synthesis Examples 2 to 7 and comparative nitrogen-containing organic compounds (Quenchers 8-10). Note that the amount of amines used in these Examples and Comparative Examples is equimolar to 0.33 pbw of Quencher 1. Using the resist compositions, patterns were formed similarly.

Tests (1) Resolution

The wafer as developed was observed under a top-down SEM. The optimum exposure is an exposure dose that provided a resolution to a 120-nm 1:1 grouped line-and-space pattern in a bright field (region with a low mask coverage). At the optimum exposure, whether or not a 100-nm 1:1 grouped line-and-space pattern was kept separated and resolved without peeling was determined as an index of resolution.

(2) Mask Coverage Dependence

The wafer as developed was observed under a top-down SEM. The optimum exposure is an exposure dose that provided a resolution to a 120-nm 1:1 grouped line-and-space pattern in a bright field (region with a low mask coverage). The pattern profile of a 120-nm 1:1 grouped line-and-space pattern at the optimum exposure and in a dark field (region with a high mask coverage) was observed under a sectional SEM as an index of mask coverage dependence. The mask coverage dependence is good when the profile is rectangular and poor when the profile is T-top.

(3) Foreign Matter on Pattern

The wafer as developed was observed under a top-down SEM and the presence of foreign matter on the pattern was visually inspected.

The resist compositions of Examples 8 to 14 and Comparative Examples 4 to 6 were tested for resolution, mask coverage dependence, and foreign matter on pattern.

Based on the test results, Table 2 tabulates the 100-nm resolution, mask coverage dependence (dark field pattern profile), and foreign matter on pattern for a 1:1 line-and-space pattern.

TABLE 2

| | Quencher | 150-nm resolution | Pattern profile | Foreign matter |
|---|---|---|---|---|
| Example 8 | quencher 1 | resolved | faint T-top | nil |
| Example 9 | quencher 2 | resolved | faint T-top | nil |
| Example 10 | quencher 3 | resolved | rectangular | nil |
| Example 11 | quencher 4 | resolved | rectangular | nil |
| Example 12 | quencher 5 | resolved | rectangular | nil |
| Example 13 | quencher 6 | resolved | rectangular | nil |
| Example 14 | quencher 7 | resolved | rectangular | nil |
| Comparative Example 4 | quencher 8 | not resolved | not resolved | many |
| Comparative Example 5 | quencher 9 | resolved | extreme T-top | nil |
| Comparative Example 6 | quencher 10 | resolved | extreme T-top | nil |

It is evident from Tables 1 and 2 that the resist compositions within the scope of the invention satisfy both a high resolution and improved mask coverage dependence and are thus suitable in photolithography micropatterning.

Japanese Patent Application No. 2006-289489 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A nitrogen-containing organic compound bearing a nitrogen-containing heterocycle and a steroid structure, represented by one of the general formulae (2') to (10'):

[Chemical structures (2'), (3'), (4'), (5'), (6'), (7'), (8'), (9'), (10')]

wherein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^{6'}$ is an alkyl group of 21 to 49 carbon atoms having a steroid structure which may contain a hydroxyl, carbonyl, ester, ether, cyano or acetal group, $R^7$ is a single bond, methylene group, oxygen atom or sulfur atom, $R^8$ is a straight or branched $C_1$-$C_9$ alkylene group, and $R^{9'}$ is an alkyl group of 22 to 50 carbon atoms having a steroid structure which may contain a hydroxyl, carbonyl, ester, ether or cyano group.

2. A resist composition comprising as a quencher at least one nitrogen-containing organic compound bearing a nitrogen-containing heterocycle and having a molecular weight of at least 380, represented by the general formula (1):

[Chemical structure (1)]

wherein $R^1$ is a straight, branched or cyclic divalent substituent group of 2 to 20 carbon atoms to form a nitrogen-containing heteroaliphatic or heteroaromatic ring with the nitrogen atom to which it is attached at both ends, which group may contain an oxygen, nitrogen, sulfur or halogen atom, $R^2$ is a straight or branched alkylene group of 2 to 10 carbon atoms which may contain a carbonyl group, and $R^3$ is —CO—$R^6$, —CH$_2$—OR$^6$, $R^9$, —CO—$R^{6'}$, —CH$_2$—OR$^{6'}$ or $R^{9'}$ wherein $R^6$ is selected from the group consisting of the following formulae:

[Structures: (n-C$_{21}$H$_{43}$), (n-C$_{22}$H$_{45}$), (n-C$_{23}$H$_{47}$), (n-C$_{25}$H$_{51}$), (n-C$_{27}$H$_{55}$), (n-C$_{29}$H$_{59}$), (n-C$_{41}$H$_{83}$), (n-C$_{49}$H$_{99}$), branched structure with subscript 6, ester with (n-C$_{21}$H$_{43}$), O(n-C$_{20}$H$_{41}$), O(n-C$_{21}$H$_{43}$), (CH$_2$)$_{20}$CN,]

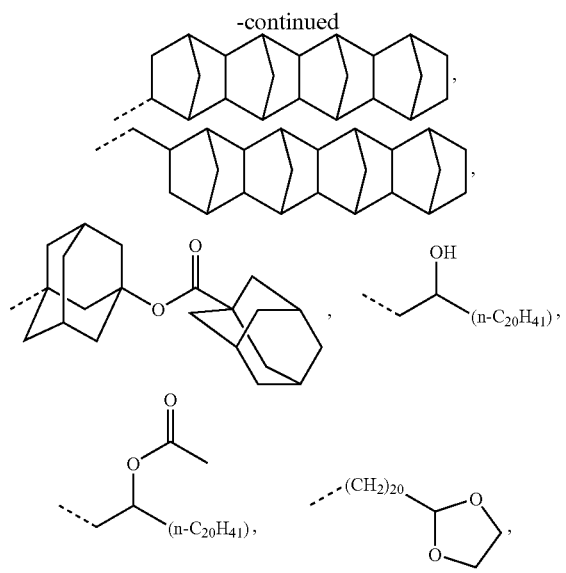
and $R^{6'}$,
$R^9$ is selected from the group consisting of the following formulae:
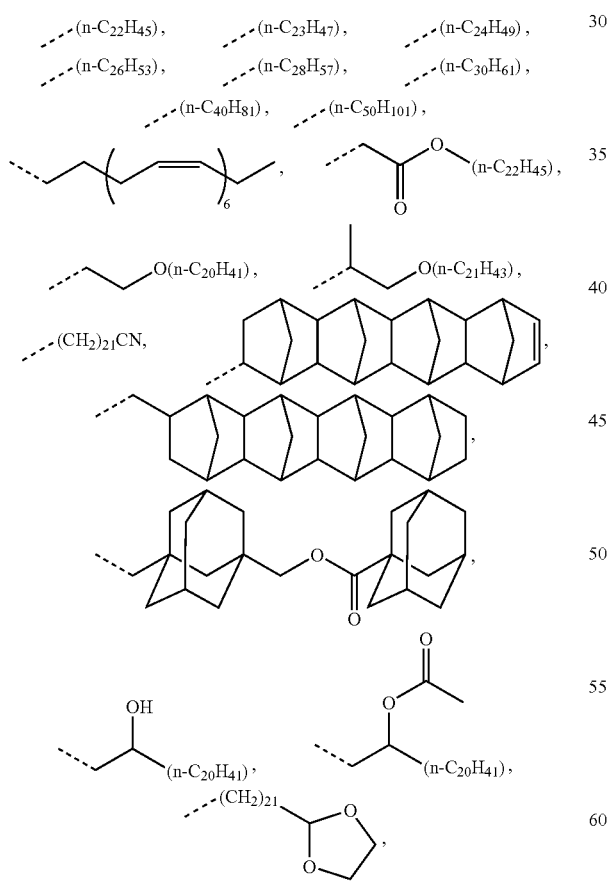
and $R^{9'}$,
$R^{6'}$ is selected from the group consisting of the following formulae:
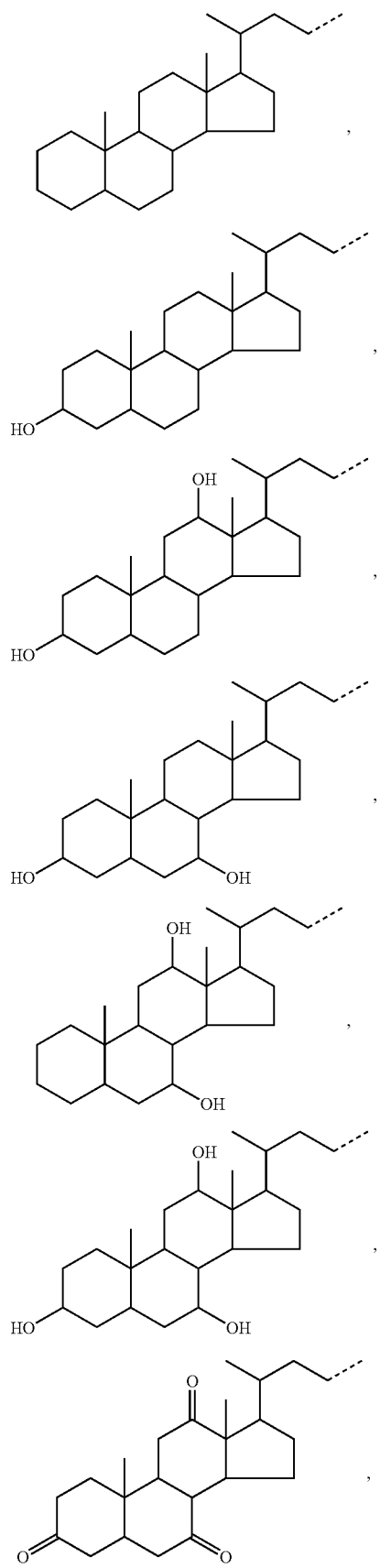

-continued
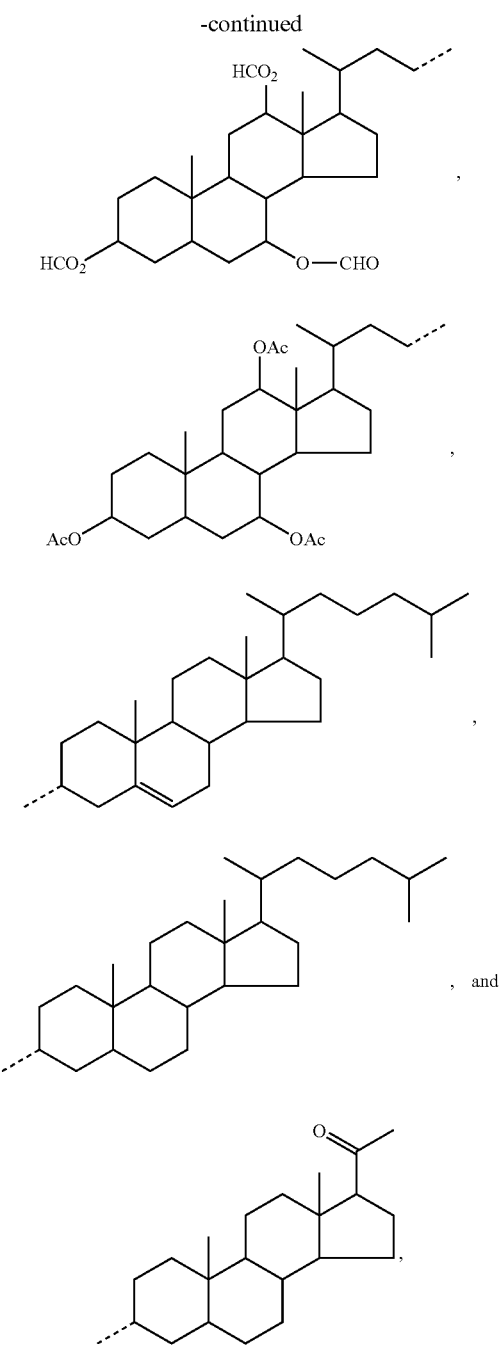
and $R^{9'}$ is selected from the group consisting of the following formulae:
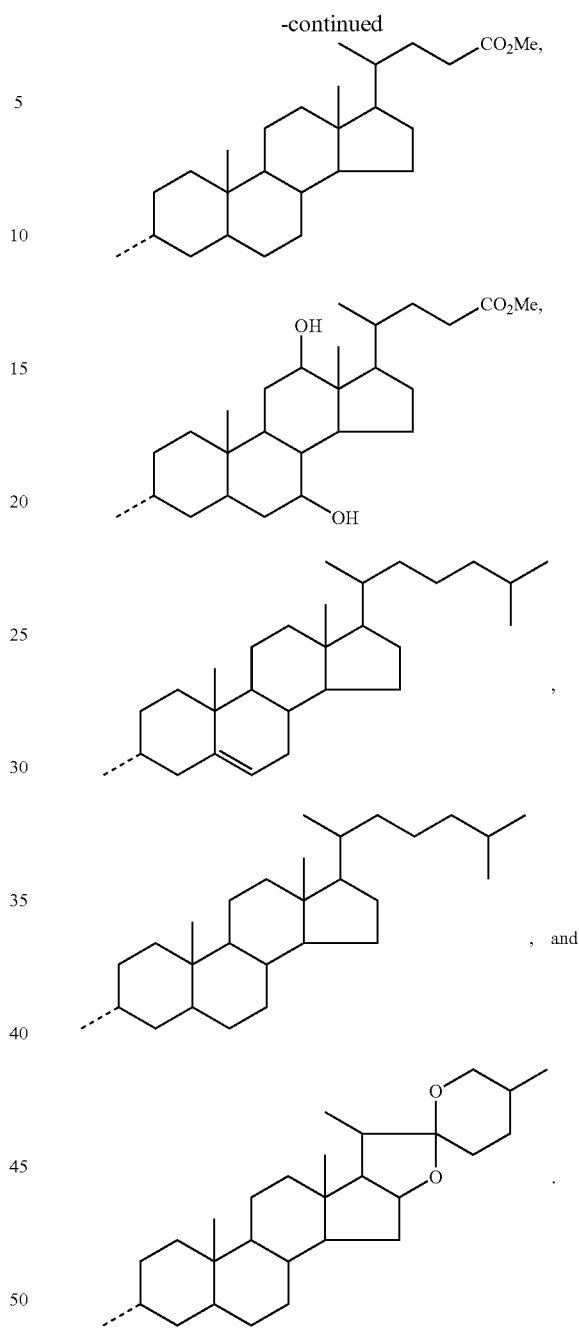
3. The resist composition of claim 2, comprising as a quencher at least one of nitrogen-containing organic compounds bearing a nitrogen-containing heterocycle and having a molecular weight of at least 430, represented by the general formulae (2) to (10):
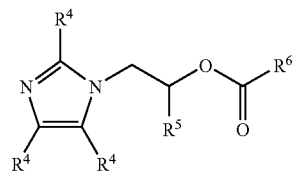
(2)

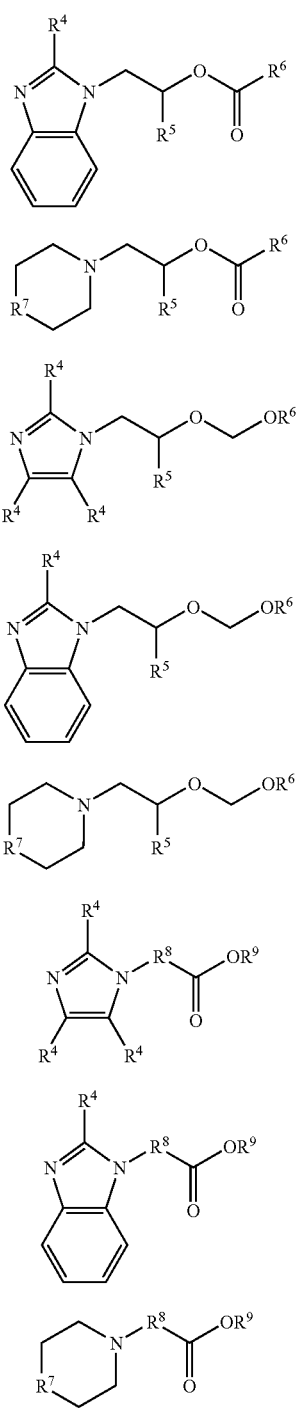

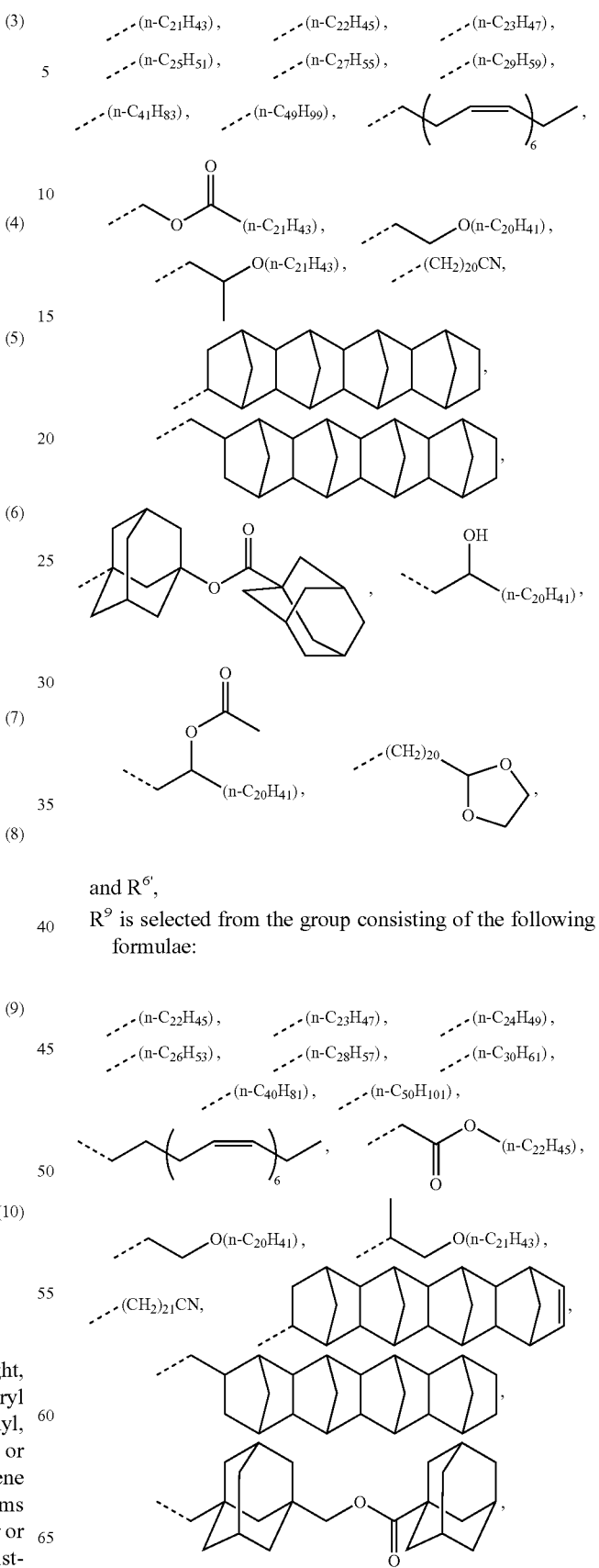

wherein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^7$ is a single bond, methylene group, oxygen atom or sulfur atom, $R^8$ is a straight or branched $C_1$-$C_9$ alkylene group, $R^9$ is an alkyl group of 22 to 50 carbon atoms which may contain a hydroxyl, carbonyl, ester, ether or cyano group, and $R^6$ is selected from the group consisting of the following formulae:

and $R^{6\prime}$, $R^9$ is selected from the group consisting of the following formulae:

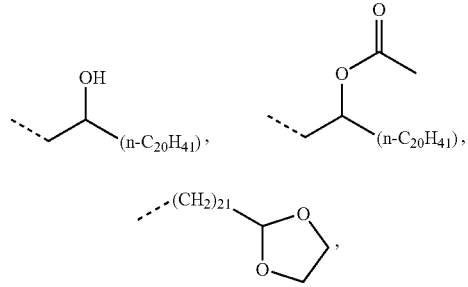
and R^{9'},
R^{6'} is selected from the group consisting of the following formulae:
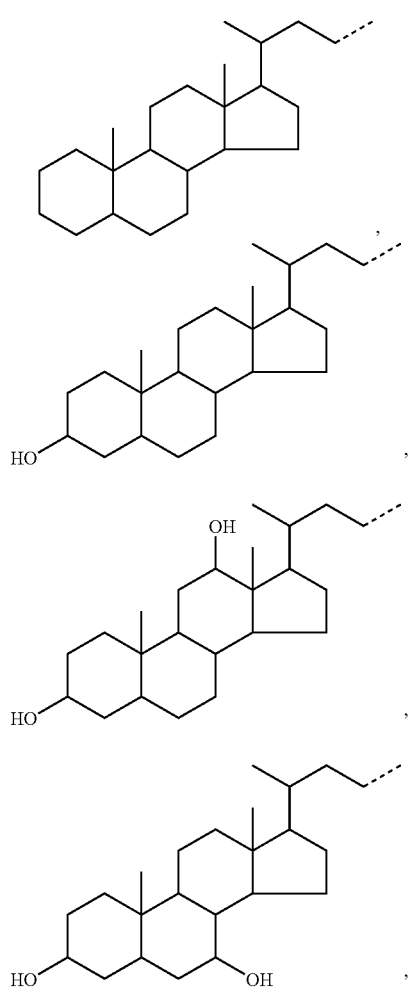
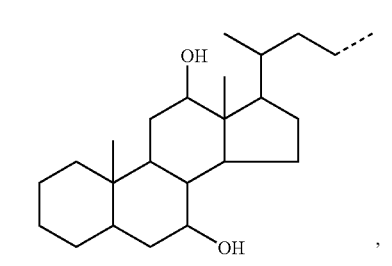
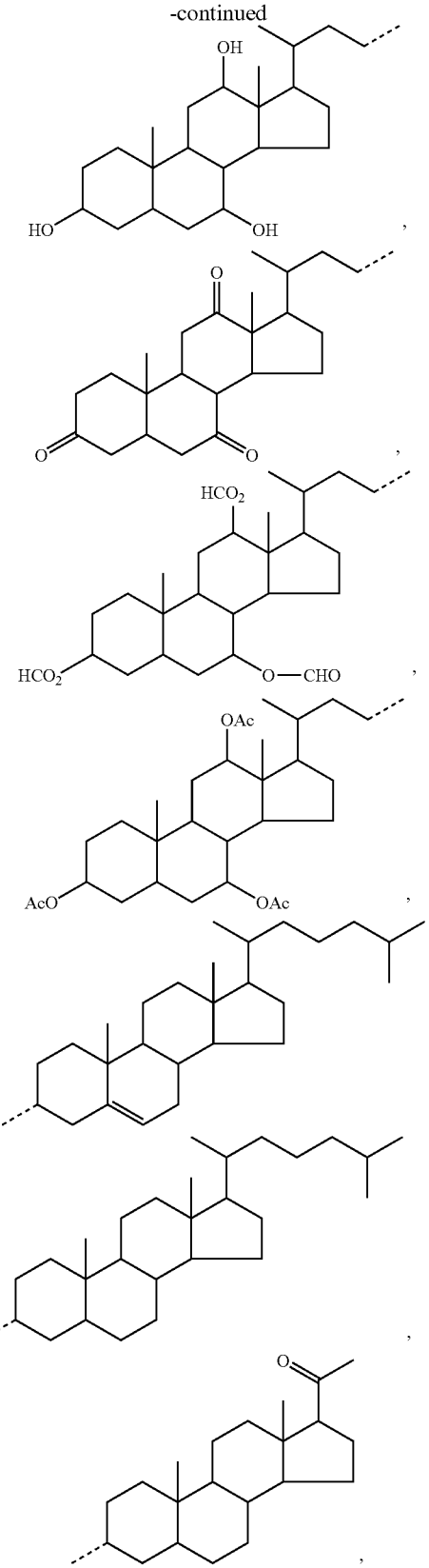
and R^{9'} is selected from the group consisting of the following formulae:

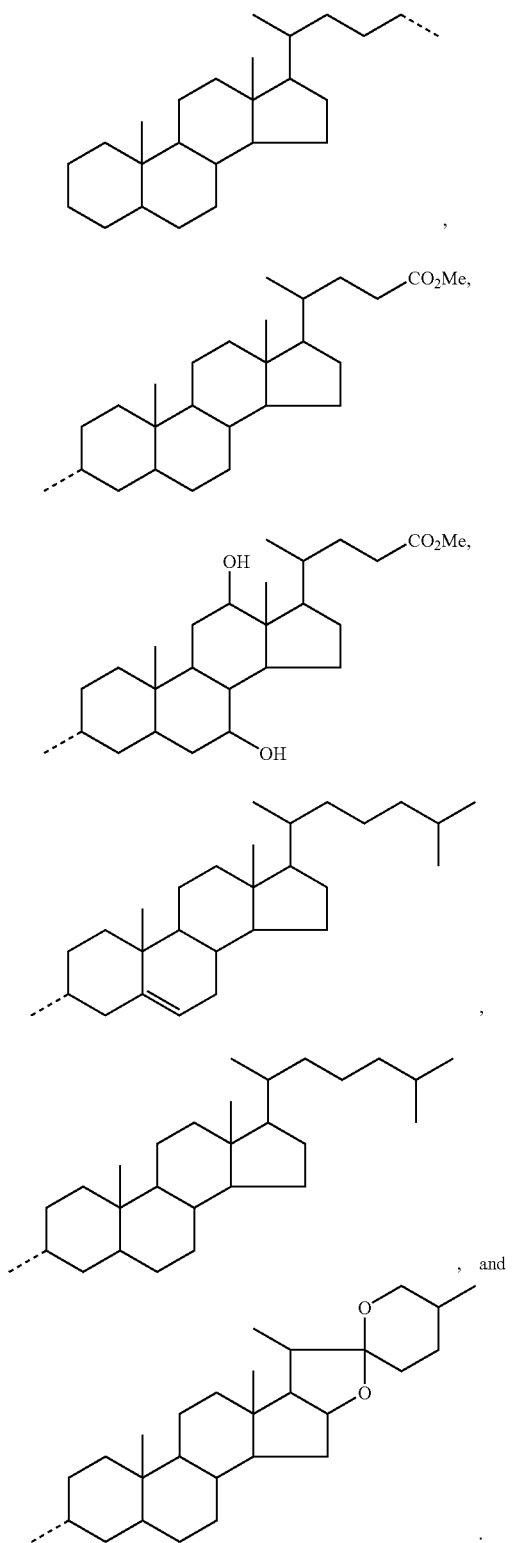

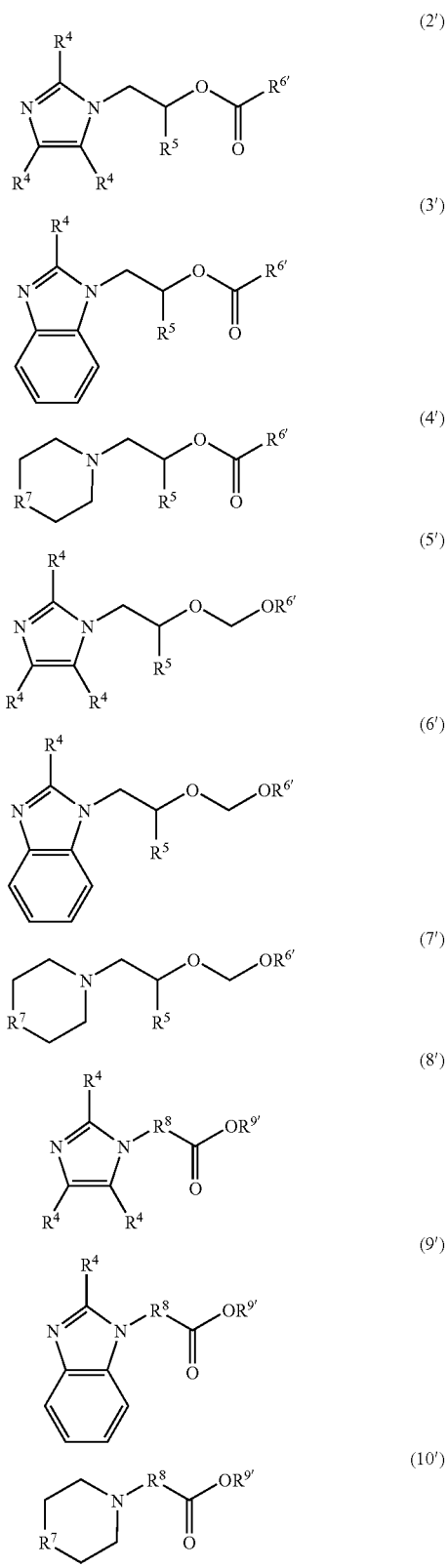

4. The resist composition of claim 2, comprising as a quencher at least one of nitrogen-containing organic compounds bearing a nitrogen-containing heterocycle and a steroid structure and having a molecular weight of at least 430, represented by the general formulae (2') to (10'):

wherein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^7$ is a single bond, methylene group, oxygen atom or sulfur atom, $R^8$ is a straight or branched $C_1$-$C_9$ alkylene group, $R^{9'}$ is an alkyl group of 22 to 50 carbon atoms having a steroid structure which may contain a hydroxyl, carbonyl, ester, ether or cyano group, and $R^{6'}$ is selected from the group consisting of the following formulae:

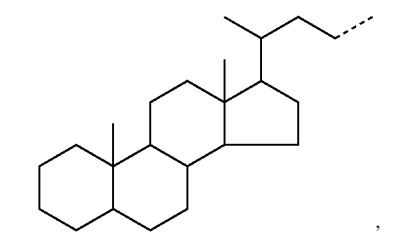,

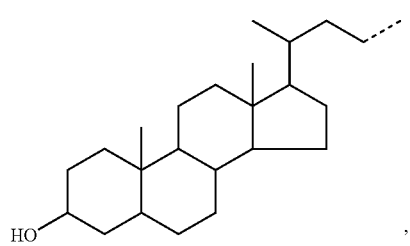,

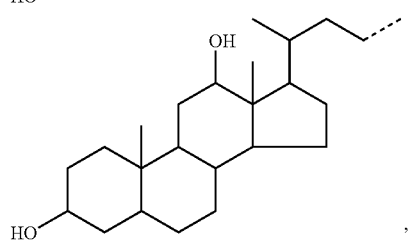,

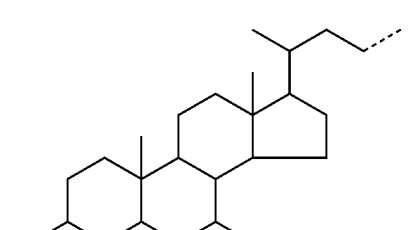,

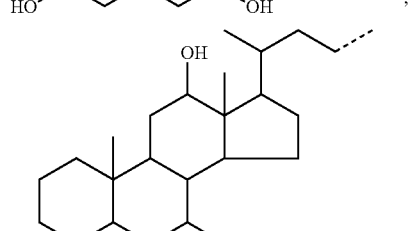,

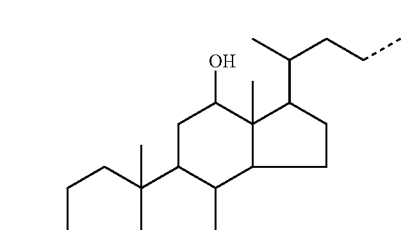,

-continued

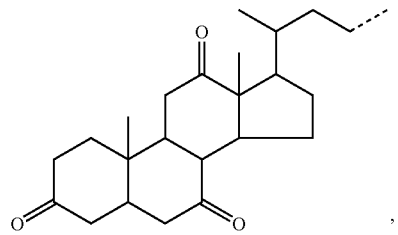,

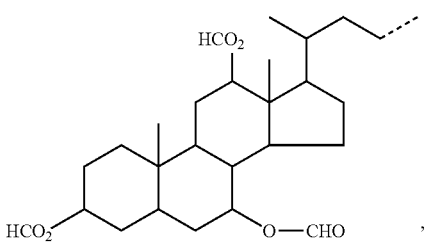,

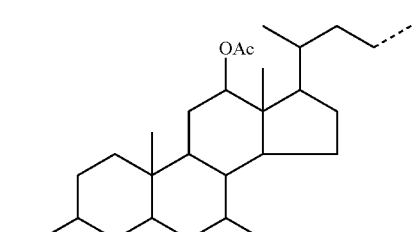,

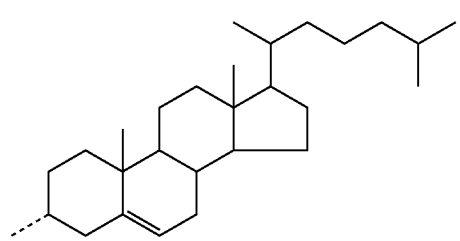,

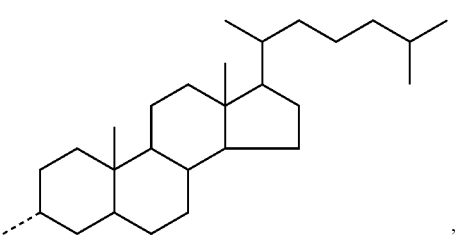, and

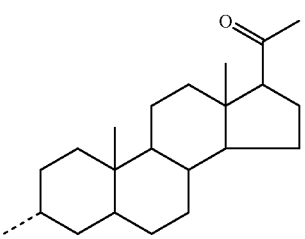, and $R^{9'}$ is selected from the group consisting of the following formulae:

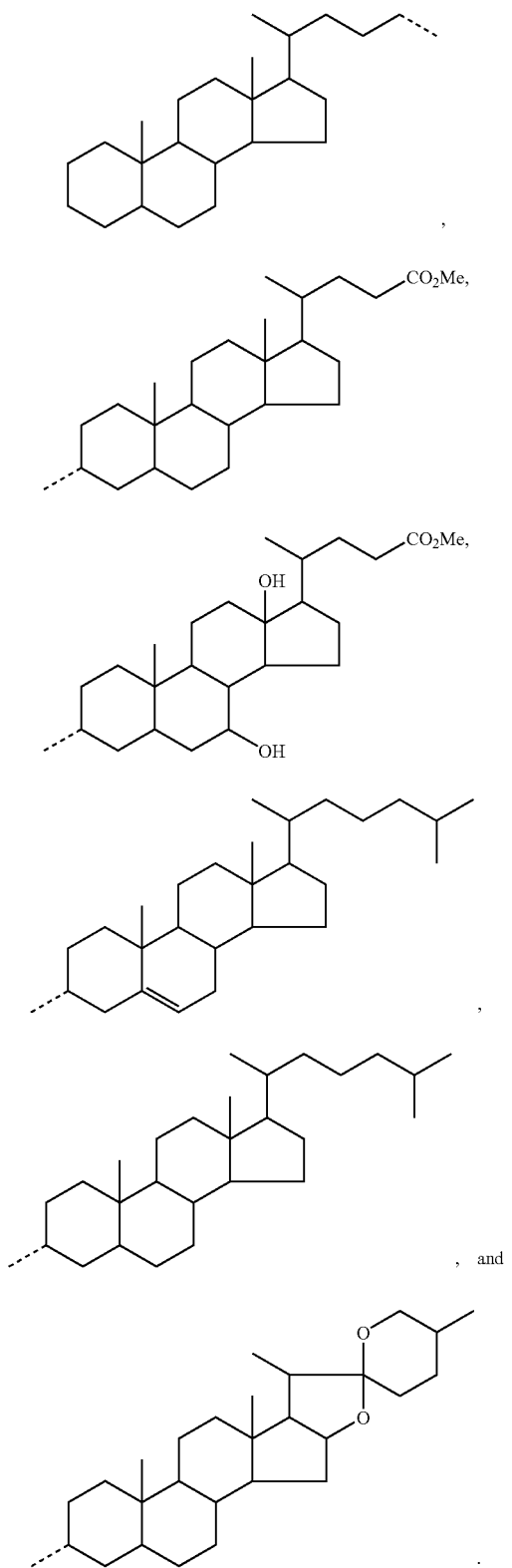
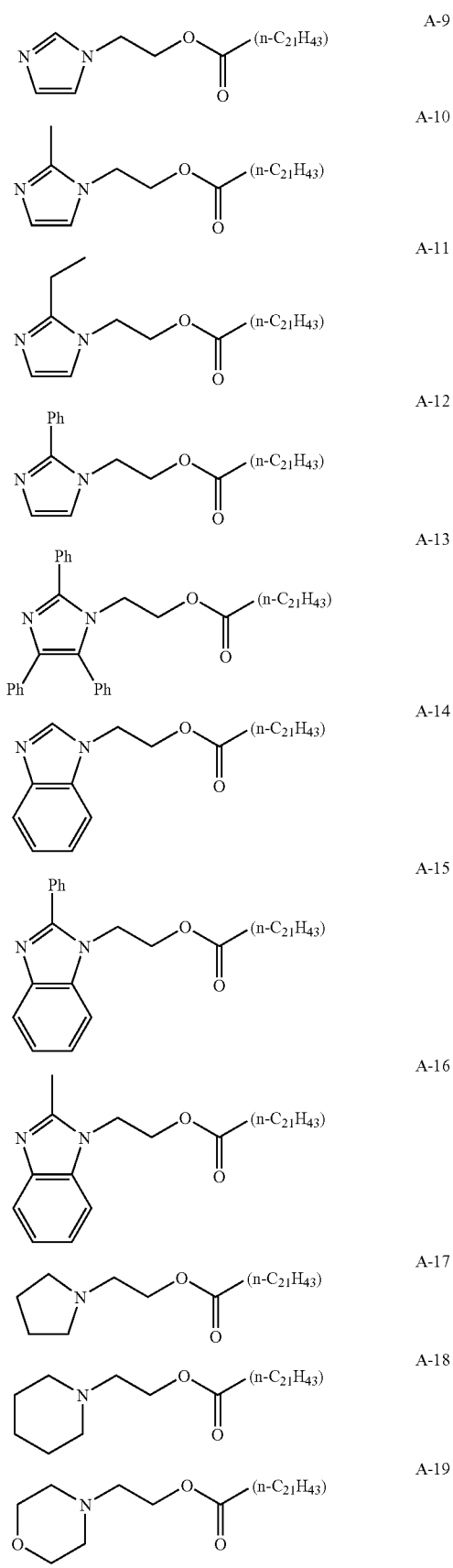
5. The resist composition of claim 3, wherein the nitrogen-containing organic compound having any one of formulae (2) to (10) is one having the formula selected from the group consisting of the following formulae A-9 to A-62:

-continued
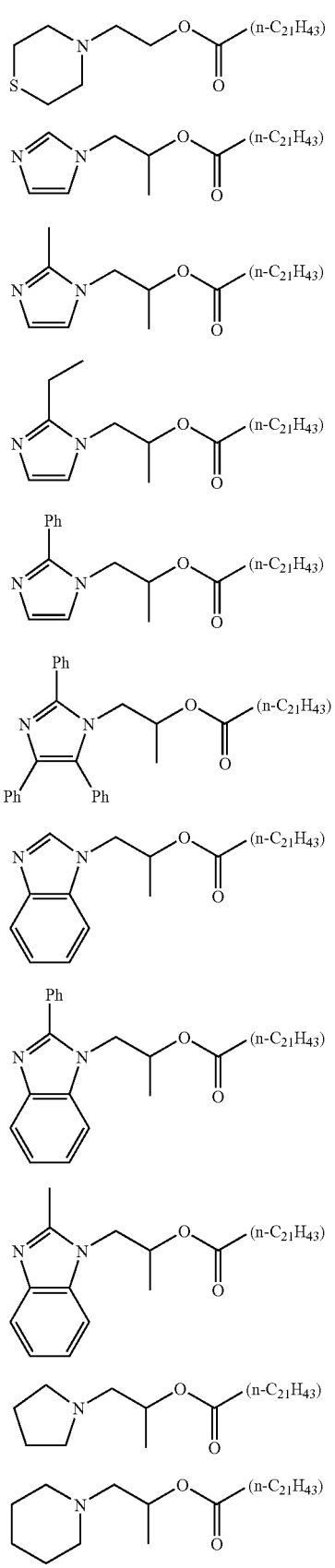
A-20
A-21
A-22
A-23
A-24
A-25
A-26
A-27
A-28
A-29
A-30
-continued
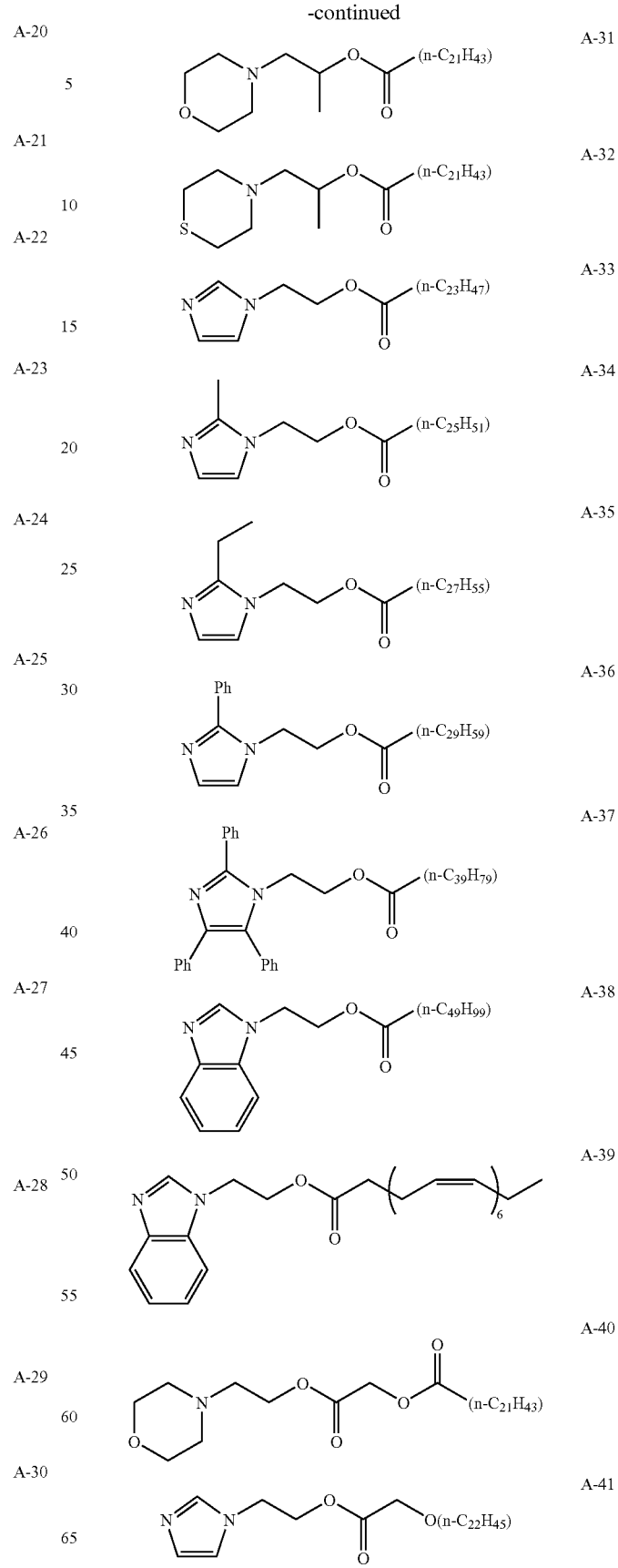
A-31
A-32
A-33
A-34
A-35
A-36
A-37
A-38
A-39
A-40
A-41

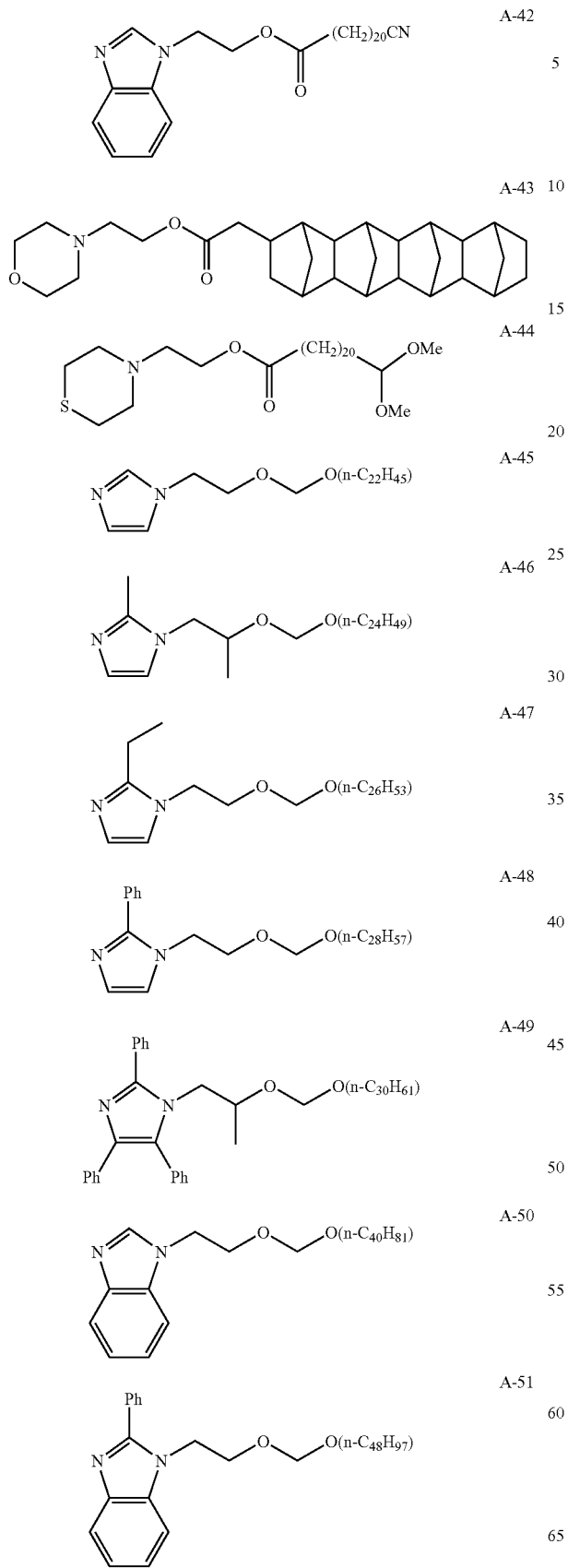

A-62
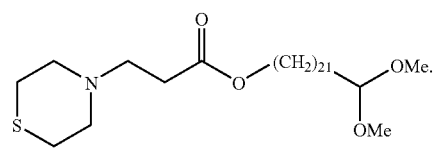
6. The resist composition of claim 4, wherein the nitrogen-containing organic compound having any one of formulae (2') to (10') is one having the formula selected from the group consisting of the following formulae A-63 to A-76:
A-63
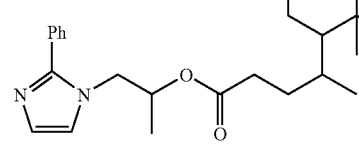
A-64
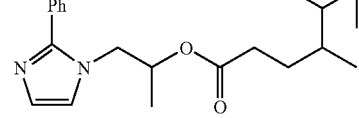
A-65
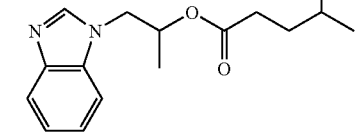
A-66
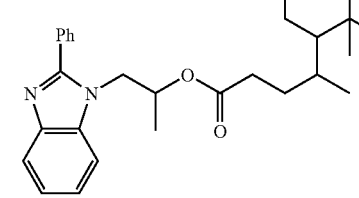
A-67
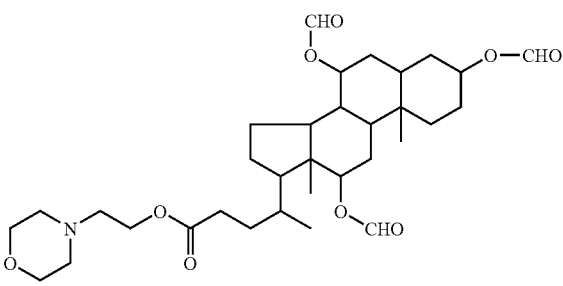
A-68
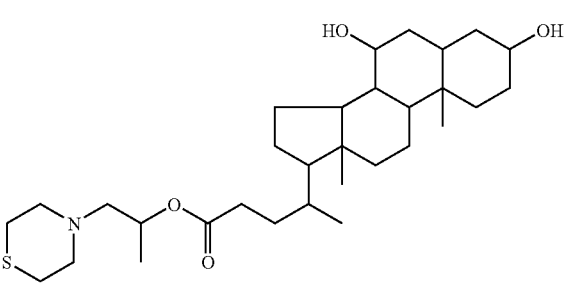
A-69
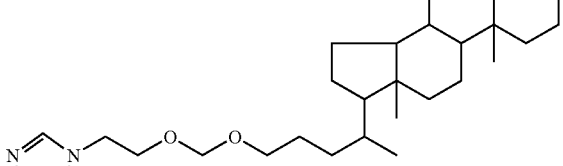
A-70
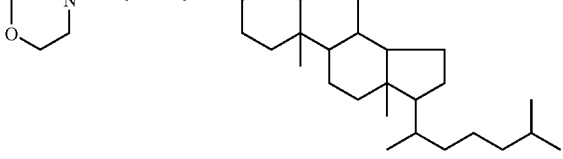
A-71
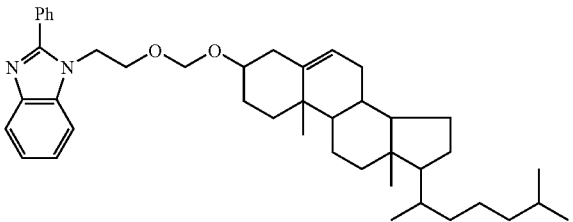
A-72
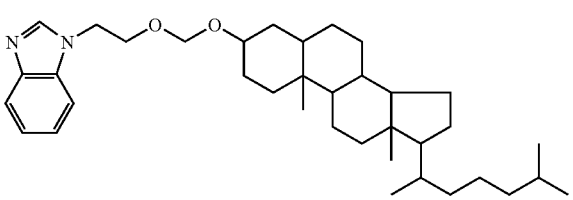

-continued

A-73
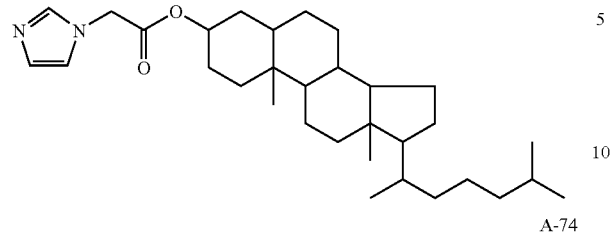

A-74
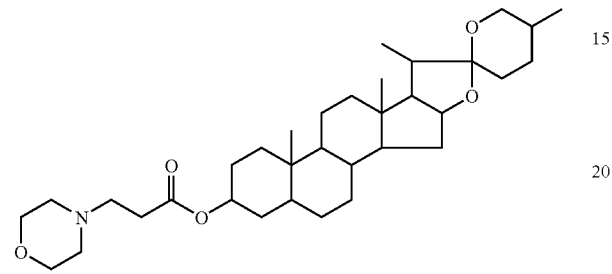

A-75
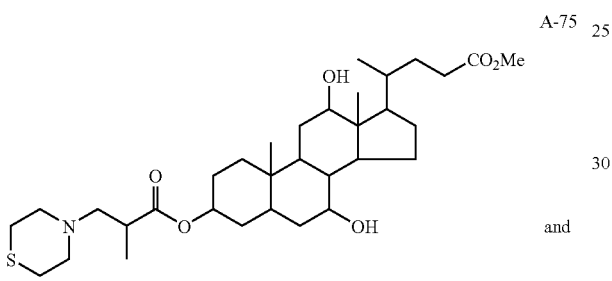

and

A-76
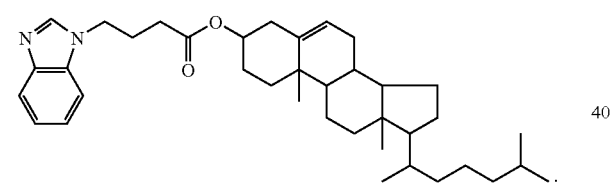

7. A nitrogen-containing organic compound bearing a nitrogen-containing heterocycle, represented by one of the general formulae (2) to (10):

(2)
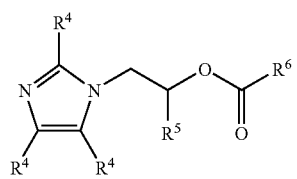

(3)
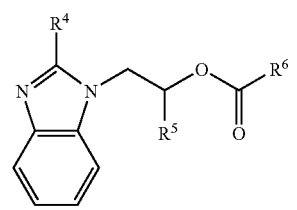

-continued (4)
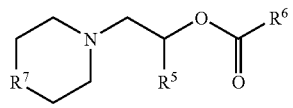

(5)
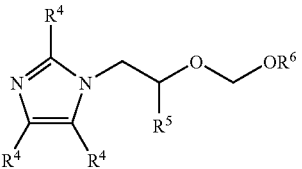

(6)
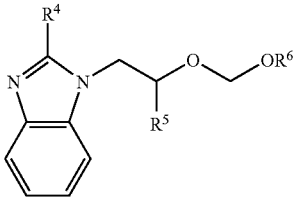

(7)
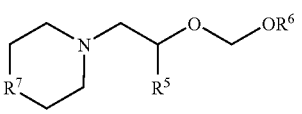

(8)
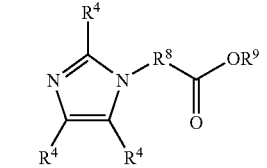

(9)
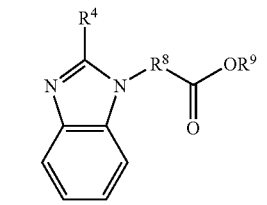

(10)
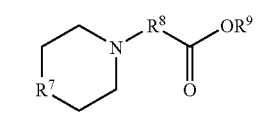

wherein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, $R^7$ is a single bond, methylene group, oxygen atom or sulfur atom, $R^8$ is a straight or branched $C_1$-$C_9$ alkylene group, $R^9$ is an alkyl group of 22 to 50 carbon atoms which may contain a hydroxyl, carbonyl, ester, ether or cyano group, and $R^6$ is selected from the group consisting of the following formulae:

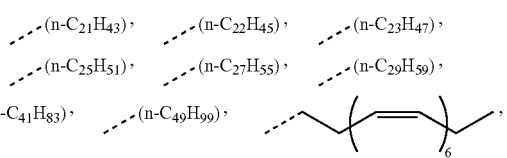

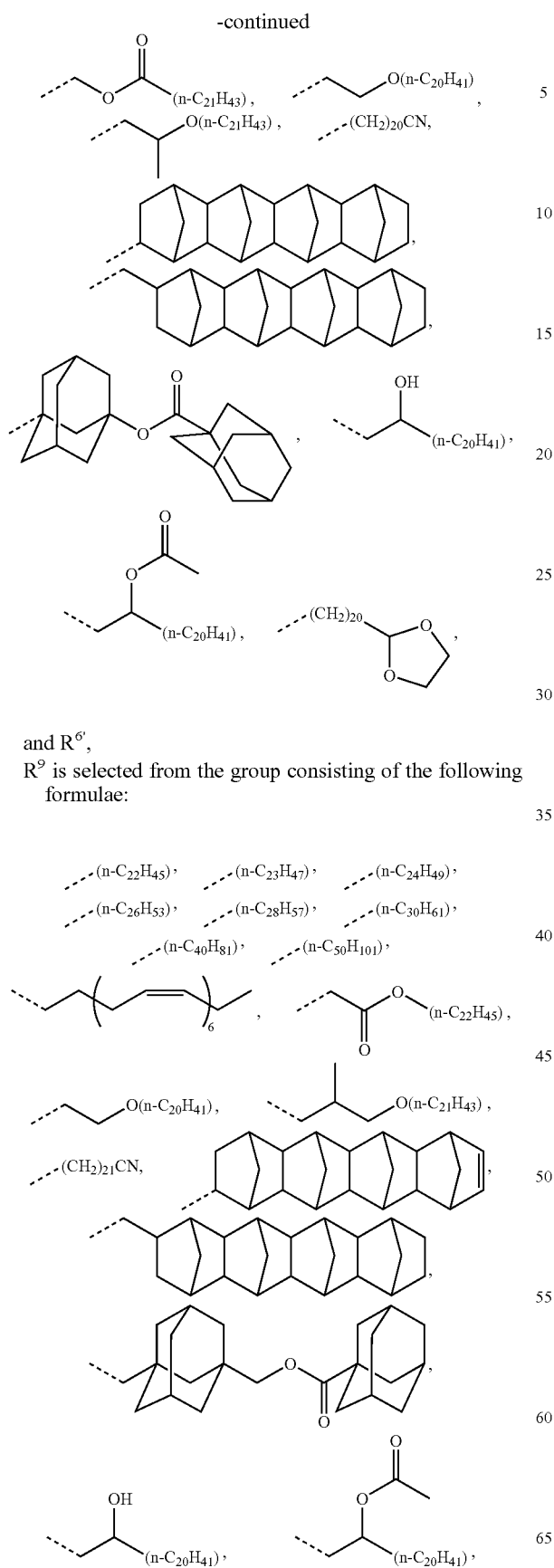

-continued
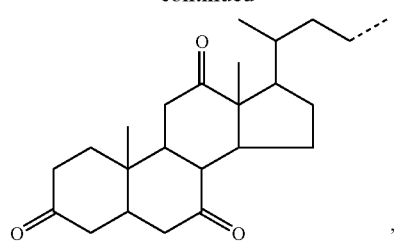
,
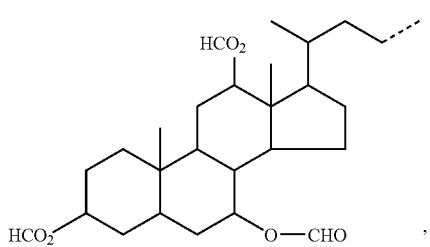
,
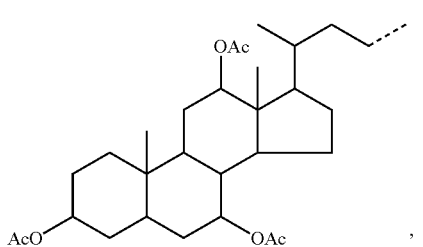
,
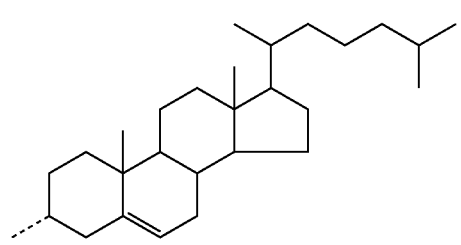
,
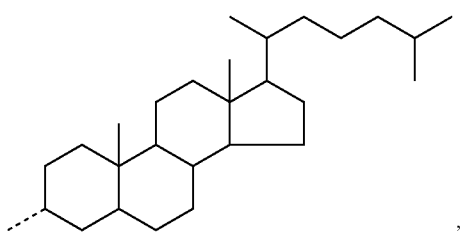
, and
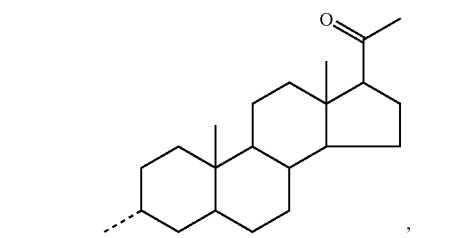
,
and $R^{9'}$ is selected from the group consisting of the following formulae:
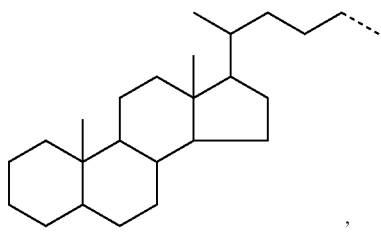
,
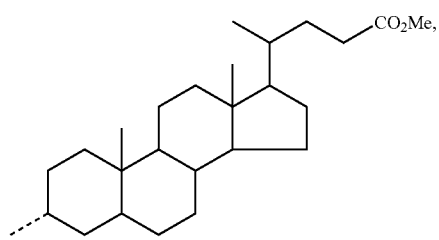
,
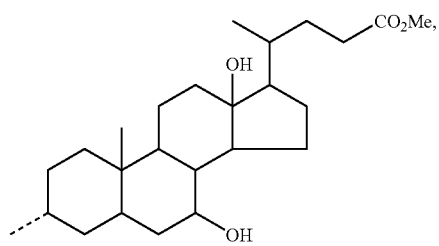
,
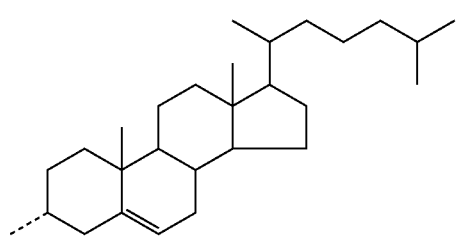
,
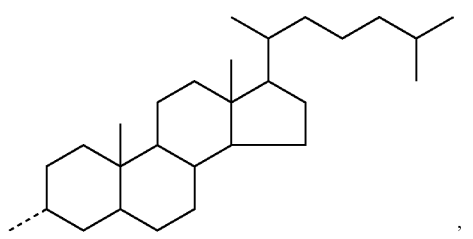
, and
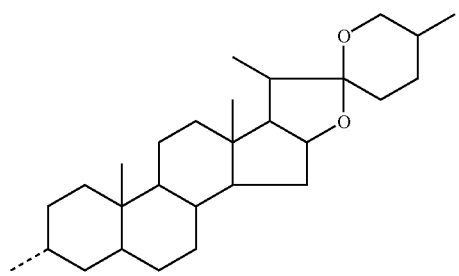
.
8. A nitrogen-containing organic compound bearing a nitrogen-containing heterocycle and a steroid structure, represented by one of the general formulae (2') to (10'):

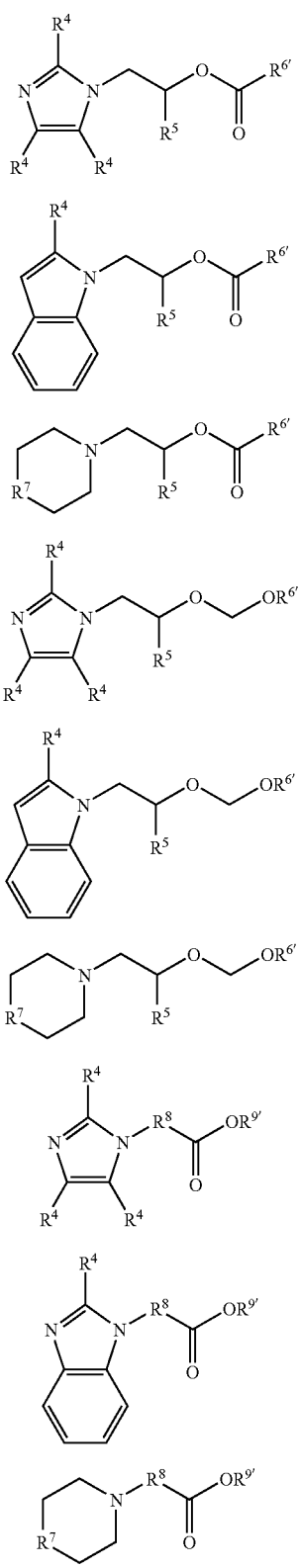

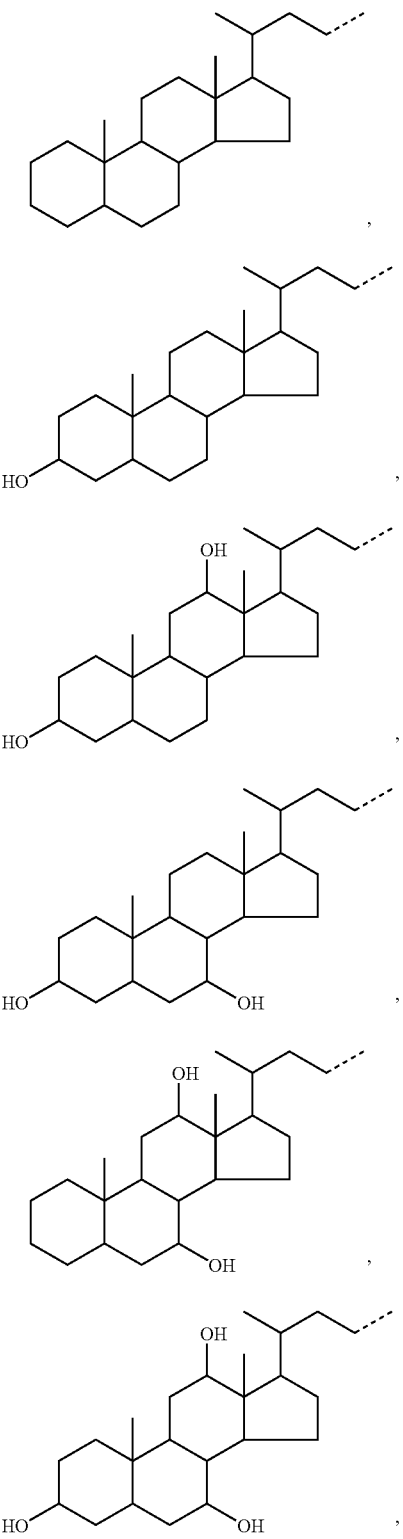

$R^7$ is a single bond, methylene group, oxygen atom or sulfur atom, $R^8$ is a straight or branched $C_1$-$C_9$ alkylene group, $R^{9'}$ is an alkyl group of 22 to 50 carbon atoms having a steroid structure which may contain a hydroxyl, carbonyl, ester, ether or cyano group, and $R^{6'}$ is selected from the group consisting of the following formulae:

wherein $R^4$ is each independently hydrogen, a straight, branched or cyclic $C_1$-$C_{10}$ alkyl group, $C_6$-$C_{15}$ aryl group or $C_7$-$C_{15}$ aralkyl group, $R^5$ is hydrogen or methyl, -continued
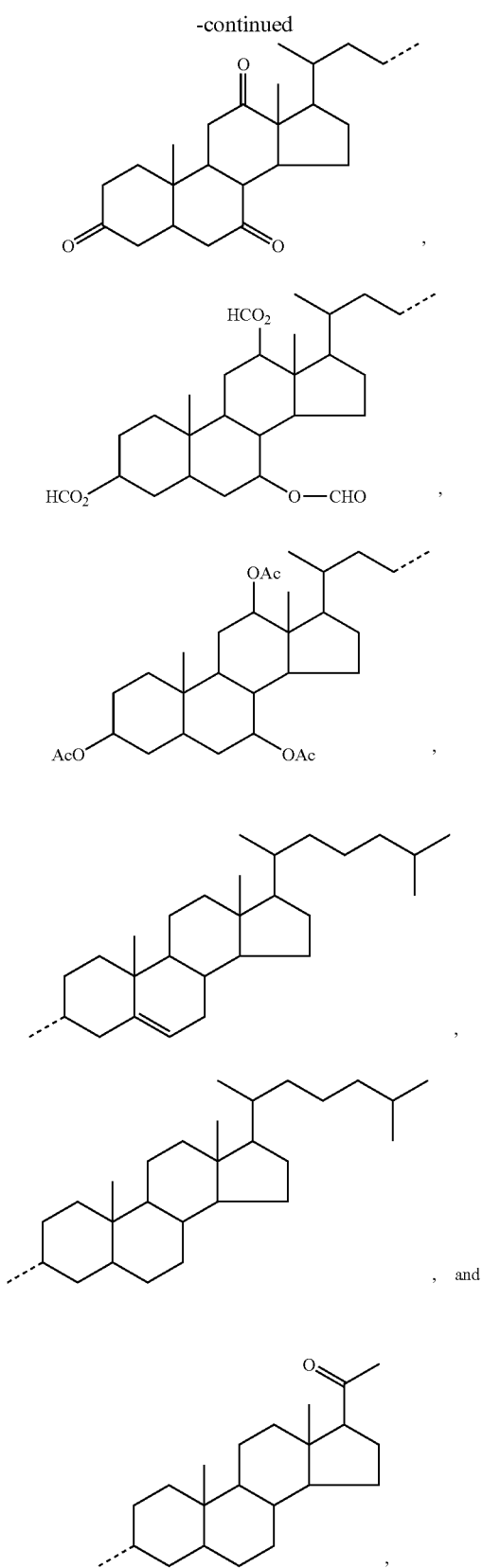
and R[9'] is selected from the group consisting of the following formulae:
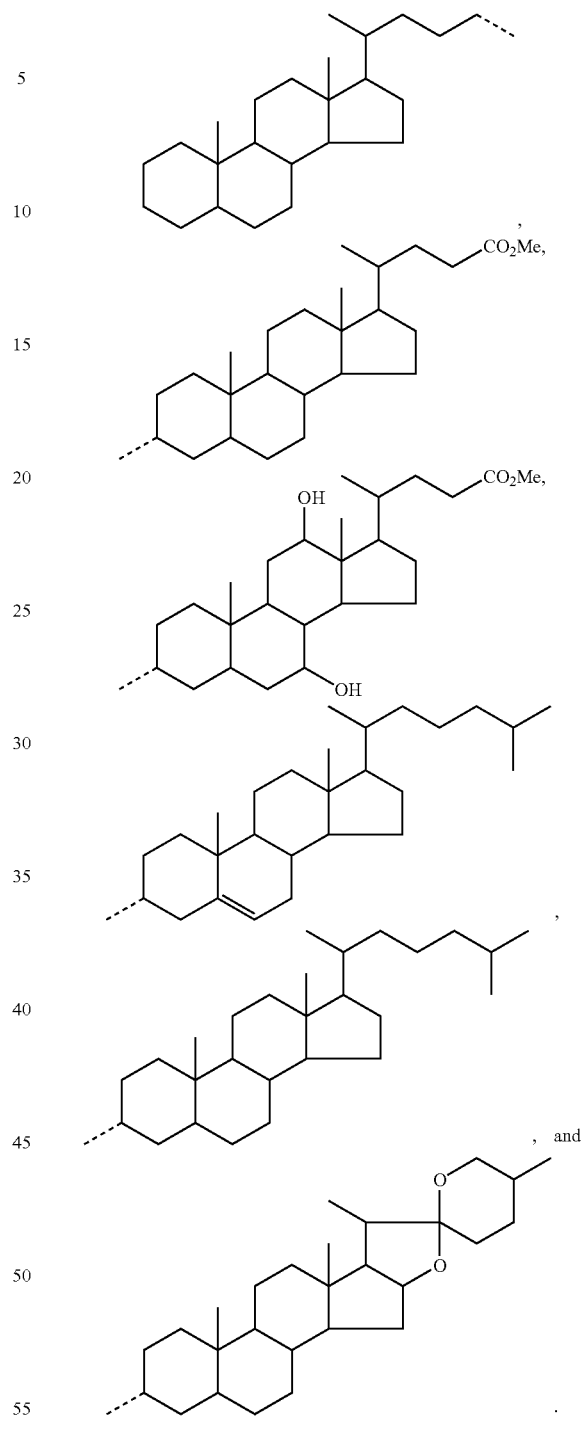
9. The nitrogen-containing organic compound of claim 7 which is one having the formula selected from the group consisting of the following formulae A-9 to A-62:
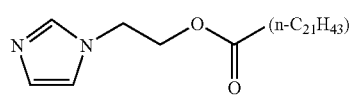
A-9

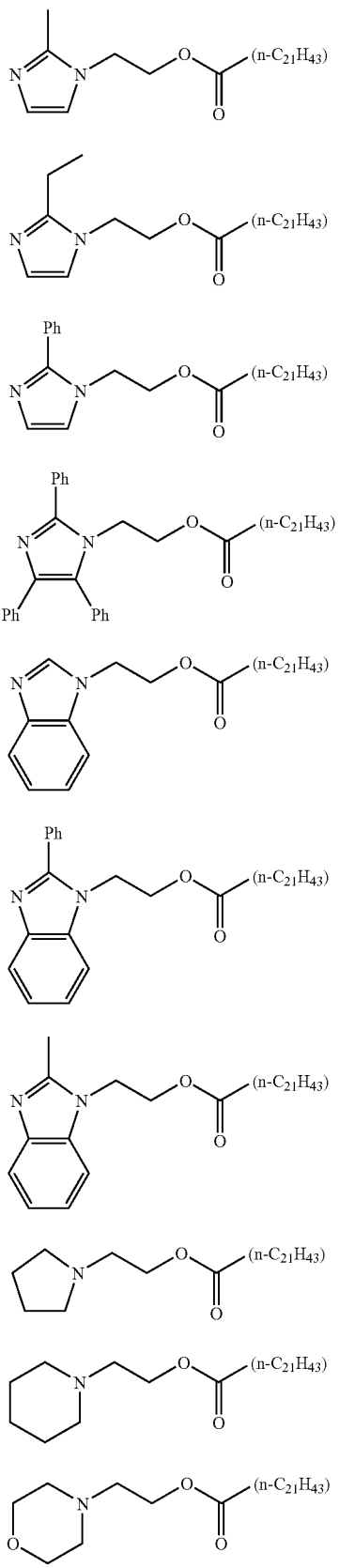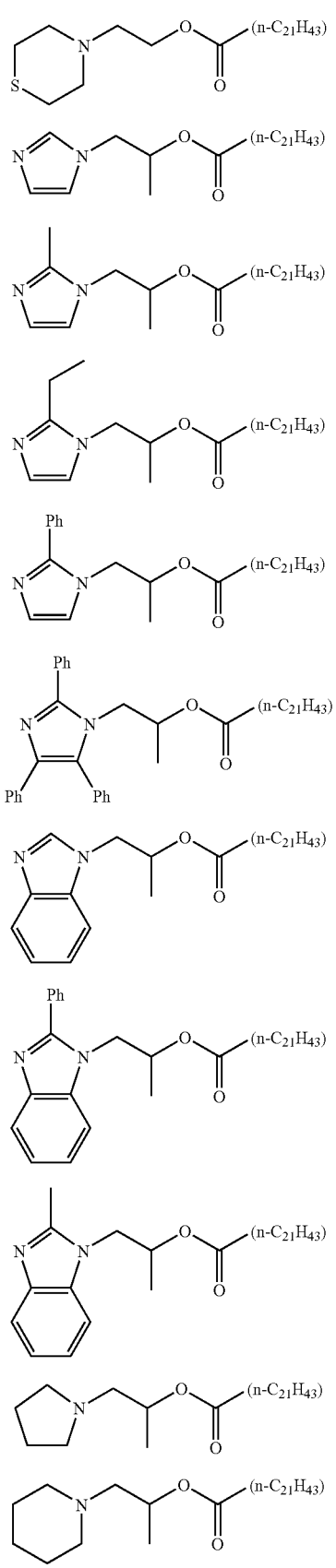

-continued
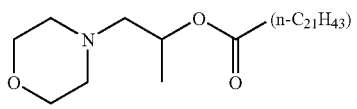 A-31
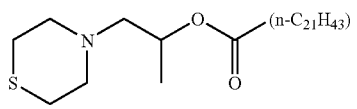 A-32
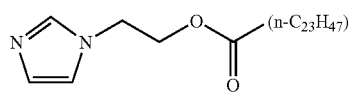 A-33
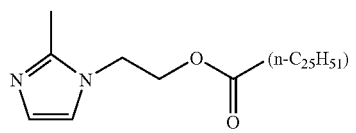 A-34
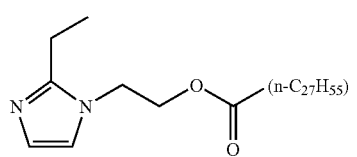 A-35
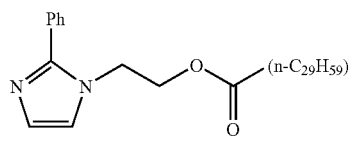 A-36
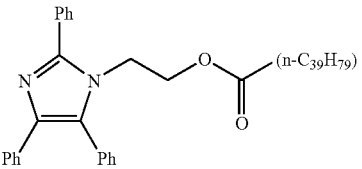 A-37
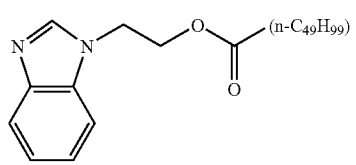 A-38
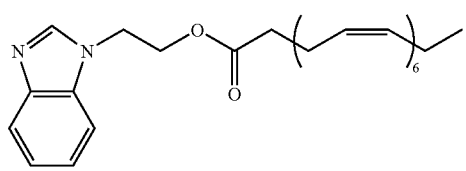 A-39
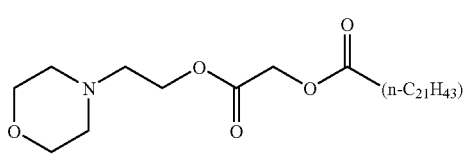 A-40
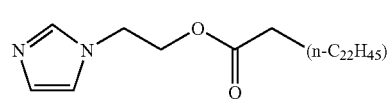 A-41
-continued
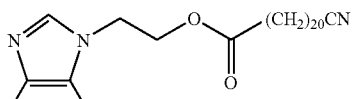 A-42
 A-43
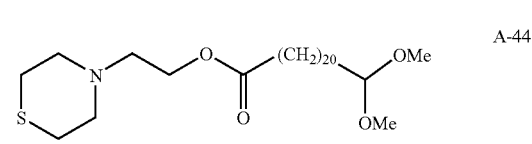 
 A-44
 A-45
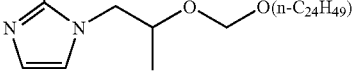 A-46
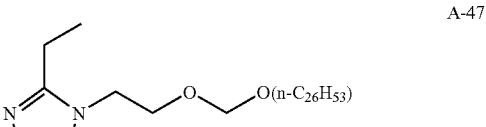 A-47
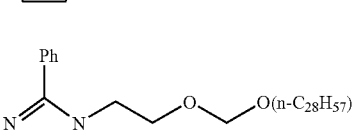 A-48
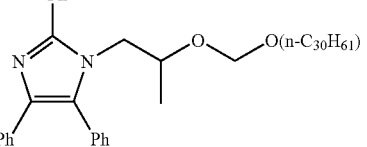 A-49
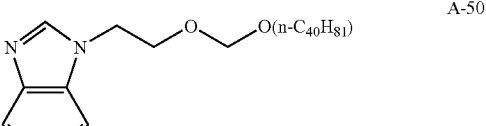 
 A-50
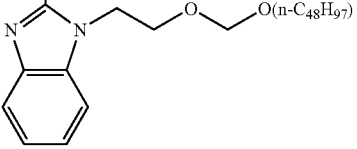 A-51

10. The nitrogen-containing organic compound of claim 8, which is one having the formula selected from the group consisting of the following formulae A-63 to A-76:

-continued
A-67
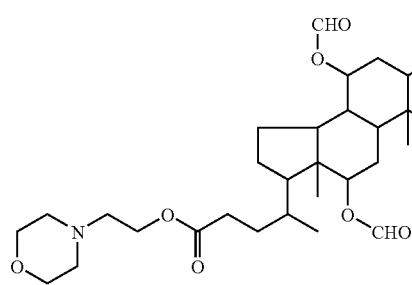
A-68
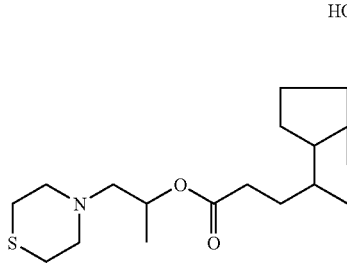
A-69
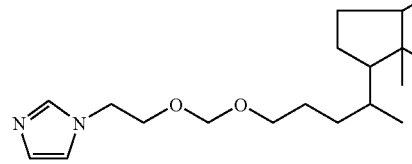
A-70
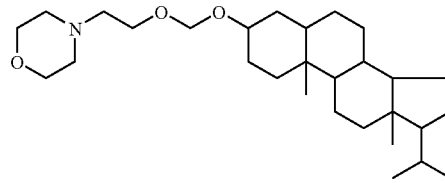
A-71
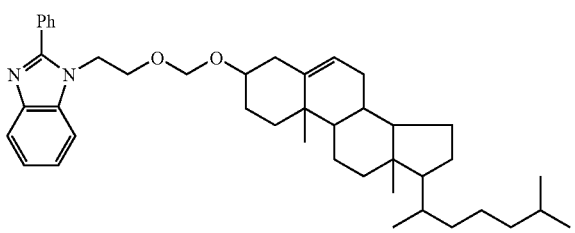
-continued
A-72
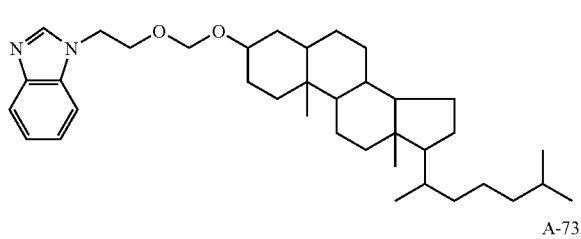
A-73
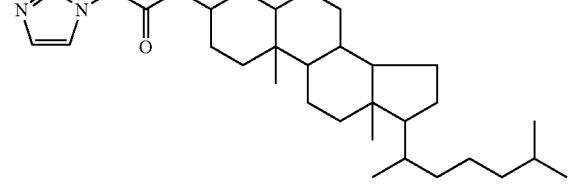
A-74
A-75
and
A-76
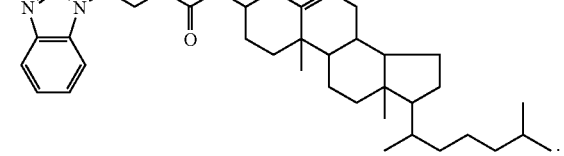
* * * * *